US009073931B2

(12) United States Patent
Leftheris et al.

(10) Patent No.: US 9,073,931 B2
(45) Date of Patent: Jul. 7, 2015

(54) LIVER X RECEPTOR MODULATORS

(71) Applicant: Vitae Pharmaceuticals, Inc., Fort Washington, PA (US)

(72) Inventors: Katerina Leftheris, San Diego, CA (US); Linghang Zhuang, Chalfont, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 14/385,671

(22) PCT Filed: Mar. 14, 2013

(86) PCT No.: PCT/US2013/031250
§ 371 (c)(1),
(2) Date: Sep. 16, 2014

(87) PCT Pub. No.: WO2013/138568
PCT Pub. Date: Sep. 19, 2013

(65) Prior Publication Data
US 2015/0065515 A1 Mar. 5, 2015

Related U.S. Application Data

(60) Provisional application No. 61/612,063, filed on Mar. 16, 2012.

(51) Int. Cl.
C07D 487/04 (2006.01)
A61K 31/4985 (2006.01)

(52) U.S. Cl.
CPC .......... C07D 487/04 (2013.01); A61K 31/4985 (2013.01)

(58) Field of Classification Search
CPC .................... C07D 487/04; A61K 31/4985
USPC ................ 544/330, 332, 344, 346; 514/250
See application file for complete search history.

(56) References Cited

U.S. PATENT DOCUMENTS

| 4,748,247 | A | 5/1988 | Abou-Gharbia |
| 5,356,862 | A | 10/1994 | Zimmerman |
| 5,545,636 | A | 8/1996 | Heath, Jr. et al. |
| 5,854,245 | A | 12/1998 | Duggan et al. |
| 6,177,440 | B1 | 1/2001 | Bach et al. |
| 2004/0087601 | A1 | 5/2004 | Erickson et al. |
| 2006/0128713 | A1 | 6/2006 | Jolidon et al. |
| 2006/0276453 | A1 | 12/2006 | Goldberg et al. |
| 2007/0078138 | A1 | 4/2007 | Palladino et al. |
| 2007/0155761 | A1 | 7/2007 | Bissantz et al. |
| 2008/0221122 | A1 | 9/2008 | Palladino et al. |
| 2009/0186879 | A1 | 7/2009 | Aso et al. |
| 2009/0192147 | A1 | 7/2009 | Ayral-Kaloustian et al. |
| 2010/0137320 | A1 | 6/2010 | Huang et al. |

FOREIGN PATENT DOCUMENTS

| CN | 101456863 A | 6/2009 |
| DE | 19802235 A1 | 7/1999 |
| EP | 572863 A1 | 12/1993 |
| EP | 950661 A1 | 10/1999 |
| FR | 2761073 A1 | 9/1998 |
| FR | 2829766 A1 | 3/2003 |
| WO | 9110668 | 7/1991 |
| WO | 95/17182 | 6/1995 |
| WO | 9612721 | 5/1996 |
| WO | 9800134 A1 | 1/1998 |
| WO | 9800144 A1 | 1/1998 |
| WO | 9800401 A1 | 1/1998 |
| WO | 9842710 A1 | 10/1998 |
| WO | 00/68202 A1 | 11/2000 |
| WO | WO 01/09136 | * 2/2001 |
| WO | 01/30331 A2 | 5/2001 |
| WO | 01/49288 A1 | 7/2001 |
| WO | 02/10169 A1 | 2/2002 |
| WO | 0210169 A1 | 2/2002 |
| WO | 02/059082 A2 | 8/2002 |
| WO | 02/072584 A2 | 9/2002 |
| WO | 03/059353 A1 | 7/2003 |
| WO | 2004/099212 A1 | 11/2004 |
| WO | 2005/077912 A1 | 8/2005 |
| WO | 2005/097108 A1 | 10/2005 |
| WO | 2005/105213 A2 | 11/2005 |
| WO | 2005/105805 A1 | 11/2005 |
| WO | 2005/113526 A2 | 12/2005 |
| WO | 2006/072608 A2 | 7/2006 |
| WO | 2006/106423 A2 | 10/2006 |
| WO | 2007/006688 A1 | 1/2007 |
| WO | 2007/035841 A1 | 3/2007 |
| WO | 2007/048847 A2 | 5/2007 |
| WO | 2007/065820 A1 | 6/2007 |
| WO | 2007/088277 A1 | 8/2007 |
| WO | 2007/117180 A1 | 10/2007 |
| WO | 2008/122115 A1 | 10/2008 |
| WO | 2009/003003 A2 | 12/2008 |
| WO | 2009/042092 A1 | 4/2009 |
| WO | 2009/086129 A1 | 7/2009 |
| WO | 2009/118411 A2 | 10/2009 |
| WO | 2010/089084 A1 | 8/2010 |
| WO | 2010/142402 A1 | 12/2010 |
| WO | 2011/005295 A1 | 1/2011 |
| WO | 2011/031816 A2 | 3/2011 |
| WO | 2011/031818 A2 | 3/2011 |
| WO | 2011/071725 A1 | 6/2011 |
| WO | 2011/109237 A2 | 9/2011 |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*

(Continued)

Primary Examiner — Deepak Rao
(74) Attorney, Agent, or Firm — McCarter & English LLP; Steven G. Davis; Michael J. DeGrazia

(57) ABSTRACT

Provided herein are novel compounds and pharmaceutically acceptable salts thereof that are liver X receptor modulators. Also provided are compositions comprising compounds of the invention and a carrier. Additionally, use of the compounds herein and methods for treating a disease or disorder associated with the liver X receptor are further described.

3 Claims, No Drawings

(56) References Cited

OTHER PUBLICATIONS

Jakobsson et al., Liver X receptor biology and pharmacology: new pathways, challenges and opportunities, Trends in Pharmacological Sciences, vol. 33, No. 7, pp. 394-404, 2012.*

Damasio, Alzheimer's Disease and Related Dementias, Cecil Textbook of Medicine, 20th Edition, vol. 2, pp. 1992-1996, 1996.*

Layzer, Degenerative Diseases of the Nervous System, Cecil Textbook of Medicine, 20th Edition, vol. 2, pp. 2050-2057, 1996.*

Pearce et al., Failure modes in anticancer drug discovery and development, Cancer Drug Design and Discovery Edited by Stephen Neidle, Chapter 18, pp. 424-435 (2008).*

Simone, Oncology: Introduction, Cecil Textbook of Medicine, 20th Edition, vol. 1, pp. 1004-1010, 1996.*

International Search Report for International Application No. PCT/US2013/031250; International Filing Date: Mar. 14, 2013; Mailed on Jun. 19, 2013; 10 pages.

Indian Patent Application IN 2000MA00368, Oct. 2014.

* cited by examiner

LIVER X RECEPTOR MODULATORS

REFERENCE TO RELATED APPLICATIONS

This application is a 35 U.S.C. §371 national stage filing of International Application No. PCT/US2013/031250, filed Mar. 14, 2013, which claims the benefit of the filing date of U.S. Provisional Application No. 61/612,063, filed on Mar. 16, 2012, the entire content of which is incorporated herein by reference.

FIELD OF THE INVENTION

The present invention relates to compounds that modulate the activity of liver X receptors.

BACKGROUND OF THE INVENTION

Atherosclerosis is the leading cause of death in the developed world, and atherosclerosis is predicted to be the leading cause of death in the developing world in the 21st century. Liver X receptors (LXRs) are ligand-activated transcription factors that play a crucial role in regulating the expression of genes involved in lipid metabolism and cellular cholesterol homeostasis. LXR agonists have been shown to enhance reverse cholesterol transport (RCT), facilitating cholesterol trafficking from the periphery back to the liver for processing and excretion. RCT occurs via upregulation of cholesterol transporters (ATP-Binding Cassettes: ABCA1 and ABCG1) in peripheral macrophages. Active RCT has the potential to inhibit the progression of atherosclerosis.

There are two isoforms of LXR, LXRα (NR1H3) and LXRβ (NR1H2) that are encoded by separate genes. LXRα expression is tissue-selective, detectable in liver, intestine, kidney, adipose tissue and adrenal glands, all of which are important for lipid homeostasis, whereas LXRβ is expressed ubiquitously. Both LXRs require the retinoid X receptor (RXR) as an obligate heterodimer partner to recognize and bind cooperatively to LXR response elements (LXREs) consisting of two direct repeats of a core hexameric sequence spaced by four nucleotides (DR4). The ligand binding domains of the two LXRs are fairly well conserved (~78% amino acid homology) and respond to endogenous ligands consisting of oxidized derivatives of cholesterol (oxysterols) that serve as intermediates in steroid hormone and bile acid synthesis. Among them, 22(R)-hydroxycholesterol, 24(S)-hydroxycholesterol, and 24(S), 25-epoxycholesterol are the most potent. These data suggested that LXRs are likely to play an important role in cholesterol regulation, which was later confirmed through gene knock-out studies in mice. Non-steroidal ligands have also been identified, and, using these as chemical probes many LXR-regulated genes have been discovered. Several LXRE-containing genes are involved in cholesterol metabolism, reverse cholesterol transport (RCT) and lipogenesis. Other genes involved in inflammation and carbohydrate metabolism lack LXREs, but are repressed by LXRs in a ligand-dependent manner. Based on these discoveries, the liver X receptors have recently emerged as unprecedented targets acting as intracellular cholesterol sensors, providing the basis for the treatment of a variety of diseases, including atherosclerosis, diabetes, Alzheimer's disease, skin disorders, reproductive disorders and cancer (Viennois et al., 2011, Expert Opin. Ther. Targets, 15(2):219-232). Additionally, it has been determined that LXR agonists modulate intestinal and renal sodium phosphate (NaPi) transporters and, in turn, serum phosphate levels (Caldas et al., 2011, Kidney International, 80:535-544). Thus, LXR is also a target for kidney disorders, and particularly for the prevention of hyperphosphatemia and associated cardiovascular complications. Recently, LXRs have been identified as targets in the treatment of osteoporosis and related diseases (Kleyer et al., 2012, J. Bone Miner. Res., 27(12):2442-51).

Alzheimer's disease is one of the most common forms of dementia, characterized by the accumulation and deposition of amyloid-beta (Aβ) peptides in the brain, leading to the perturbation of synaptic function and neuronal loss in the brains of affected individuals. Neurons in the brain produce Aβ peptides via cleavage of amyloid precursor protein (APP), and Aβ peptides are normally cleared through efflux into the peripheral circulation and by degradation by proteinases within the brain.

Apolipoprotein E (apoE) is associated with age-related risk for Alzheimer's disease and plays critical roles in Aβ homeostasis. LXR increases the expression of apoE and increases the lipidation of apoE. Degradation of Aβ both intra- and extracellularly is enhanced by lipidated apoE. LXR agonist treatment stimulated proteolytic degradation of Aβ, reduced plaque pathology, and improved memory in APP-expressing transgenic mice (Jiang et al., 2008, Neuron, 58:681-693).

In skin, keratinocytes are a critical component of the epidermis. The outer layer, stratum corneum, is primarily responsible for the permeability barrier to water and electrolyte transit. Keratinocytes in the epidermis undergo differentiation which culminates in keratinocyte cornification ("the bricks") and in formation of the extracellular lipid-enriched lamellar membranes ("the mortar") in the stratum corneum. Both LXRα and LXRβ are expressed in keratinocytes, and LXR expression and activation promotes epidermis barrier function. Activation of LXR is involved in keratinocyte differentiation, formation of the lamellar membrane and overall improvement of epidermal barrier function. Thus, LXR activation is expected to result in increased keratinocyte differentiation, increased lipid secretion (via ABCA1, ABCA12), and increased lamellar body formation, leading to a healthy epidermis (smooth skin).

The potential therapeutic utility of LXR agonists has led to the development of several high affinity LXR ligands with potent agonism for both receptor subtypes. The therapeutic utility of LXR agonists is constrained by their potential to induce lipogenic genes including sterol response element binding protein-1c (SREBP1c) and fatty acid synthase (FAS). Preclinical studies have demonstrated that synthetic modulators of LXRs reduce lesion progression in murine models of atherosclerosis with limited increase in hepatic lipogenesis. There is a clear need for new LXR chemotypes that retain the anti-atherosclerotic efficacy of current LXR agonists but are devoid of lipogenic activity. Compounds exhibiting a pharmacological profile with positive effects on RCT while being neutral or suppressive on lipogenic genes will be valuable therapeutic agents in patients with atherosclerotic dyslipidemia.

The present invention provides compounds that are liver X receptor agonists and are useful as therapeutic agents for the promotion of reverse cholesterol transport and the suppression of hepatic lipogenesis, and for the prevention, amelioration or treatment of diseases or disorders including atherosclerosis, Alzheimer's disease, dermatitis, and dyslipidemia in a patient.

SUMMARY OF THE INVENTION

Disclosed are LXR modulators that are useful as therapeutic agents for the promotion of reverse cholesterol transport and the suppression of hepatic lipogenesis, and for the prevention, amelioration or treatment of diseases or disorders including atherosclerosis and dyslipidemia in a subject. The disclosed LXR modulators are selective for the LXRβ subtype over the LXRα subtype (see e.g., Example 6, isomer 1; Example 7, isomer 1; and Example 13, isomer 1).

One embodiment of the invention is a compound represented by structural formula I:

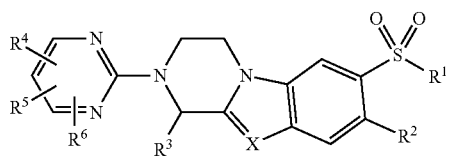

I or a pharmaceutically acceptable salt thereof.

X is N or CR$^c$.

R$^1$ is alkyl or —NR$^a$R$^b$.

R$^2$ is H; halogen; —CN; —NRC(O)R; —C(O)OR; —C(O)NR$^a$R$^b$; monocyclic heteroaromatic optionally substituted with one or more groups selected from alkyl, —CN, —NRC(O)R, —C(O)OR, —C(O)NR$^a$R$^b$ and halogen; monocyclic non-aromatic heterocycle optionally substituted with one or more groups selected from alkyl, halogen, —CN and =O; or alkyl optionally substituted by one or more groups selected from halogen, hydroxy, alkoxy, —NR$^a$R$^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —OC(O)N(R)$_2$ and —C(O)NR$^a$R$^b$.

R$^3$ is alkyl, haloalkyl, hydroxyalkyl, alkoxyalkyl, cycloalkyl, monocyclic non-aromatic heterocycle, monocyclic heteroaromatic or phenyl, wherein the phenyl, monocyclic non-aromatic heterocycle and monocyclic heteroaromatic group represented by R$^3$ are optionally substituted with one or more groups selected from alkyl, halogen, haloalkyl, alkoxy, haloalkoxy, nitro and —CN.

R$^4$ and R$^5$ independently are halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO2N(R)2, haloalkyl, haloalkoxy, cycloalkoxy, cycloalkyl, monocyclic non-aromatic heterocycle, monocyclic heteroaromatic or alkyl, wherein the alkyl, monocyclic non-aromatic heterocycle and monocyclic heteroaromatic group represented by R$^4$ or R$^5$ are optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$.

R$^6$ is H, halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl or alkyl, wherein the alkyl group represented by R$^6$ is optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$; or R$^5$ and R$^6$, taken together with the carbon atoms to which they are bonded, form a moncyclic non-aromatic heterocycle optionally substituted with one or more groups selected from alkyl, halogen, hydroxyalkyl, alkoxyalkyl, haloalkyl and =O.

Each R independently is H or alkyl.

R$^a$ and R$^b$ are independently H, alkyl or R$^a$ and R$^b$ can be taken together with the nitrogen to which they are attached to form a monocyclic non-aromatic heterocycle.

R$^c$ is H, alkyl, or halogen.

Another aspect of the invention is a pharmaceutical composition comprising a compound of the invention and a pharmaceutically acceptable carrier or diluent.

A further aspect of the present invention also provides for a method of treating a subject with a disease or disorder that is treatable by upregulating LXR activity. The method comprises administering an effective amount of a compound of the invention or a pharmaceutically acceptable salt thereof to the subject in need thereof.

Also provided in the invention is the use of a compound of the invention for the manufacture of a medicament for treating a subject with a disease or disorder that is treatable by upregulating LXR activity in a subject in need thereof.

Disclosed herein is also a compound of the invention for use in treating a disease or disorder that is treatable by upregulating LXR activity in a subject in need thereof.

Another embodiment of the invention is an intermediate compound used in the preparation of an LXR modulator and is represented by structural formula Ia:

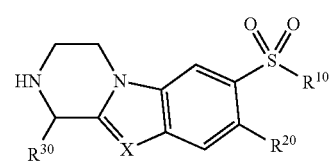

Ia or a salt thereof.

X is N or CR$^c$.

R$^{10}$ is alkyl or —NR$^a$R$^b$.

R$^{20}$ is H; halogen; —CN; —NRC(O)R; —C(O)OR; —C(O)NR$^a$R$^b$; monocyclic heteroaromatic optionally substituted with one or more groups selected from alkyl, —CN, —NRC(O)R, —C(O)OR, —C(O)NR$^a$R$^b$ and halogen; monocyclic non-aromatic heterocycle optionally substituted with one or more groups selected from alkyl, halogen, —CN and =O; or alkyl optionally substituted by one or more groups selected from halogen, hydroxy, alkoxy, —NR$^a$R$^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —OC(O)N(R)$_2$, —C(O)NR$^a$R$^b$, and —O(protecting group).

R$^{30}$ is alkyl, haloalkyl, hydroxyalkyl, alkoxyalkyl, cycloalkyl or phenyl, wherein the phenyl group represented by R$^{30}$ is optionally substituted with one or more groups selected from alkyl, halogen, haloalkyl, alkoxy, haloalkoxy, nitro and —CN.

Each R independently is H or alkyl.

R$^a$ and R$^b$ are independently H, alkyl or R$^a$ and R$^b$ can be taken together with the nitrogen to which they are attached to form a monocyclic non-aromatic heterocycle.

R$^c$ is H, alkyl, or halogen.

DETAILED DESCRIPTION OF THE INVENTION

A. Compounds

The compound(s) of the invention provided herein (or intermediate(s) used in their preparation) include both the neutral form and a pharmaceutically acceptable salt thereof.

In one embodiment, the compound is represented by structural formula II, III, IV, V, VI, or VII or a pharmaceutically acceptable salt thereof wherein the values for the variables are as defined for Formula I above.

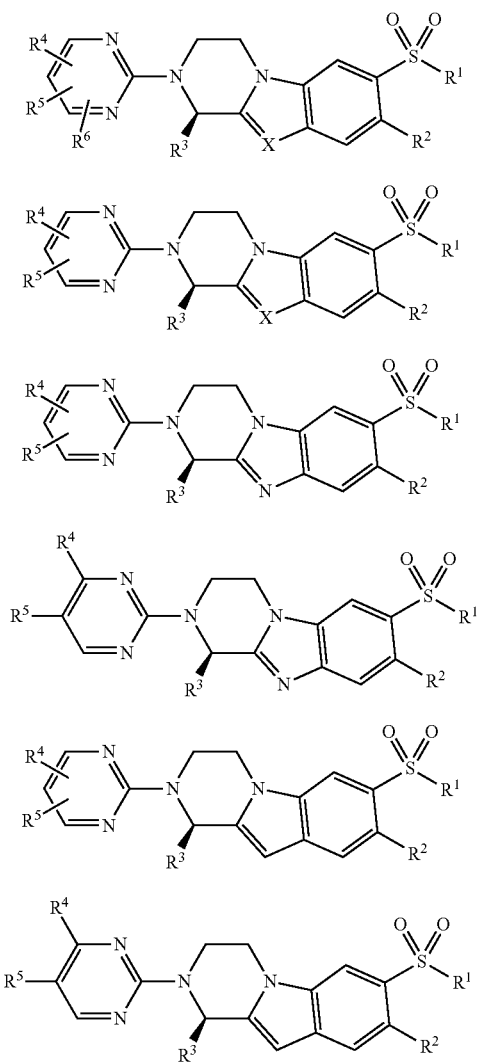

In a first alternative embodiment of any compound of formulas I through VII, the variables are defined as follows.

$R^3$ is alkyl, haloalkyl, hydroxyalkyl, alkoxyalkyl, cycloalkyl, or phenyl, wherein the phenyl group represented by $R^3$ is optionally substituted with one or more groups selected from alkyl, halogen, haloalkyl, alkoxy, haloalkoxy, nitro and —CN;

$R^4$ and $R^5$ independently are halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO2N(R)$_2$, haloalkyl, haloalkoxy, cycloalkoxy, cycloalkyl or alkyl, wherein the alkyl represented by $R^4$ or $R^5$ is optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$;

$R^6$ is H, halogen, —CN, —OR, —SR, —N(R)$_2$, —C(O)R, —C(O)OR, —OC(O)O(alkyl), —C(O)O(haloalkyl), —OC(O)R, —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$, —NRSO$_2$N(R)$_2$, haloalkyl, haloalkoxy, cycloalkoxy, cycloalkyl or alkyl, wherein the alkyl group represented by $R^6$ is optionally substituted with one or more groups selected from —CN, —OR, —SR, —N(R)$_2$, =O, —C(O)R, —C(O)OR, —C(O)O(haloalkyl), —OC(O)R, —OC(O)O(alkyl), —C(O)N(R)$_2$, —OC(O)N(R)$_2$, —NRC(O)R, —NRC(O)O(alkyl), —S(O)R, —SO$_2$R, —SO$_2$N(R)$_2$, —NRS(O)R, —NRSO$_2$R, —NRC(O)N(R)$_2$ and —NRSO$_2$N(R)$_2$.

In a second alternative embodiment of any compound of formulas I through VII, the variables are defined as follows.

$R^1$ is methyl or —NH$_2$.

$R^2$ is H or methyl, wherein the methyl group represented by $R^2$ is optionally substituted with one or more groups selected from halogen, hydroxy, alkoxy, —NR$^a$R$^b$, —NRC(O)R, —NRC(O)O(alkyl), —NRC(O)N(R)$_2$, —C(O)OR, thiol, alkylthiol, nitro, —CN, =O, —OC(O)H, —OC(O)(alkyl), —OC(O)O(alkyl), —C(O)NR$^a$R$^b$ and —OC(O)N(R)$_2$. Preferably, $R^2$ is H or —CH$_2$OH.

$R^3$ is methyl, ethyl, propyl, isopropyl, tert-butyl, sec-butyl, iso-butyl, —CH$_2$CF$_3$, —CH(CH$_2$F)$_2$, —CH(CHF$_2$)$_2$, —CH(CF$_3$)$_2$, —CF(CH$_3$)$_2$, —CF$_3$, cyclopropyl, cyclobutyl, cyclopentyl, cyclohexyl, —C(OH)(CH$_3$)$_2$, —CH(OH)(CH$_3$), or phenyl, wherein the phenyl group represented by $R^3$ is optionally substituted with one or more groups selected from alkyl, halogen, haloalkyl, alkoxy, haloalkoxy, nitro and —CN.

$R^c$, where present, is H.

The values for the remaining variables are as defined for Formula I or for the first alternative embodiment.

In a third alternative embodiment of any compound of formulas I through VII, $R^1$ is methyl; $R^2$ is —CH$_2$OH; and $R^3$ is isopropyl. The values for the remaining variables are as defined for Formula I or for the first or second alternative embodiment.

In a fourth alternative embodiment of any compound of formulas I through VII, $R^4$ and $R^5$ independently are halogen, hydroxy, alkyl, cycloalkyl, cycloalkoxy, alkoxy, haloalkoxy, haloalkyl, —N(R)$_2$, —C(O)OH, —C(O)O(alkyl), —C(O)O(haloalkyl), —C(O)(alkyl), —C(O)N(R)$_2$, —NRC(O)R, —SO$_2$N(R)$_2$, —OC(O)N(R)$_2$, —CN, hydroxyalkyl or dihydroxyalkyl. The values for the remaining variables are as defined for Formula I or for the first, second or third alternative embodiments.

In a fifth alternative embodiment of any compound of formulas I through VII, $R^4$ is alkyl, haloalkyl, cycloalkyl, alkoxy, or haloalkoxy. The values for the remaining variables are as defined for Formula I or for the first, second, third or fourth alternative embodiments.

In a sixth alternative embodiment of any compound of formulas I through VII, $R^4$ and $R^5$ independently are methyl, ethyl, hydroxy, —CF$_3$, isopropyl, cyclopropyl, —CH$_2$OH, —CH(OH)(CH$_2$)(OH), —C(OH)(CH$_3$)$_2$, —CH(OH)(CH$_3$), —CH(OH)(CH₂)(CH₃), —CH(OH)(CH₂)₂(CH₃), —C(O)NH₂, —C(O)N(CH₃)₂, —C(O)OH, —C(O)NH(CH₃), —C(O)CH₃, —C(O)CH₂CH₃, —C(O)O(CH₂)(CH₃), —C(O)O(tert-butyl), —C(O)O(C)(CH₃)₂(CF₃), —NHC(O)CH₃, —OCHF₂, —OCF₃, —OCH₂CH₃, —OCH(CH₃)₂ or —OCH₃. Preferably, R⁴ is as just described and R⁵ is —C(OH)(CH₃)₂. The values for the remaining variables are as defined for Formula I or for the first, second, third, fourth or fifth alternative embodiments.

In a seventh alternative embodiment of any compound of formulas I through VII, R⁴ is methyl, halogenated methyl, cyclopropyl, —OCHF₂ or —OCH₃. Preferably, R⁴ is CF₃. The values for the remaining variables are as defined for Formula I or for the first, second, third, fourth, fifth or six alternative embodiments.

Another embodiment of the invention is a compound represented by formulas I, II, III, IV, V, VI or VII or a pharmaceutically acceptable salt thereof, wherein the variables are as defined for formula I or in the first, second, third, fourth, fifth, sixth or seventh alternative embodiments, provided that the compound comprises at least one group represented by —C(O)OR.

Another embodiment of the invention is a compound represented by formula I, II, III, IV, V, VI or VII or a pharmaceutically acceptable salt thereof, wherein the variables are as defined for formula (I) or in the first, second, third, fourth, fifth, sixth or seventh alternative embodiment, provided that the compound comprises no groups represented by —C(O)OR.

The compounds of the invention (or intermediate(s) used in their preparation) contain at least one chiral center and, therefore, exist as enantiomers. When compounds of the invention are depicted or named without indicating the stereochemistry, it is to be understood that enantiomerically pure forms and mixtures of enantiomers, including racemic mixtures, are encompassed.

When a compound is designated by a name or structure that indicates a single enantiomer, unless indicated otherwise, the compound is at least 50%, 60%, 70%, 80%, 90%, 95%, 99%, 99.5% or 99.9% optically pure (also referred to as "enantiomerically pure"). Optical purity is the weight in the mixture of the named or depicted enantiomer divided by the total weight in the mixture of both enantiomers.

When a compound is designated by a name or structure that indicates a specific stereochemistry at a chiral center, unless indicated otherwise, the compound is at least 50%, 60%, 70%, 80%, 90%, 95%, 99%, 99.5% or 99.9% stereoisomerically pure. Stereoisomeric purity is the weight in the mixture of the named or depicted stereoisomer(s) divided by the total weight in the mixture of all stereoisomers.

In an eighth alternative embodiment, a compound of the invention is depicted by a structural formula in Table 1 or a pharmaceutically acceptable salt thereof. In an eighth alternative embodiment, a compound of the invention is selected from any one of compounds E6a, E1a, E13a, E18 and E27a or a pharmaceutically acceptable salt thereof.

TABLE 1

| Compound No. | Example No. | Structure |
|---|---|---|
| E1 | Example 01 | 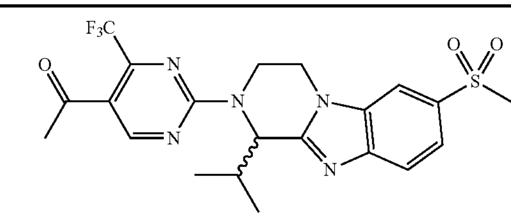 |
| E2 | Example 02 | 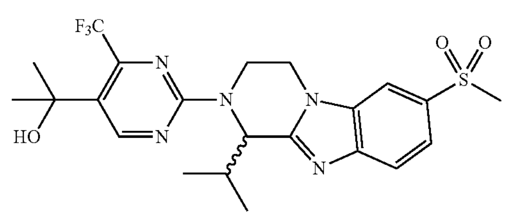 [SMILES: CC(C)C1c2nc3ccc(S(C)(=O)=O)cc3n2CCN1c1ncc(C(C)(C)O)c(C(F)(F)F)n1] |
| E3 | Example 03 | 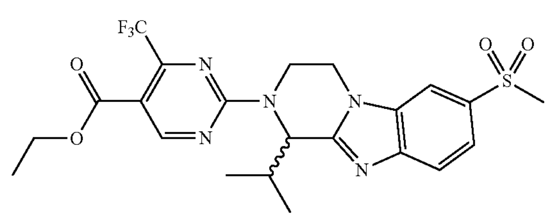 [SMILES: CCOC(=O)c1cnc(N2CCn3c(nc4ccc(S(C)(=O)=O)cc43)C2C(C)C)nc1C(F)(F)F] |
| E4 | Example 04 | 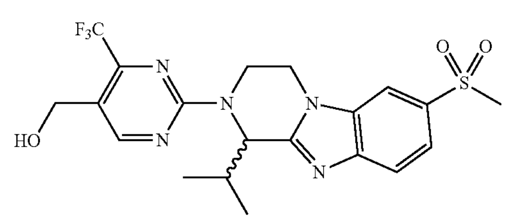 [SMILES: CC(C)C1c2nc3ccc(S(C)(=O)=O)cc3n2CCN1c1ncc(CO)c(C(F)(F)F)n1] |

TABLE 1-continued

| Compound No. | Example No. | Structure |
| --- | --- | --- |
| E5 | Example 05 | 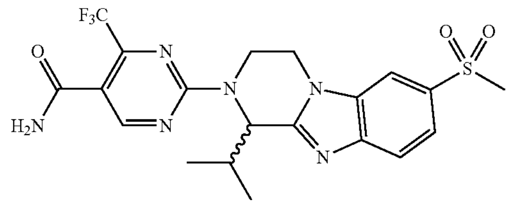 [SMILES: CC(C)C1c2nc3ccc(S(C)(=O)=O)cc3n2CCN1c1ncc(C(N)=O)c(C(F)(F)F)n1] |
| E6a | Example 06, isomer 1 | 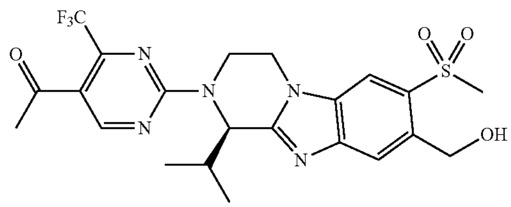 [SMILES: CC(=O)c1cnc(N2CCn3c(nc4cc(CO)c(S(C)(=O)=O)cc43)[C@H]2C(C)C)nc1C(F)(F)F] |
| E6b | Example 06, isomer 2 | 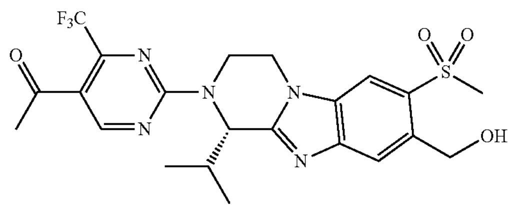 [SMILES: CC(=O)c1cnc(N2CCn3c(nc4cc(CO)c(S(C)(=O)=O)cc43)[C@@H]2C(C)C)nc1C(F)(F)F] |
| E7a | Example 07, isomer 1 | 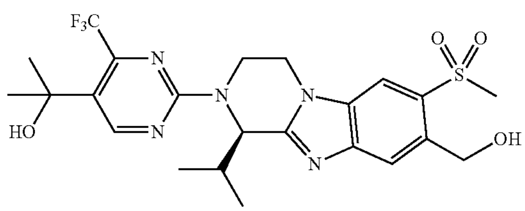 [SMILES: CC(C)[C@@H]1c2nc3cc(CO)c(S(C)(=O)=O)cc3n2CCN1c1ncc(C(C)(C)O)c(C(F)(F)F)n1] |
| E7b | Example 07, isomer 2 | 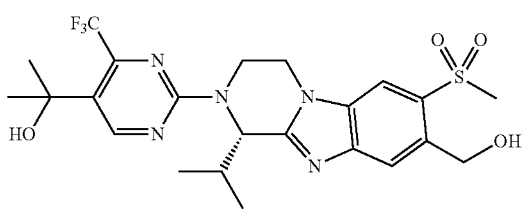 [SMILES: CC(C)[C@H]1c2nc3cc(CO)c(S(C)(=O)=O)cc3n2CCN1c1ncc(C(C)(C)O)c(C(F)(F)F)n1] |
| E8a | Example 08, isomer 1 | 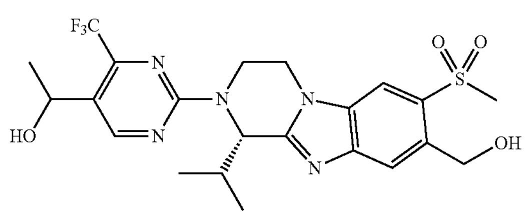 [SMILES: CC(O)c1cnc(N2CCn3c(nc4cc(CO)c(S(C)(=O)=O)cc43)[C@@H]2C(C)C)nc1C(F)(F)F] |
| E8b | Example 08, isomer 2 | 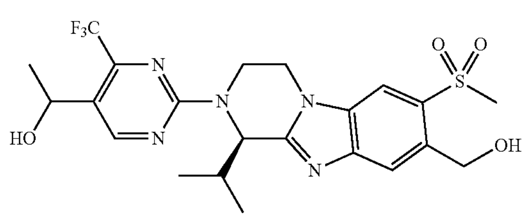 [SMILES: CC(O)c1cnc(N2CCn3c(nc4cc(CO)c(S(C)(=O)=O)cc43)[C@H]2C(C)C)nc1C(F)(F)F] |

TABLE 1-continued

| Compound No. | Example No. | Structure |
|---|---|---|
| E8c | Example 08, isomer 3 | 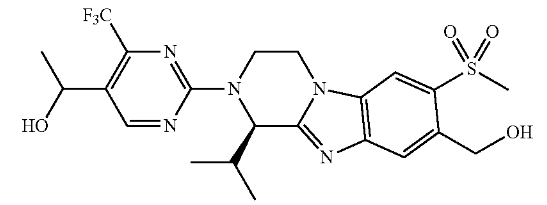 |
| E8d | Example 08, isomer 4 | 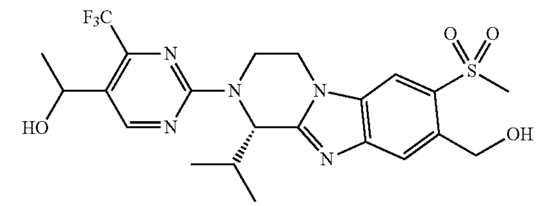 [SMILES: CC(O)c1cnc(N2CCn3c(nc4cc(CO)c(S(C)(=O)=O)cc43)[C@@H]2C(C)C)nc1C(F)(F)F] |
| E9a | Example 09, isomer 1 | 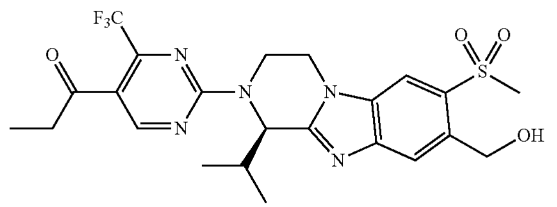 |
| E9b | Example 09, isomer 2 | 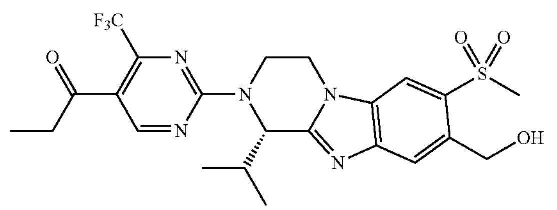 [SMILES: CCC(=O)c1cnc(N2CCn3c(nc4cc(CO)c(S(C)(=O)=O)cc43)[C@@H]2C(C)C)nc1C(F)(F)F] |
| E10a | Example 10, isomer 1 | 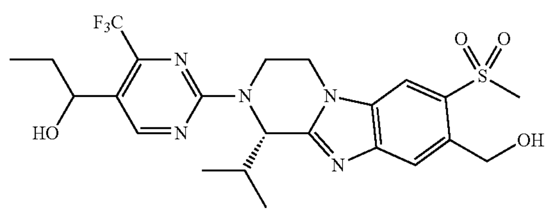 [SMILES: CCC(O)c1cnc(N2CCn3c(nc4cc(CO)c(S(C)(=O)=O)cc43)[C@@H]2C(C)C)nc1C(F)(F)F] |
| E10b | Example 10, isomer 2 | 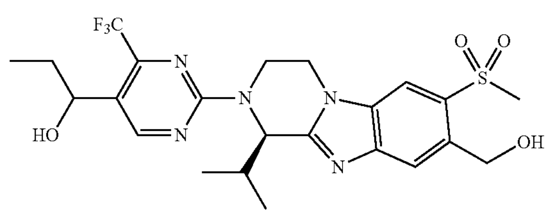 [SMILES: CCC(O)c1cnc(N2CCn3c(nc4cc(CO)c(S(C)(=O)=O)cc43)[C@H]2C(C)C)nc1C(F)(F)F] |
| E10c | Example 10, isomer 3 | 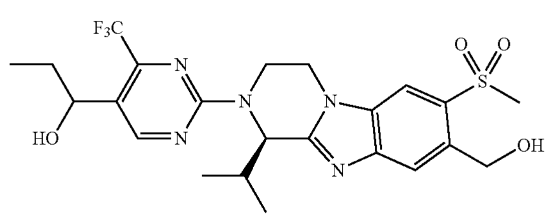 [SMILES: CCC(O)c1cnc(N2CCn3c(nc4cc(CO)c(S(C)(=O)=O)cc43)[C@H]2C(C)C)nc1C(F)(F)F] |

TABLE 1-continued

| Compound No. | Example No. | Structure |
|---|---|---|
| E10d | Example 10, isomer 4 | 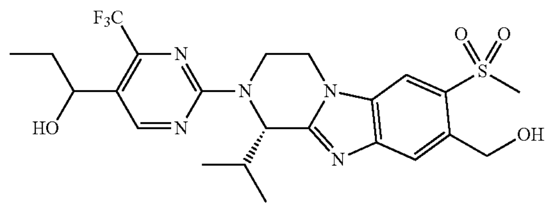 [SMILES: CCC(O)c1cnc(N2CCn3c(nc4cc(CO)c(S(C)(=O)=O)cc43)[C@@H]2C(C)C)nc1C(F)(F)F] |
| E11a | Example 11, isomer 1 | 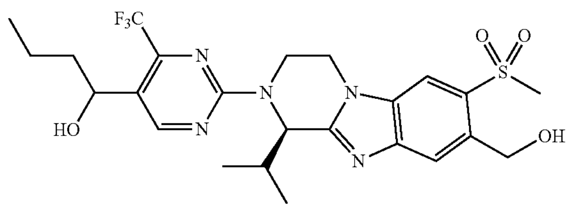 [SMILES: CCCC(O)c1cnc(N2CCn3c(nc4cc(CO)c(S(C)(=O)=O)cc43)[C@H]2C(C)C)nc1C(F)(F)F] |
| E11b | Example 11, isomer 2 | 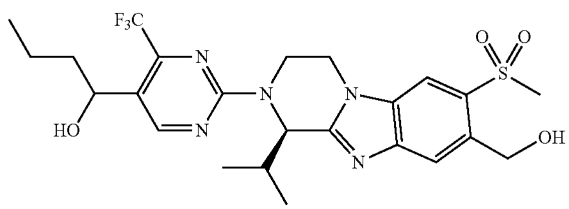 [SMILES: CCCC(O)c1cnc(N2CCn3c(nc4cc(CO)c(S(C)(=O)=O)cc43)[C@H]2C(C)C)nc1C(F)(F)F] |
| E12 | Example 12 | 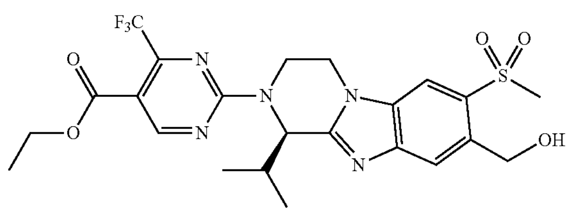 [SMILES: CCOC(=O)c1cnc(N2CCn3c(nc4cc(CO)c(S(C)(=O)=O)cc43)[C@H]2C(C)C)nc1C(F)(F)F] |
| E13a | Example 13, isomer 1 | 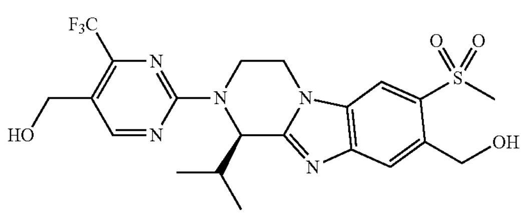 [SMILES: CC(C)[C@@H]1c2nc3cc(CO)c(S(C)(=O)=O)cc3n2CCN1c1ncc(CO)c(C(F)(F)F)n1] |
| E13b | Example 13, isomer 2 | 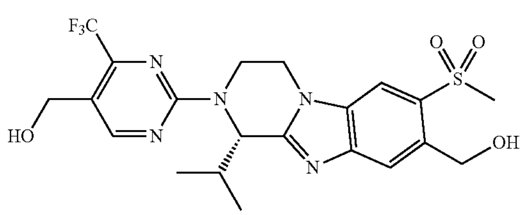 [SMILES: CC(C)[C@H]1c2nc3cc(CO)c(S(C)(=O)=O)cc3n2CCN1c1ncc(CO)c(C(F)(F)F)n1] |
| E14a | Example 14, isomer 1 | 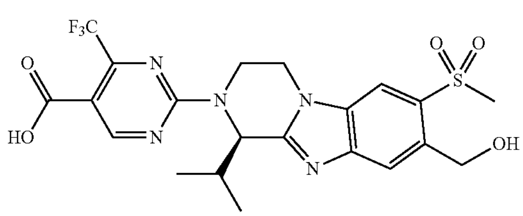 [SMILES: CC(C)[C@@H]1c2nc3cc(CO)c(S(C)(=O)=O)cc3n2CCN1c1ncc(C(=O)O)c(C(F)(F)F)n1] |

TABLE 1-continued

| Compound No. | Example No. | Structure |
|---|---|---|
| E14b | Example 14, isomer 2 | 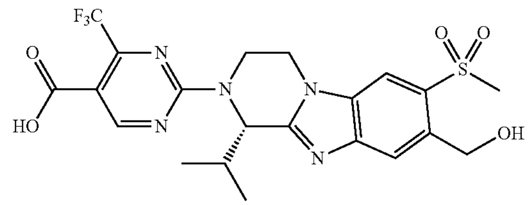 [SMILES: CC(C)[C@H]1c2nc3cc(CO)c(S(C)(=O)=O)cc3n2CCN1c1ncc(C(=O)O)c(C(F)(F)F)n1] |
| E15a | Example 15, isomer 1 | 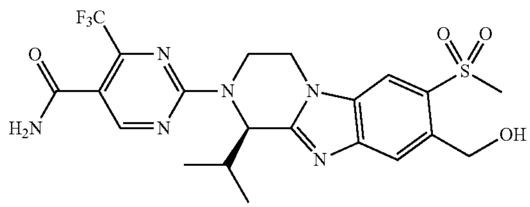 [SMILES: CC(C)[C@@H]1c2nc3cc(CO)c(S(C)(=O)=O)cc3n2CCN1c1ncc(C(N)=O)c(C(F)(F)F)n1] |
| E15b | Example 15, isomer 2 | 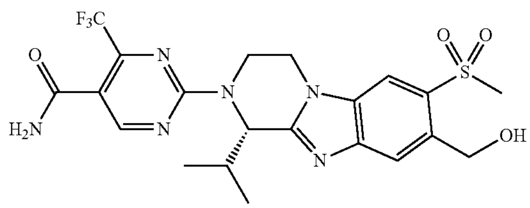 [SMILES: CC(C)[C@H]1c2nc3cc(CO)c(S(C)(=O)=O)cc3n2CCN1c1ncc(C(N)=O)c(C(F)(F)F)n1] |
| E16a | Example 16, isomer 1 | 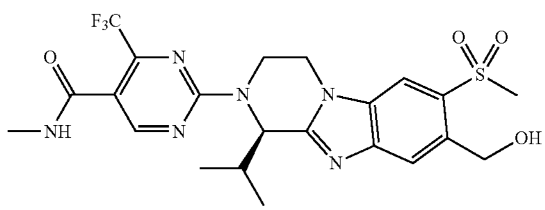 [SMILES: CNC(=O)c1cnc(N2CCn3c(nc4cc(CO)c(S(C)(=O)=O)cc43)[C@H]2C(C)C)nc1C(F)(F)F] |
| E16b | Example 16, isomer 2 | 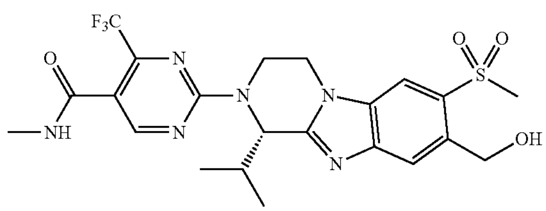 [SMILES: CNC(=O)c1cnc(N2CCn3c(nc4cc(CO)c(S(C)(=O)=O)cc43)[C@@H]2C(C)C)nc1C(F)(F)F] |
| E17a | Example 17, isomer 1 | 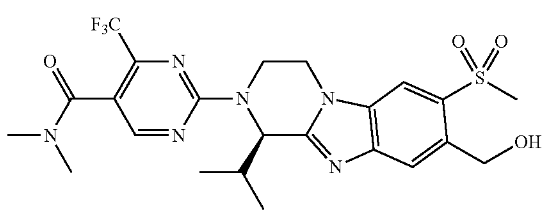 [SMILES: CC(C)[C@@H]1c2nc3cc(CO)c(S(C)(=O)=O)cc3n2CCN1c1ncc(C(=O)N(C)C)c(C(F)(F)F)n1] |
| E17b | Example 17, isomer 2 | 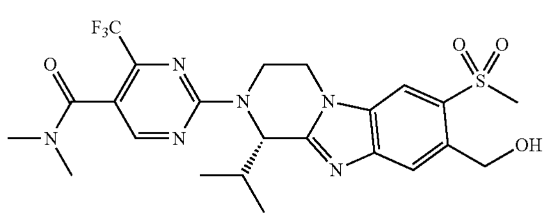 [SMILES: CC(C)[C@H]1c2nc3cc(CO)c(S(C)(=O)=O)cc3n2CCN1c1ncc(C(=O)N(C)C)c(C(F)(F)F)n1] |

TABLE 1-continued

| Compound No. | Example No. | Structure |
|---|---|---|
| E18 | Example 18 | 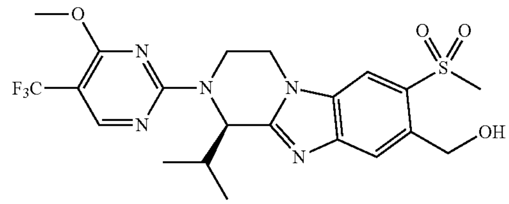 [SMILES: COc1nc(N2CCn3c(nc4cc(CO)c(S(C)(=O)=O)cc43)[C@H]2C(C)C)ncc1C(F)(F)F] |
| E19 | Example 19 | 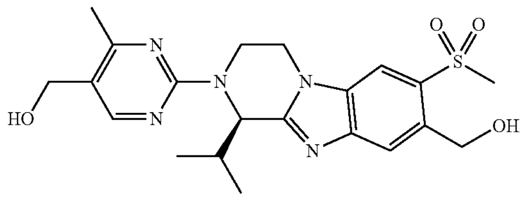 [SMILES: Cc1nc(N2CCn3c(nc4cc(CO)c(S(C)(=O)=O)cc43)[C@H]2C(C)C)ncc1CO] |
| E20a | Example 20, isomer 1 | 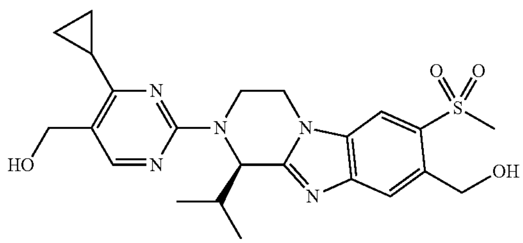 [SMILES: CC(C)[C@@H]1c2nc3cc(CO)c(S(C)(=O)=O)cc3n2CCN1c1ncc(CO)c(C2CC2)n1] |
| E20b | Example 20, isomer 2 | 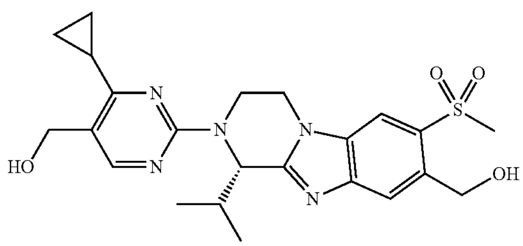 [SMILES: CC(C)[C@H]1c2nc3cc(CO)c(S(C)(=O)=O)cc3n2CCN1c1ncc(CO)c(C2CC2)n1] |
| E21 | Example 21 | 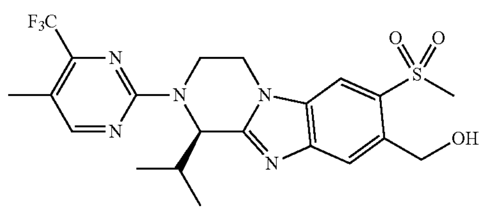 [SMILES: Cc1cnc(N2CCn3c(nc4cc(CO)c(S(C)(=O)=O)cc43)[C@H]2C(C)C)nc1C(F)(F)F] |
| E22a | Example 22, isomer 1 | 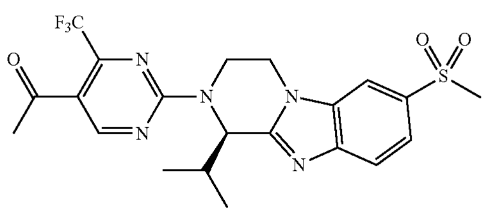 [SMILES: CC(=O)c1cnc(N2CCn3c(nc4ccc(S(C)(=O)=O)cc43)[C@H]2C(C)C)nc1C(F)(F)F] |
| E22b | Example 22, isomer 2 | 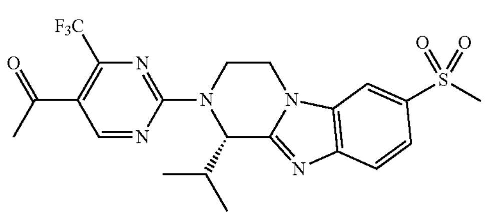 [SMILES: CC(=O)c1cnc(N2CCn3c(nc4ccc(S(C)(=O)=O)cc43)[C@@H]2C(C)C)nc1C(F)(F)F] |

TABLE 1-continued

| Compound No. | Example No. | Structure |
|---|---|---|
| E23a | Example 23, isomer 1 | 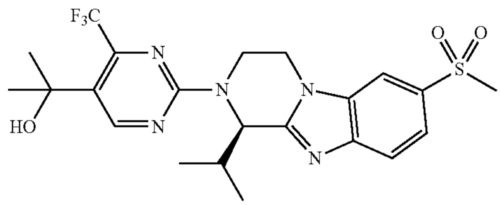 [SMILES: CC(C)[C@@H]1c2nc3ccc(S(C)(=O)=O)cc3n2CCN1c1ncc(C(C)(C)O)c(C(F)(F)F)n1] |
| E23b | Example 23, isomer 2 | 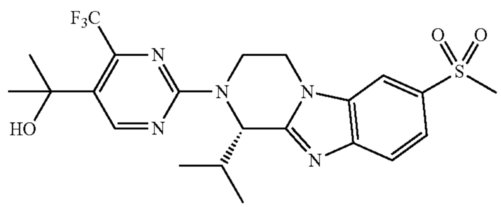 [SMILES: CC(C)[C@H]1c2nc3ccc(S(C)(=O)=O)cc3n2CCN1c1ncc(C(C)(C)O)c(C(F)(F)F)n1] |
| E24a | Example 24, isomer 1 | 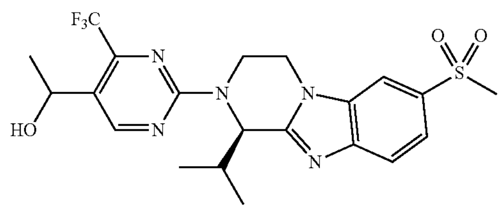 [SMILES: CC(O)c1cnc(N2CCn3c(nc4ccc(S(C)(=O)=O)cc43)[C@H]2C(C)C)nc1C(F)(F)F] |
| E24b | Example 24, isomer 2 | 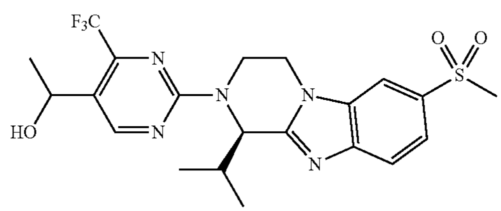 [SMILES: CC(O)c1cnc(N2CCn3c(nc4ccc(S(C)(=O)=O)cc43)[C@H]2C(C)C)nc1C(F)(F)F] |
| E24c | Example 24, isomer 3 | 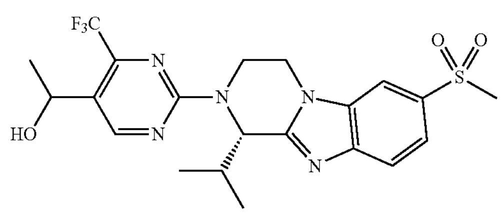 [SMILES: CC(O)c1cnc(N2CCn3c(nc4ccc(S(C)(=O)=O)cc43)[C@@H]2C(C)C)nc1C(F)(F)F] |
| E24d | Example 24, isomer 4 | 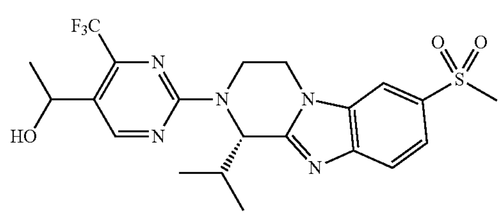 [SMILES: CC(O)c1cnc(N2CCn3c(nc4ccc(S(C)(=O)=O)cc43)[C@@H]2C(C)C)nc1C(F)(F)F] |
| E25a | Example 25, isomer 1 | 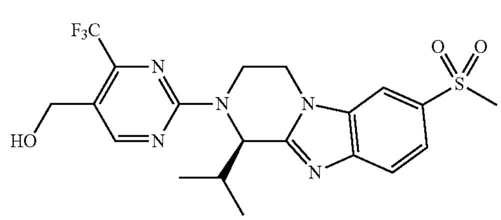 [SMILES: CC(C)[C@@H]1c2nc3ccc(S(C)(=O)=O)cc3n2CCN1c1ncc(CO)c(C(F)(F)F)n1] |

TABLE 1-continued

| Compound No. | Example No. | Structure |
|---|---|---|
| E25b | Example 25, isomer 2 | 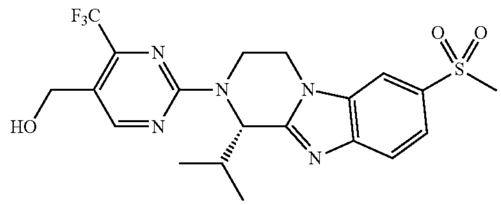 [SMILES: CC(C)[C@H]1c2nc3ccc(S(C)(=O)=O)cc3n2CCN1c1ncc(CO)c(C(F)(F)F)n1] |
| E26 | Example 26 | 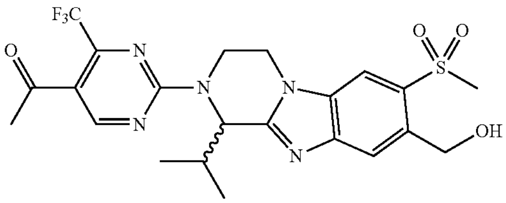 |
| E27a | Example 27, isomer 1 | 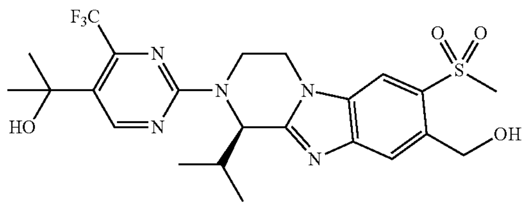 [SMILES: CC(C)[C@@H]1c2nc3cc(CO)c(S(C)(=O)=O)cc3n2CCN1c1ncc(C(C)(C)O)c(C(F)(F)F)n1] |
| E27b | Example 27, isomer 2 | 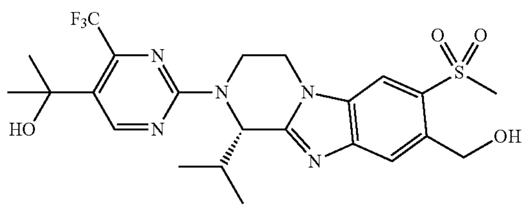 [SMILES: CC(C)[C@H]1c2nc3cc(CO)c(S(C)(=O)=O)cc3n2CCN1c1ncc(C(C)(C)O)c(C(F)(F)F)n1] |
| E28 | Example 28 | 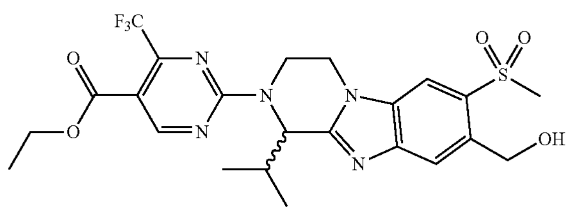 [SMILES: CCOC(=O)c1cnc(N2CCn3c(nc4cc(CO)c(S(C)(=O)=O)cc43)C2C(C)C)nc1C(F)(F)F] |
| E29a | Example 29, isomer 1 | 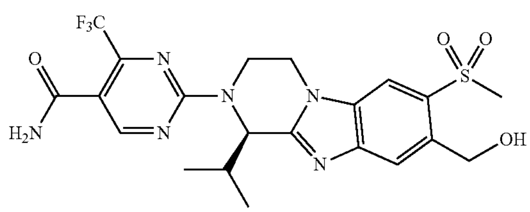 [SMILES: CC(C)[C@@H]1c2nc3cc(CO)c(S(C)(=O)=O)cc3n2CCN1c1ncc(C(N)=O)c(C(F)(F)F)n1] |
| E29b | Example 29, isomer 2 | 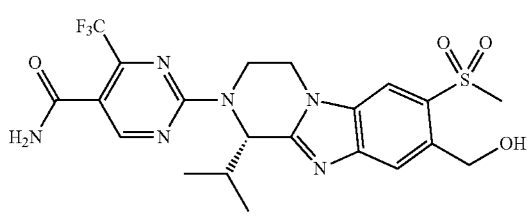 [SMILES: CC(C)[C@H]1c2nc3cc(CO)c(S(C)(=O)=O)cc3n2CCN1c1ncc(C(N)=O)c(C(F)(F)F)n1] |

TABLE 1-continued

| Compound No. | Example No. | Structure |
|---|---|---|
| E30 | Example 30 | 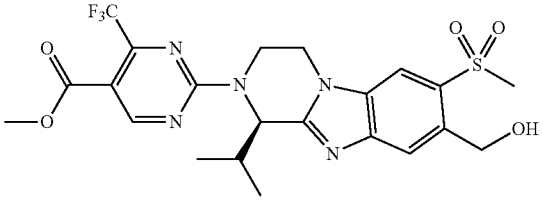 [SMILES: COC(=O)c1cnc(N2CCn3c(nc4cc(CO)c(S(C)(=O)=O)cc43)[C@H]2C(C)C)nc1C(F)(F)F] |

In another embodiment, an intermediate compound used in the preparation of the LXR modulators is represented by structural formula VIII, IX, or X or a salt thereof wherein the values for the variables are as defined for Formula Ia above.

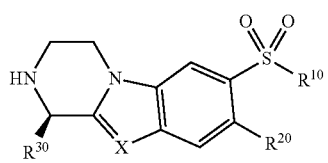

VIII

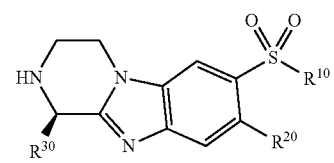

IX

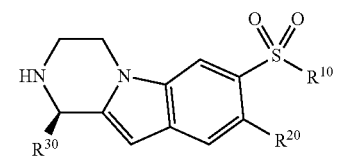

X

In a first alternative embodiment of an intermediate compound of formula VIII through X, $R^{10}$ is —$CH_3$. The values for the remaining variables are as defined for Formula Ia.

In a second alternative embodiment of an intermediate compound of formulas VIII through X, $R^{20}$ is —$CH_2OH$, —$CH_2O$(protecting group), —COOH, or —C(O)O(alkyl). The values for the remaining variables are as defined for Formula Ia or in the first alternative embodiment for formulas VIII through X.

In a third alternative embodiment of an intermediate compound of formulas VIII through X, $R^{30}$ is isopropyl. The values for the remaining variables are as defined for Formula Ia or the first or second alternative embodiment for formulas VIII through X.

In a fourth alternative embodiment of an intermediate compound of formulas VIII through X, $R^{20}$ is —$CH_2O$(TBDPS) or —C(O)$OCH_3$. The values for the remaining variables are as defined for Formula Ia or for the first or third alternative embodiment of any compound of formulas VIII through X.

In a fifth alternative embodiment of an intermediate compound of formulas VIII through X, an intermediate compound is selected from

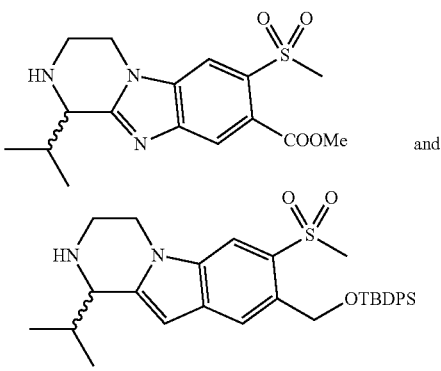

and or a salt thereof.

In a sixth alternative embodiment of an intermediate compound of formulas VIII through X, an intermediate compound is

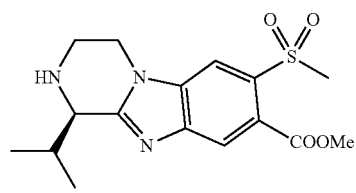 [SMILES: COC(=O)c1cc2nc3n(c2cc1S(C)(=O)=O)CCN[C@@H]3C(C)C]

or a salt thereof.

B. Definitions

Unless otherwise specified, the below terms used herein are defined as follows.

"Subject", "patient" and "mammal" are used interchangeably herein. In one embodiment, the subject is a non-human animal such as a non-human primate (e.g., a monkey, chimpanzee), a farm animal (e.g., a horse, cow, pig, chicken, or sheep), a laboratory animal (e.g., a rat or mouse), or a companion animal (e.g., dog, cat, guinea pig or rabbit). In a preferred embodiment, the subject is a human.

"Compound(s) of the invention" refers to compounds represented by Structural Formula I, II, III, IV, V, VI, VII; a compound depicted in Table 1; a compound named or depicted in the examples herein as the final compound(s) of the example; or a pharmaceutically acceptable salt thereof. "Compound(s) of the invention" also includes the neutral form of the compounds as depicted herein.

"Pharmaceutically acceptable" refers to a component that is, within the scope of sound medical judgment, suitable for use in contact with the tissues of the subject, such as humans and other mammals, without undue toxicity, irritation, allergic response and the like, and are commensurate with a reasonable benefit/risk ratio.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Lists of suitable salts are found in Remington's Pharmaceutical Sciences, 18th ed., Mack Publishing Company, Easton, Pa., 1990, p 1445, the disclosure of which is hereby incorporated by reference.

"Liver X receptors or LXRs" includes both the α and β subtypes of the liver X receptor. In one embodiment, the disclosed compounds selectively bind and upregulate the activity of the LXRβ subtype over the LXRα subtype. To "modulate" a receptor means that there is a change or alteration in the activity of a molecule of interest, e.g., the biological activity of liver X receptor. Modulation may be an upregulation (increase) or a downregulation (decrease) in the magnitude of a certain activity or function of the molecule of interest. Exemplary activities and functions of a molecule include, but are not limited to, binding characteristics, enzymatic activity, cell receptor activation, transcriptional activity, and signal transduction. In an embodiment, the compounds of the invention are LXR agonists that, for example, upregulate or downregulate genes which are transcriptional targets of LXR (i.e., "LXR target genes").

"Treat" or "treating" include both therapeutic and prophylactic treatments and mean to ameliorate, decrease, suppress, attenuate, diminish, arrest, or stabilize the development or progression of a disease (e.g., a disease or disorder delineated herein), lessen the severity of the disease or improve the symptoms associated with the disease.

"Disease" or "disorder" means any condition that is modulated or otherwise affected by LXR activity or in which LXR activity is implicated. The diseases or disorders include those which are associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

"Effective amount" is the quantity of the compound which is sufficient to treat (therapeutically or prophylactically) the target disorder or in which a beneficial clinical outcome is achieved when the compound is administered to a subject in a proper dosing regimen. Effective doses will also vary, as recognized by one of ordinary skill in the art, depending on the disease being treated, the severity of the disease, the route of administration, the sex, age and general health condition of the patient, excipient usage, the possibility of co-usage with other therapeutic treatments such as use of other agents and the judgment of the treating physician or other medical provider. For example, an effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. When a compound of the invention is administered to a subject with a disorder such as atherosclerosis, a "beneficial clinical outcome" includes reduction in the severity or number of symptoms associated with the disorder, lower cholesterol, or increase in the longevity of the subject compared with the absence of the treatment. The recommended dosages of agents currently used for the treatment of a disorder can be obtained from various references in the art including, but not limited to, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., each of which are incorporated herein by reference in its entirety. In certain embodiments, an effective amount of a compound of this invention is in the range of from 0.5 mg to 2000 mg, or from 0.5 mg to 1000 mg, or from 0.5 mg to 500 mg, or from 0.5 mg to 100 mg, or from 100 mg to 1000 mg, or from 20 mg to 2000 mg per treatment. Treatment typically is administered from one to three times daily.

"Halo" or "halogen" means chloro, bromo, fluoro, or iodo. In one embodiment, halo is fluoro.

"Alkyl" means a straight or branched hydrocarbon group having 1 to 15 carbon atoms in the chain. In one embodiment, alkyl groups have 1 to 12 carbon atoms in the chain. In another embodiment, alkyl groups have 1 to 6 carbon atoms. Exemplary alkyl groups include, but are not limited to, methyl, ethyl, n-propyl, isopropyl, n-butyl, tert-butyl, sec-butyl, n-pentyl, 3-pentyl, heptyl, octyl, nonyl, decyl, and dodecyl.

"Alkoxy" is an alkyl group which is attached to another moiety via an oxygen linker (—O(alkyl)). Non-limiting examples include methoxy, ethoxy, propoxy, and butoxy.

"Haloalkyl" or "halogenated alkyl" means an alkyl group in which one or more, including all, of the hydrogen radicals are replaced by a halo group, wherein each halo group is independently selected from —F, —Cl, —Br, and —I. For example, the term "halomethyl" or "halogenated methyl" means a methyl in which one to three hydrogen radical(s) have been replaced by a halo group. Representative haloalkyl groups include fluoromethyl, difluoromethyl, trifluoromethyl, bromomethyl, 1,2-dichloroethyl, 4-iodobutyl, 2-fluoropentyl, and the like. Other examples include groups such as but are not limited to —$CH_2CF_3$, —$CH(CH_2F)_2$, —$CH(CHF_2)_2$, —$CH(CF_3)_2$, —$CF(CH_3)_2$, —$CF_3$.

"Haloalkoxy" is a haloalkyl group which is attached to another moiety via an oxygen linker such as but are not limited to —$OCHCF_2$ or —$OCF_3$.

"Alkoxyalkyl" is an alkoxy group which is attached to another moiety via an alkyl linker. "Hydroxyalkyl" or "dihydroxyalkyl" is one or two hydroxy groups, respectively, which are attached to another moiety via an alkyl linker. Representative "hydroxyalkyl" or "dihydroxyalkyl" include —$CH_2OH$, —$CH(OH)(CH_2)(OH)$, —$C(OH)(CH_3)_2$, —$CH(OH)(CH_3)$, —$CH(OH)(CH_2)(CH_3)$, —$CH(OH)(CH_2)_2(CH_3)$, —$C(CH_3)_2(OH)$, and the like.

"Cycloalkyl" means a non-aromatic monocyclic ring system of 3 to 10 carbon atoms. In one embodiment, the cycloalkyl group has 3 to 6 carbon atoms. Exemplary cycloalkyl rings include cyclopropyl, cyclobutyl, cyclopentyl, and cyclohexyl.

"Cycloalkoxy" means a cycloalkyl group which is attached to another moiety via an oxygen linker (—O(cycloalkyl)).

"Monocyclic non-aromatic heterocycle" means a single saturated heterocyclic ring, typically having 3- to 10-members and more typically 3 to 7-members in the ring, wherein at least one atom in the ring is a heteroatom such as, for example, nitrogen, oxygen, sulfur, including sulfoxide and sulfone. A 3- to 4-membered monocyclic non-aromatic heterocycle can contain up to 2 heteroatoms; a 5-6 membered monocyclic heterocycle can contain up to 3 heteroatoms and a 7- to 10-membered monocyclic non-aromatic heterocycle can contain up to 4 heteroatoms. The monocyclic non-aromatic heterocycle may be attached to another group via any heteroatom or carbon atom of the monocyclic non-aromatic heterocycle. Representative monocyclic non-aromatic heterocycles include morpholinyl, thiomorpholinyl, pyrrolidinonyl, pyrrolidinyl, piperidinyl, piperazinyl, imidazolidinyl, pyrazolidinyl, oxazolidinyl, isothiazolidinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. In one embodiment, a monocyclic non-aromatic heterocycle is a heterocyclic ring of 4, 5, 6, or 7 members.

"Monocyclic heteroaromatic" comprises carbon atom ring members and one or more heteroatom ring members. Each heteroatom is independently selected from nitrogen, oxygen, and sulfur, including sulfoxide and sulfone. The point of attachment of a monocyclic heteroaromatic ring to another group may be at either a carbon atom or a heteroatom of the heteroaromatic. In one embodiment, the monocyclic heteroaromatic ring is selected from 5 to 8 membered monocyclic heteroaromatic rings. Representative monocyclic heteroaromatic groups include pyridyl, 1-oxo-pyridyl, furanyl, thienyl, pyrrolyl, oxazolyl, imidazolyl, thiazolyl, isoxazolyl, pyrazolyl, isothiazolyl, pyridazinyl, pyrimidinyl, pyrazinyl, a triazinyl, triazolyl, thiadiazolyl, and tetrazolyl.

A protecting group is a group which is bonded to a reactive functional group in a compound to convert the reactive functional group to another, non-reactive group to allow, for example, reaction(s) at another part of the molecule without interference from the reactive functional group. Once the reaction(s) at the other part of the molecule have been completed, the protecting groups is removed to regenerate the original reactive functional group. Protecting groups for an hydroxy group (—OH) and reactions and conditions for protecting and deprotecting the hydroxy group are well known in the art and are disclosed, for example, in Greene and Wuts, "Protective Groups in Organic Synthesis", John Wiley & Sons (2007), Chapter 2 and references cited therein. For example, a protecting group may protect a hydroxy group as an ether. Such protecting groups include, but are not limited to methyl, methoxymethyl, methylthiomethyl, (phenyldimethylsilyl)methoxymethyl, benzyloxymethyl, p-methoxybenzyloxymethyl, [3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, O-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl, S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahyrdo-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1,-dianisyl-2,2,2,-trichloroethyl, 1,1,1,3,3,3-hexafluoro-2-phenylisopropyl, 1-(2-cyanoethoxyl)ethyl, 2-trimethylsilylethyl, 2-(benzylthio)ethyl, 2-(phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluoros benzyl, 4-fluorousalkoxybenzyl, trimethylsilylxylyl, p-phenylbenzyl, 2-phenyl-2-propyl(cumyl), p-acylaminobenzyl, p-azidobenzyl, 4-azido-3-chlorobenzyl, 2- and 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2- and 4-picolyl, 3-methyl-2-picolyl N-oxide, 2-quinolinylmethyl, 6-methoxy-2-(4-methylpheny)-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyl)phenyldiphenylmethyl, 4,4',4"-tris(4,5-dichlorophthalimidophenyl)methyl, 4,4',4"-tris(levulinoyloxyphenyl)methyl, 4,4',4"tris(benzoyloxyphenyl)methyl, 4,4'-dimethoxy-3"-[N-(imidazolylmethyl)trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, 4,5-bis(ethoxycarbonyl[1,3]-dioxolan-2-yl, benzisothiazolyl S,S-dioxido, trimethylsilyl, triethylsilyl, triisopropylsilyl, dimethylisopropylsiyl, diethylisopropylsilyl, dimethylthexylsilyl, 2-norbornyldimethylsily, t-butyldimethylsilyl, t-butyldiphenylsilyl (TBDPS), tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, sisyl, (2-hydroxystyryl)dimethylsilyl, (2-hydroxystyryl)diisopropylsily, t-butylmethoxyphenylsilyl, t-butoxydiphenylsilyl, 1,1,3,3-tetraisopropyl-3-[2-(triphenylmethoxy)ethoxy]disiloxane-1-yl, fluorous silyl.

Alternatively, suitable protecting groups protect the hydroxy group as esters, for example, formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, p-P-phenylacetate, diphenylacetate, 3-phenylpropionate, bisfluorous chain type propanoyl (Bfp-OR), 4-pentenoate, 4-oxopentanoate (levulinate), 4,4-(ethylenedithio)pentanoate, 5-[3-Bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate (mesitoate), 4-bromobenzoate, 2,5- difluorobenzoate, p-nitrobenzoate, picolinate, nicotinate, 2-(azidomethyl)benzoate, 4-azidobutyrate, (2-azidomethyl) phenylacetate, 2-{[(tritylthio)oxy]methyl}benzoate, 2-{[(4-methoxytritylthio)oxy]methyl}benzoate,2-{[methyl(tritylthio)amino]methyl}benzoate, 2-{{[(4-methoxytrityl)thio] methylamino}-methyl}benzoate, 2-(allyloxy)phenylacetate, 2-(prenyloxymethyl)benzoate, 6-(levulinyloxymethyl)-3-methoxy-2- and 4-nitrobenzoate, 4-benzyloxybutyrate, 4-trialkylsiloxybutrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-methylthiomethoxy)butyrate, 2-methylthiomethoxymethyl)benzoate, 2-(chloroacetoxymethyl)benzoate, 2[(2-chloroacetoxy)ethyl]benzoate, 2-[2-(benzyloxy)ethyl]benzoate, 2-[2-(4-methoxybenzyloxyl) ethyl]benzoate, 2,6-dichloro-4-methylphenoxyacetate, 2,6-dichloro-4-(1,1,3,3-tetramethylbutyl)phenoxyacetate, 2,4-bis(1,1-imethylpropyl)phenoxyacetate, chlorodiphenylacetate, isobutyrate, monosuccinoate, (E)-2-methyl-2-butenoate tigloate), o-(methoxycarbonyl)benzoate, p-P-benzoate, α-naphthoate, nitrate, alkyl N,N,N',N'-tetramethylphosphorodiamidate, 2-chlorobenzoate, as sulfonates, sulfenates and sulfinates such as sulfate, allylsulfonate, ethanesulfonate (mesylate), benzylsulfonate, tosylate, 2-[(4-nitrophenyl)ethyl]sulfonate, 2-trifluoromethylsulfonate, 4-monomethoxytritylsulfenate, alkyl 2,4-initrophenylsulfenate, 2,2,5,5-tetramethylpyrrolidin-3-one-1-sulfinate, borate, dimethylphosphinothioyl, as carbonates such as alkyl methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(-methoxytrityl)sulfenyl]oxy]tetraydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxyl-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-yl-methyl carbonate, 2-dansylethyl carbonate, 2-(4-nitrophenyl)ethyl, 2-(2,4-nitrophenyl)ethyl, 2-(2-nitrophenyl)propyl, 2-(3,4-methylenedioxy-6-nitrophenylpropyl, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, S-benzyl thiocarbonate, and carbamates such as dimethylthiocarbamate, N-phenylcarbamate, and N-methyl-N-(o-nitrophenyl) carbamate.

C. Pharmaceutical Compositions, Formulations and Dosages

In one embodiment, provided herein is a pharmaceutical composition comprising a compound of the invention and a pharmaceutically acceptable carrier or diluent.

In the pharmaceutical compositions of the invention, the compound of the invention is present in an effective amount. The interrelationship of dosages for animals and humans (based on milligrams per meter squared of body surface) is described in Freireich et al., Cancer Chemother. Rep, 1966, 50: 219. Body surface area may be determined approximately from height and weight of the patient. See, e.g., Scientific Tables, Geigy Pharmaceuticals, Ardsley, N.Y., 1970, 537.

The LXR modulators herein (e.g., compound(s) of the invention) can be formulated as pharmaceutical compositions and administered to a subject, such as a human, in a variety of forms adapted to the chosen route of administration. Typical routes of administering such pharmaceutical compositions include, without limitation, oral, topical, buccal, transdermal, inhalation, parenteral, sublingual, rectal, vaginal, and intranasal. The term parenteral as used herein includes subcutaneous injections, intravenous, intramuscular, intrathecal, intrasternal injection or infusion techniques. Methods of formulating pharmaceutical compositions are well known in the art, for example, as disclosed in "Remington: The Science and Practice of Pharmacy," University of the Sciences in Philadelphia, ed., 21st edition, 2005, Lippincott, Williams & Wilkins, Philadelphia, Pa. Each of the LXR modulators may be used alone or in combination as a part of a pharmaceutical composition of the invention.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like.

Suitable tablets may be obtained, for example, by mixing one or more compounds of the invention with known excipients, for example inert diluents, carriers, disintegrants, adjuvants, surfactants, binders and/or lubricants. The tablets may also consist of several layers.

The compounds of the invention can be suitably formulated into pharmaceutical compositions for administration to a subject. The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the invention may be incorporated with excipient and used in the form of ingestible tablets, buccal tablets, troches, capsules, elixirs, suspensions, syrups, wafers, and the like.

Typically for parenteral administration, solutions of a compound of the invention can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the invention for the extemporaneous preparation of sterile injectable solutions or dispersions.

For nasal administration, the compounds of the invention can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the invention can be formulated with a carrier such as sugar, acacia, tragacanth, or gelatin and glycerine, as tablets, lozenges or pastilles.

For rectal administration, the compounds of the invention can be formulated in the form of suppositories containing a conventional suppository base such as cocoa butter.

Topical and/or local administration of the compounds of the invention can be achieved in a variety of ways including but not limited to ointments, lotions, pastes, creams, gels, powders, drops, sprays, solutions, inhalants, patches, suppositories, retention enemas, chewable or suckable tablets or pellets and aerosols. Topical and/or local administration may also involve the use of transdermal administration such as transdermal patches or iontophoresis devices. For topical and/or local administration, the compounds of the invention can be formulated as ointments, creams, milks, salves, powders, impregnated pads, syndets, solutions, gels, sprays, foams, suspensions, lotions, sticks, shampoos or washing bases. Compounds of the invention may also be administered in the form of suspensions of lipid or polymer vesicles or nanospheres or microspheres or polymer patches and hydrogels for controlled release.

D. Methods of Treatment and Use of the LXR Modulators

Provided herein is a method of treating a subject with a disease or disorder that is treatable by modulation of LXR. In one embodiment, LXR is modulated by upregulating LXR activity. The method comprises administering an effective amount of the compound of the invention. Moreover, provided herein is the use of a compound of the invention for the manufacture of a medicament for treating a subject with a disease or disorder that is treatable by upregulating LXR activity in a subject in need thereof.

The methods provided herein may be useful for disorders treatable with LXR modulation, in particular LXR agonism.

Compounds of the invention are useful for the treatment or prevention of diseases or disorders associated with altered cholesterol transport, reverse cholesterol transport, fatty acid metabolism, cholesterol absorption, cholesterol re-absorption, cholesterol secretion, cholesterol excretion, or cholesterol metabolism. Representative diseases or disorders include, but are not limited to, a lipid disorder; cancer, particularly hormone-dependent cancers, including ovarian, breast and prostate cancer; acneiform skin condition; skin inflammatory disease; immunological disorder; condition characterized by a perturbed epidermal barrier function; condition of disturbed differentiation or excess proliferation of the epidermis or mucous membrane; cardiovascular disease; reproductive tract disorders; optic nerve and retinal pathology; degenerative neuropathy occurring in a disease; autoimmune disease; traumatic damage to the central or peripheral nervous system; neurodegenerative disease; or a degenerative process due to aging; diseases or disorders of the kidney; and osteoporosis and related diseases.

In another embodiment, the disease or disorder is hyperlipidemia, hypercholesterolemia, hyperlipoproteinemia, hypertriglyceridemia, lipodystrophy, hepatic steatosis, non-alcoholic steatohepatitis (NASH), nonalcoholic fatty liver disease (NAFLD), hyperglycemia, insulin resistance, diabetes mellitus, dyslipidemia, atherosclerosis, gallstone disease, acne vulgaris, dermatitis (including but not limited to, psoriasis, contact dermatitis, atopic dermatitis, and eczema), skin wounds, skin aging, photoaging, wrinkling, diabetes, Niemann-Pick disease type C, Parkinson's disease, Alzheimer's disease, inflammation, xanthoma, obesity, metabolic syndrome, syndrome X, stroke, peripheral occlusive disease, memory loss, diabetic neuropathies, proteinuria, glomerulopathies (including but not limited to, diabetic nephropathy, hypertensive nephropathy, IGA nephropathy, focal segmental glomerulosclerosis), hyperphosphatemia, associated cardiovascular complications of hyperphosphatemia, cancer, multiple sclerosis or osteoporosis.

In another embodiment, the disease or disorder is common acne; comedones; polymorphs; rosacea; nodulocystic acne; acne conglobate; senile acne; secondary acne, including but not limited to solar, medicinal and occupational acne; ichthyosis; ichthyosiform conditions; Darier's disease; palmoplantar keratoderma; leukoplakia; leukoplakiform conditions; cutaneous or mucous (oral) lichen; dermatological conditions or afflictions with an inflammatory immunoallergic component, with or without a cellular proliferation disorder, including but not limited to cutaneous psoriasis, mucous psoriasis, ungual psoriasis, psoriatic rheumatism, cutaneous atopy, including eczema, respiratory atopy and gingival hypertrophy; benign or malignant dermal or epidermal proliferations, of viral or non-viral origin, including but not limited to common warts, flat warts, epidermodysplasia verruciformis, oral or florid papillomatoses, and T lymphoma or cutaneous T-cell lymphoma; proliferations that may be induced by ultraviolet light, including but not limited to basocellular epithelioma and spinocellular epithelioma; precancerous skin lesions, including but not limited to keratoacanthomas; immune dermatitides, including but not limited to lupus erythematosus; bullous immune diseases; collagen diseases, including but not limited to scleroderma; dermatological or systemic conditions or afflictions with an immunological component; skin disorders due to exposure to UV radiation; photo-induced or chronological aging of the skin; actinic pigmentations; keratosis; pathology associated with chronological or actinic aging, including but not limited to xerosis; sebaceous function disorders, including but not limited to hyperseborrhoea of acne, simple seborrhoea and seborrhoeic dermatitis; cicatrization disorders, including but not limited to stretch marks; pigmentation disorders, including but not limited to hyperpigmentation, melasma, hypopigmentation, and vitiligo; and alopecia, including but not limited to chemotherapy-associated alopecia and radiation-associated alopecia.

In an embodiment, the disease or disorder is hypercholesterolemia, atherosclerosis or dyslipidemia. In another embodiment, the disease or disorder is atherosclerosis or dyslipidemia. In yet another embodiment, the disease or disorder is atherosclerosis, Alzheimer's disease or dermatitis.

The present invention also provides a method for increasing reverse cholesterol transport and/or for inhibiting the progression of or promoting the regression of atherosclerosis.

The present invention also provides a method of treating diseases or disorders associated with a need for increasing high density lipoprotein (HDL)-cholesterol levels comprising the administration of an effective amount of a compound of the invention to a mammal (particularly a human) in need thereof.

The present invention also provides a method of treating a disease or disorder associated with a need for decreasing low density lipoprotein (LDL)-cholesterol levels comprising the administration of an effective amount of a compound of the invention to a mammal (particularly a human) in need thereof.

Additionally, provided herein is a method of increasing the expression of an ATP-Binding Cassette protein in a subject's cells, thereby increasing reverse cholesterol transport in a subject using the compounds of the invention and compositions provided herein.

Standard physiological, pharmacological and biochemical procedures are known to the art and are available for evaluating compounds of the present invention for the ability to modulate LXR activity. Such assays include, for example, binding assays, fluorescence polarization assays, FRET based co-activator recruitment assays, and cell-based co-transfection assays. Compounds of the present invention can be evaluated for their ability to modulate the expression of genes known to be modulated by LXR. Established animal models can be used to study the profiles of compounds of the present invention in relation to parameters directly relevant to diseases or disorders, including atherosclerosis, Alzheimer's disease, and skin conditions. Thus, compounds of the present invention can be tested in vivo in animal models by a variety of routes of administration, for example, oral gavage. Typically, in vivo compound exposure can be examined in plasma and in tissues of interest. LXR activity (as detected by gene expression of LXR-responsive genes) can be examined in whole blood and tissues of interest. Lipids can be quantified in the plasma and the liver.

In particular, compounds of the present invention can be tested for their activity on ATP-Binding Cassette (ABC) cholesterol transporters, such as ABCA1 and ABCG1, and on lipogenic markers, such as SREBP1c at the gene and protein expression level. The functional consequences of ABC transporter induction can be examined in cellular models for cholesterol efflux and in animal models for the reverse cholesterol pathway and atherosclerosis. Lipogenic markers can be examined in animal models by measuring plasma and liver triglyceride levels.

The compounds of the present invention can be used alone (i.e., as a monotherapy) or in combination with one or more other therapeutic agent effective for treating any of the above indications. The pharmaceutical compositions can comprise the disclosed compounds alone as the only pharmaceutically active agent or can comprise one or more additional pharmaceutically active agents.

The present invention also provides combination therapy for treating or ameliorating a disease or a disorder described herein. In some embodiments, the combination therapy comprises administering at least one compound represented by Structural Formula I, II, III, IV, V, or VI in combination with one or more agents for treating or ameliorating a disease or a disorder described herein. In some embodiments, the combination therapy comprises administering at least one compound represented by Structural Formula I, II, III, IV, V, or VI in combination with one or more agents for the treatment of diseases including hyperlipidemia, hypercholesterolemia, hyperlipoproteinemia, hypertriglyceridemia, lipodystrophy, hepatic steatosis, NASH, NAFLD, hyperglycemia, insulin resistance, diabetes mellitus, dyslipidemia, atherosclerosis, gallstone disease, acne vulgaris, dermatitis (including but not limited to, psoriasis, contact dermatitis, atopic dermatitis, and eczema), skin wounds, skin aging, photoaging, wrinkling, diabetes, Niemann-Pick disease type C, Parkinson's disease, Alzheimer's disease, inflammation, xanthoma, obesity, metabolic syndrome, syndrome X, stroke, peripheral occlusive disease, memory loss, diabetic neuropathies, proteinuria, glomerulopathies (including but not limited to, diabetic nephropathy, hypertensive nephropathy, IGA nephropathy, focal segmental glomerulosclerosis), hyperphosphatemia, associated cardiovascular complications of hyperphosphatemia, cancer, multiple sclerosis or osteoporosis.

In some embodiments, the compounds of the invention are used in combination with one or more additional agents for the treatment of diabetes, dyslipidemia, cardiovascular disease, hypertension, or obesity. Agents for the treatment of diabetes include insulins, such as Humulin® (Eli Lilly), Lantus® (Sanofi Aventis), Novolin® (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophage®/Glucophage XR® (metformin HCl, Bristol Myers Squibb) and Glumetza® (metformin HCl extended release tablets, Depomed); thiazolidinediones; amylin analogs, GLP-1 analogs or agonists (including Byetta® (exenatide, Amylin/Eli Lilly) and Victoza® (recombinant liraglutide, Novo Nordisk)); DPP-IV inhibitors including Tradjenta™ (Eli Lilly/Boehringer Ingelheim), Januvia® (Merck), Galvus® (Novartis), and Onglyza® (Bristol-Myers Squibb/AstraZeneca); PTB-1 B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists. Agents for the treatment of obesity include orlistat, phentermine, sibutramine and rimonabant.

An embodiment of the invention includes administering an LXR modulator compound of the invention or composition thereof in a combination therapy with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

In some embodiments, the combination therapy comprises administering at least one compound of the invention in combination with one or more compound selected from the group of, for example, beta secretase (BACE1) inhibitors; gamma-secretase inhibitors; amyloid aggregation inhibitors (e.g., ELND-005); directly or indirectly acting neuroprotective and/or disease-modifying substances; anti-oxidants (e.g., vitamin E or ginkolide); anti-inflammatory substances (e.g., Cox inhibitors, NSAIDs); HMG-CoA reductase inhibitors (statins); acetylcholinesterase inhibitors (e.g., donepezil, rivastigmine, tacrine, galantamine, memantine; tacrine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies for the treatment of a disease or disorder disclosed herein.

Combination therapy includes co-administration of a compound of the invention and one or more other agent, sequential administration of a compound of the invention and one or more other agent, administration of a composition containing a compound of the invention and one or more other agent, or simultaneous administration of separate compositions containing a compound of the invention and one or more other agent.

E. Exemplary Synthesis

General Description of Synthetic Methods

The compounds of the present invention can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those of ordinary skill in this art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below X, $R^1$, $R^2$, $R^3$, $R^4$, $R^5$ and $R^6$ have the meanings indicated above unless otherwise indicated. The abbreviations used in these experimental details are listed below and additional ones should be known to a person skilled in the art of synthesis. In addition one can refer to the following references for suitable methods of synthesis as described in March, *Advanced Organic Chemistry*, 3rd edition, John Wiley & Sons, 1985, Greene and Wuts, *Protective Groups in Organic Synthesis*, $2^{nd}$ edition, John Wiley & Sons, 1991, and Richard Larock, *Comprehensive Organic Transformations*, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

LC-MS data were obtained by utilizing the following chromatographic conditions:

| Method 1 (10-80, 2 min) | |
| --- | --- |
| Column | Xtimate ™ C18 2.1*30 mm, 3 μm |
| Mobile Phase | A: water (4 L) + TFA (1.5 mL)<br>B: acetonitrile (4 L) + TFA (0.75 mL) |

| TIME (min) | A % | B % |
| --- | --- | --- |
| 0 | 90 | 10 |
| 0.9 | 20 | 80 |
| 1.5 | 20 | 80 |
| 1.51 | 90 | 10 |
| 2 | 90 | 10 |

| | |
| --- | --- |
| Flow Rate | 1.2 mL/min |
| wavelength | UV 220 nm |
| Oven Temp | 50° C. |
| MS ionization | ESI |

| Method 2 (30-90, 2 min) | |
| --- | --- |
| Column | Xtimate ™ C18 2.1*30 mm, 3 μm |
| Mobile Phase | A: water (4 L) + TFA (1.5 mL)<br>B: acetonitrile (4 L) + TFA (0.75 mL) |

| TIME (min) | A % | B % |
| --- | --- | --- |
| 0 | 70 | 30 |
| 0.9 | 10 | 90 |
| 1.5 | 10 | 90 |
| 1.51 | 70 | 30 |
| 2 | 70 | 30 |

-continued

Method 2 (30-90, 2 min)

| | |
|---|---|
| Flow Rate | 1.2 mL/min |
| wavelength | UV 220 nm |
| Oven Temp | 50° C. |
| MS ionization | ESI |

Method 3 (0-60, 2 min)

| Column | Xtimate ™ C18 2.1*30 mm, 3 µm | | |
|---|---|---|---|
| Mobile Phase | A: water (4 L) + TFA (1.5 mL) | | |
| | B: acetonitrile (4 L) + TFA (0.75 mL) | | |
| | TIME (min) | A % | B % |
| | 0 | 100 | 0 |
| | 0.9 | 40 | 60 |
| | 1.5 | 40 | 60 |
| | 1.51 | 100 | 0 |
| | 2 | 100 | 0 |
| Flow Rate | 1.2 mL/min | | |
| wavelength | UV 220 nm | | |
| Oven Temp | 50° C. | | |
| MS ionization | ESI | | |

Method 4:

HPLC System: Waters ACQUITY; Column: Waters ACQUITY CSH™ C18 1.7 µM Guard column: Waters Assy. Frit, 0.2 µM, 2.1 mm; Column tem: 40° C. Mobile Phase: A: TFA: Water (1:1000, v:v) Mobile phase B: TFA: ACN (1:1000, v:v); Flow Rate: 0.65 mL/min; Injection Volume: 2 µL; Acquisition time: approximately 1.5 minute.

Gradient Program:

| Time (min) | B % |
|---|---|
| 0 | 10 |
| 0.8 | 90 |
| 1.20 | 90 |
| 1.21 | 10 |

Mass Spectrometer Parameters

Mass Spectrometer: Waters SQD; Ionization: Positive Electrospray Ionization (ESI); Mode Scan (100-1400 m/z in every 0.2 second); ES Capillary Voltage: 3.5 kv; ES Cone Voltage: 25 v Source Temperature: 120° C.; Disolvation Temperature: 500° C.; Desolvation Gas Flow: Nitrogen Setting 650 (L/hr); Cone Gas Flow: Nitrogen Setting 50 (L/hr)

SFC separation of compounds of the invention were carried out under the following methods.

Method A:

Instrument: Thar SFC 80; Column: AD 250 mm*30 mm, 5 µm; Mobile phase: A: Supercritical $CO_2$, B: IPA (0.05% DEA), A: B=80:20 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

Method B:

Instrument: SFC MG2; Column: OJ 250 mm*30 mm, 5 µm; Mobile phase: A: Supercritical $CO_2$, B: MeOH (0.05% DEA), A:B=90:10 at 70 ml/min; Column Temp: 38° C.; Nozzle Pressure: 100 Bar Nozzle Temp: 60° C.; Evaporator Temp: 20° C.; Trimmer Temp: 25° C.; Wavelength: 220 nm Analytical Chiral HPLC The chiral purity of compounds of the invention was determined by analytical chiral HPLC, which was carried out using Chiralcel® or Chiralpak® columns, using $CO_2$, together with from 5% to 40% methanol, ethanol or isopropanol, containing 0.05% DEA, as eluents.

| Method | Detailed information |
|---|---|
| OJ-H_3_5_40_2.35ML | Column: Chiralcel ® OJ-H 250 × 4.6 mm I.D., 5 µm Mobile phase: methanol (0.05% DEA) in $CO_2$ from 5% to 40% Flow rate: 2.35 mL/min Wavelength: 220 nm |
| OJ-H_3_5_40_2.5ML | Column: Chiralcel ® OJ-H 250 × 4.6 mm I.D., 5 µm Mobile phase: methanol (0.05% DEA) in $CO_2$ from 5% to 40% Flow rate: 2.5 mL/min Wavelength: 220 nm |
| AS-H_3_5_40_2.35ML | Column: Chiralpak ® AS-H 250 × 4.6 mm I.D., 5 µm Mobile phase: methanol (0.05% DEA) in $CO_2$ from 5% to 40% Flow rate: 2.35 mL/min Wavelength: 220 nm |
| AS-H_4_5_40_2.5ML | Column: Chiralpak ® AS-H 250 × 4.6 mm I.D., 5 µm Mobile phase: iso-propanol (0.05% DEA) in CO2 from 5% to 40% Flow rate: 2.5 mL/min Wavelength: 220 nm |
| AS-H_5_5_40_2.35ML | Column: Chiralpak ® AS-H 250 × 4.6 mm I.D., 5 µm Mobile phase: ethanol (0.05% DEA) in $CO_2$ from 5% to 40% Flow rate: 2.35 mL/min Wavelength: 220 nm |
| AS-H_3_5_40_2.5ML | Column: Chiralpak ® AS-H 250 × 4.6 mm I.D., 5 µm Mobile phase: methanol (0.05% DEA) in CO2 from 5% to 40% Flow rate: 2.5 mL/min Wavelength: 220 nm |
| AD-H_3_5_40_2.35ML | Column: Chiralpak ® AD-H 250 × 4.6 mm I.D., 5 µm Mobile phase: methanol (0.05% DEA) in $CO_2$ from 5% to 40% Flow rate: 2.35 mL/min Wavelength: 220 nm |
| AD-H_5_5_40_2.35ML | Column: Chiralpak ® AD-H 250 × 4.6 mm I.D., 5 µm Mobile phase: ethanol (0.05% DEA) in $CO_2$ from 5% to 40% Flow rate: 2.35 mL/min Wavelength: 220 nm |
| OD-3_3_5_40_2.5ML | Column: Chiralcel ® OD-3 150 × 4.6 mm I.D., 3 µm Mobile phase: methanol (0.05% DEA) in $CO_2$ from 5% to 40% Flow rate: 2.5 mL/min Wavelength: 220 nm |
| OD-3_4_5_40_2.5ML | Column: Chiralcel ® OD-3 150 × 4.6 mm I.D., 3 µm Mobile phase: iso-propanol (0.05% DEA) in $CO_2$ from 5% to 40% Flow rate: 2.5 mL/min Wavelength: 220 nm |

| Method | Detailed information |
| --- | --- |
| OD-3_5_5_40_2.5ML | Column: Chiralcel ® OD-3 150 × 4.6 mm I.D., 3 μm Mobile phase: ethanol (0.05% DEA) in $CO_2$ from 5% to 40% Flow rate: 2.5 mL/min Wavelength: 220 nm |
| AD-3_3_5_40_2.5ML | Column: Chiralpak ® AD-3 150 × 4.6 mm I.D., 3 μm Mobile phase: methanol (0.05% DEA) in $CO_2$ from 5% to 40% Flow rate: 2.5 mL/min Wavelength: 220 nm |
| AD-3_4_5_40_2.5ML | Column: Chiralpak ® AD-3 150 × 4.6 mm I.D., 3 μm Mobile phase: iso-propanol (0.05% DEA) in $CO_2$ from 5% to 40% Flow rate: 2.5 mL/min Wavelength: 220 nm |
| AD-3_5_5_40_2.5ML | Column: Chiralpak ® AD-3 150 × 4.6 mm I.D., 3 μm Mobile phase: ethanol (0.05% DEA) in $CO_2$ from 5% to 40% Flow rate: 2.5 mL/min Wavelength: 220 nm |
| OD-H_3_5_40_2.35ML | Column: Chiralcel ® OD-H 250 × 4.6 mm I.D., 5 μm Mobile phase: methanol (0.05% DEA) in $CO_2$ from 5% to 40% Flow rate: 2.35 mL/min Wavelength: 220 nm |
| OD-H_5_5_40_2.35ML | Column: Chiralcel ® OD-H 250 × 4.6 mm I.D., 5 μm Mobile phase: ethanol (0.05% DEA) in $CO_2$ from 5% to 40% Flow rate: 2.35 mL/min Wavelength: 220 nm |

The invention is illustrated by way of the following examples, in which the following abbreviations may be employed:

| Abbreviation | Meaning |
| --- | --- |
| ACN, MeCN, $CH_3CN$ | acetonitrile |
| aq. | aqueous |
| Boc | tert-butoxy carbonyl or t-butoxy carbonyl |
| brine | saturated aqueous NaCl |
| Cbz | benzyloxy carbonyl |
| $CeCl_3$ | ceric chloride |
| $Cs_2CO_3$ | cesium carbonate |
| CuI | cuprous iodide |
| DCM or $CH_2Cl_2$ | methylene chloride |
| DIEA | diisopropyl ethyl amine |
| DMF | dimethyl formamide |
| DMS/Me2S | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |
| $Et_2O$ | ethyl ether |
| $Et_3SiH$ | triethylsilane |
| $Et_3N$ | triethylamine |
| EtOAc, EA, AcOEt | ethyl acetate |
| EtOH | ethanol |
| $FeCl_3$ | ferric chloride |
| h, hr | hour(s) |
| HATU | O-(7-azabenzotriazol-1-yl)-N,N,N',N'-tetramethyluronium-hexafluorophosphate |
| HBTU | O-Benzotriazole-1-yl-N,N,N',N'-tetramethyluronium-hexafluorophosphate |
| HCl | hydrochloric acid |
| $H_2O$ | water |
| $H_2O_2$ | hydrogen peroxide |
| HPLC | high performance liquid chromatography |
| i-BuOCOCl | iso-butoxycarbonyl chloride |
| ICl | iodochloride |
| $K_2CO_3$ | potassium carbonate |
| $K_3PO_4$ | tripotassium phosphate |
| LC-MS | liquid chromatography-mass spectrometry |
| LDA | lithium diiisopropylamide |
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| $Mg_2SO_4$ | magnesium sulfate (anhydrous) |
| min | minute(s) |
| mL | milliliters |
| mmol | millimoles |
| mp, m.p. | melting point |
| MS | mass spectrometry |
| MW | microwave |
| $NaBH_4$ | sodium borohydride |
| $NaBH_3CN$ | sodium cyanoborohydride |
| NaH | sodium hydride |
| $NaHCO_3$ | sodium bicarbonate |
| NaOH | sodium hydroxide |
| NaOMe | sodium methoxide |
| $Na_2S_2O_3$ | sodium thiosulfate |
| $Na_2S_2O_5$ | sodium dithionate |
| $Na_2SO_4$ | sodium sulfate |
| $NH_4OH$ | ammonium hydroxide |
| $(NH_4)_2CO_3$ | ammonium carbonate |
| $NH_4Cl$ | ammonium chloride |
| $Na_2CO_3$ | sodium carbonate |
| $NaHCO_3$ | sodium bicarbonate |
| NaH | sodium hydride |
| w-BuLi | n-butyllithium |
| NMM | N-methyl-morpholine |
| NMP | N-methyl-pyrrolidin-2-one |
| OTf | trifluoromethanesulfonate |
| OTs | tosylate |
| $PdCl_2dppf$ | [1,1-bis(diphenylphosphino)ferrocene]dichloropalladium(ii) |
| $Pd_2(dba)3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| $Ti(OEt)_4$ | titanium tetra ethoxide |
| Zn | zinc |
| $Zn(CN)_2$ | zinc cyanide |

In the first process, a compound of Formula I can be prepared by $S_NAr$ or palladium catalyzed reactions of reagents 1, where $G^1$ is Cl, Br, I, OTf or OTs, with intermediates of Formula 2. Reagents 1 are either commercially available or can be prepared readily from commercially available precursors based on literature precedents.

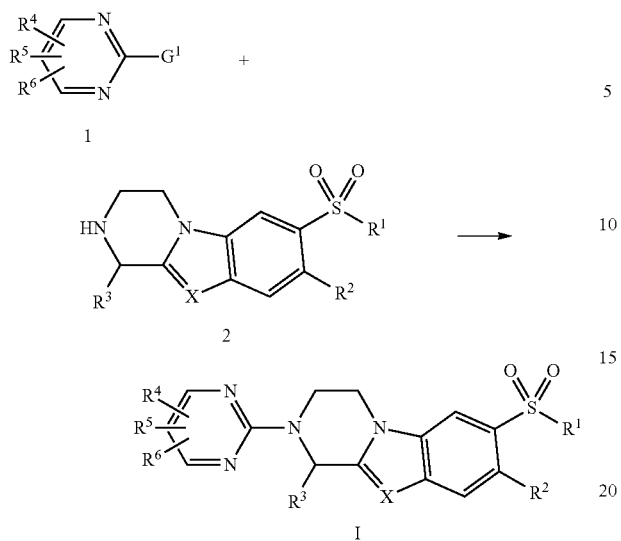

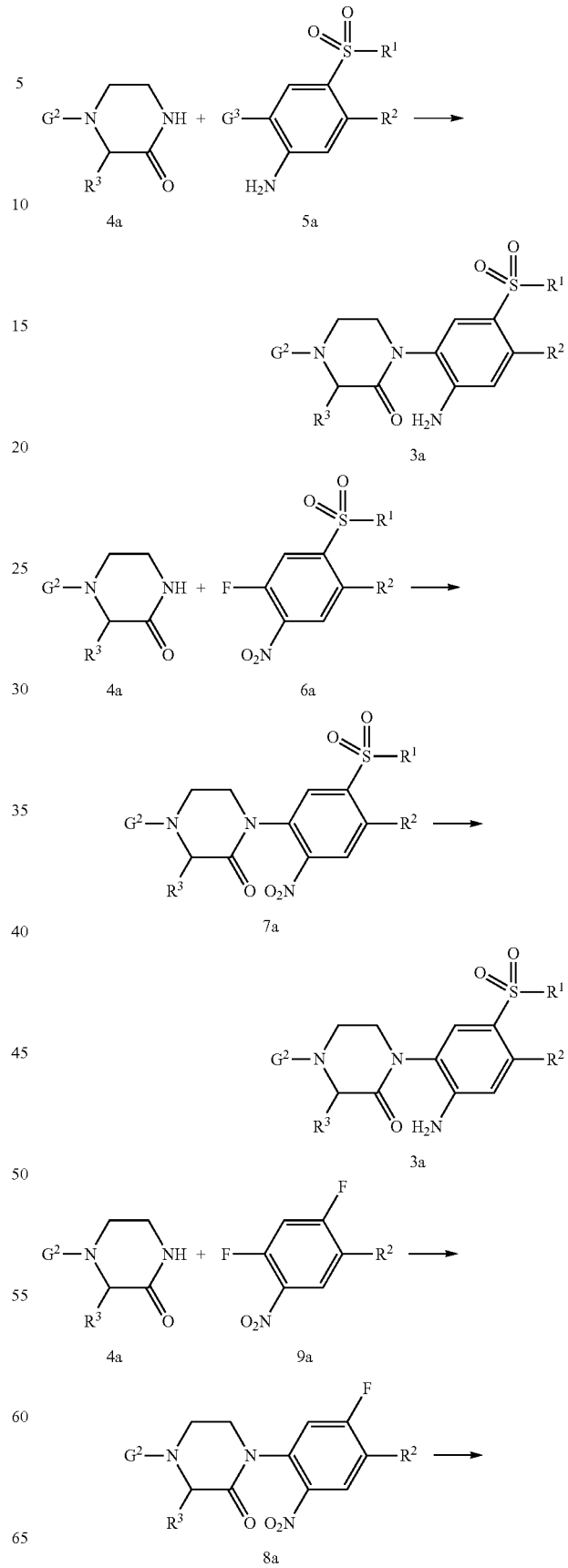

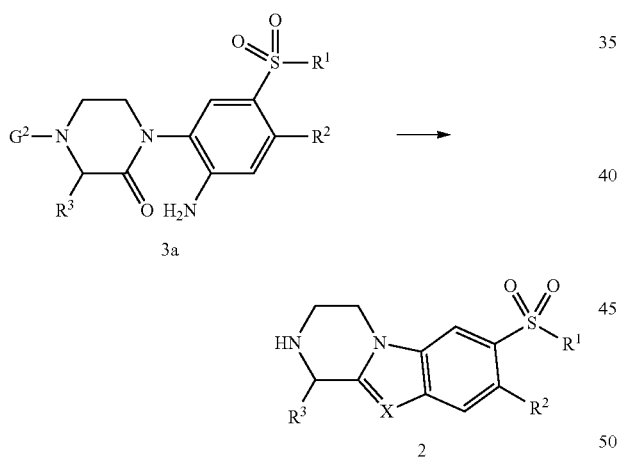

Intermediates 2 can be prepared by one of the several different methods depicted below.

When X=N, intermediates of Formula 2 can be prepared by cyclization of intermediates of Formula 3a followed by removal of $G^2$ when $G^2$ is not hydrogen. $G^2$ is an amine protecting group, such as Boc, Cbz and trifluoroacetamide, etc.

Intermediates of Formula 3a can be prepared by one of the two methods: 1) copper mediated coupling of piperazinone 4a and aniline 5a, where $G^3$ is Br, I, Cl or OTf; 2) $S_NAr$ reaction between 4a and fluorinated nitrobenzene 6a to give intermediate of Formula 7a followed by reduction of the nitro group. The intermediate 7a can also be prepared from an intermediate of Formula 8a by displacement of fluorine with either sodium alkanesulfinate ($R^1SO_2Na$) or sodium alkylsulfide ($R^1SNa$) followed by oxidation of the resulting thioether. The intermediate 8a in turn can be prepared from piperazinone 4a and difluoro nitrobenzene 9a, which are either commercially available or can be readily prepared from commercial precursors based on literature procedures, well known to those of ordinary skill in the art.

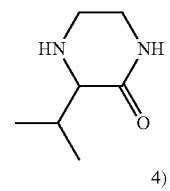

7a

For example, when R³=isopropyl, piperazinone 4a can be prepared by one of the methods presented below.

1)

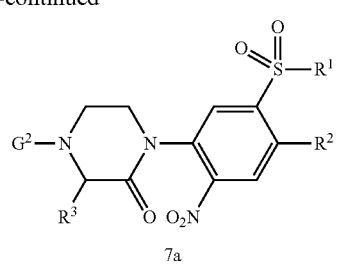
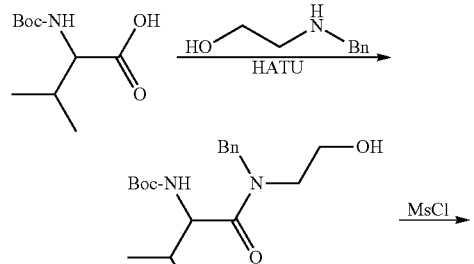

2)

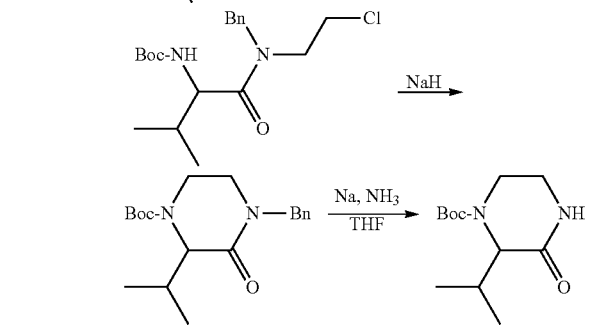

3)

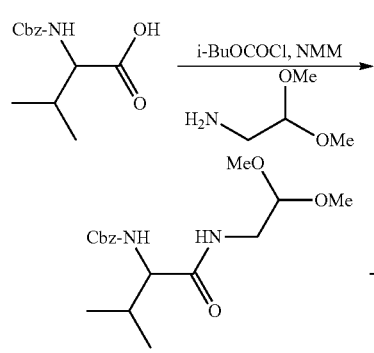

4)

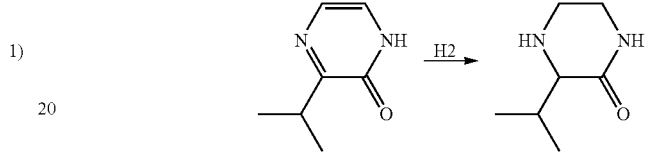
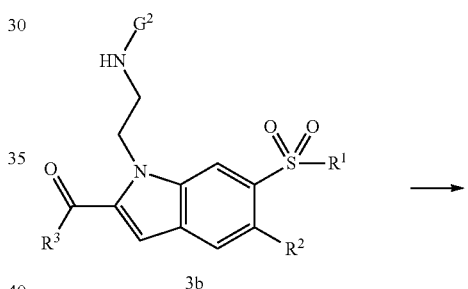

When X=CH, intermediates of Formula 2 can be prepared from intermediates of Formula 3b by deprotection of G² followed by reductive amination. G² are amine protecting groups, such as Boc, Cbz and trifluoroacetamide etc.

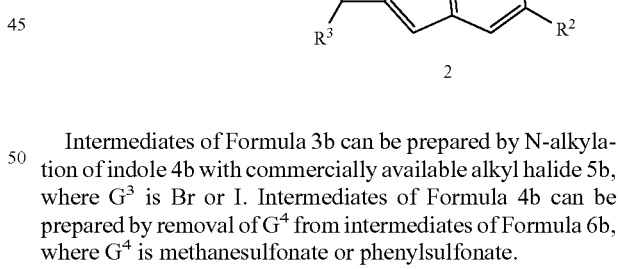

3b

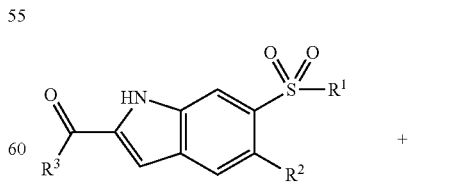

2

Intermediates of Formula 3b can be prepared by N-alkylation of indole 4b with commercially available alkyl halide 5b, where G³ is Br or I. Intermediates of Formula 4b can be prepared by removal of G⁴ from intermediates of Formula 6b, where G⁴ is methanesulfonate or phenylsulfonate.

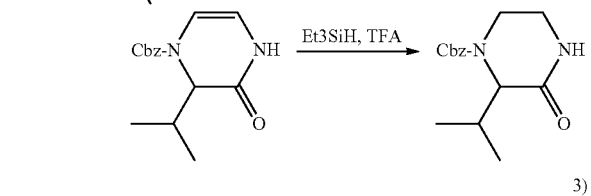

4b

+

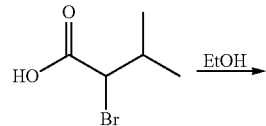

5b

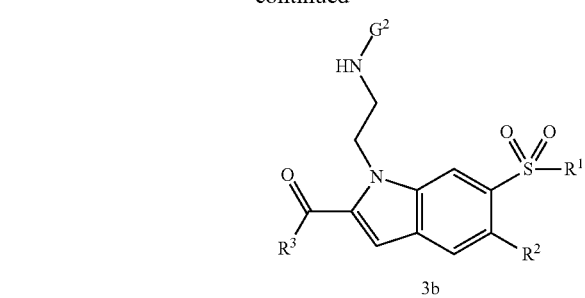
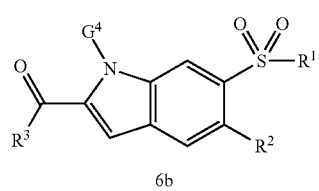

Intermediates of Formula 6b can be prepared by sequential Sonogashira coupling reaction between aryl halides 7b (where $G^5$ is Br or I) and propargyl alcohols 8b, followed by cyclization, to give intermediates of Formula 9b, followed by oxidation of the alcohol.

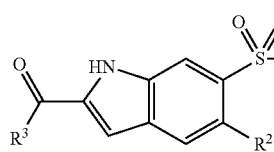

Intermediates of Formula 7b can be prepared from commercially available aniline 10b via the following transformations: 1) Displacement of fluorine with sodium alkyl sulfide $R^1$SNa (yielding 11b); 2) Halogenation (yielding 12b); 3) Protection of the aniline (yielding 13b); 4) Oxidation of the sulfide (yielding 7b).

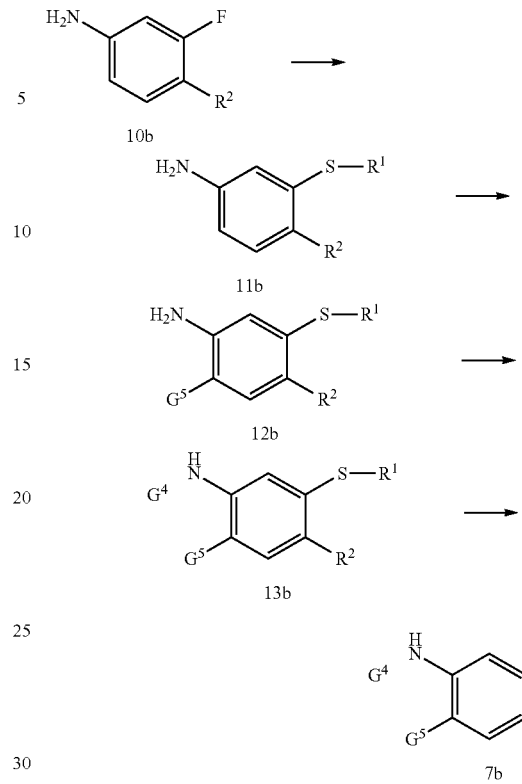

In the second process, a compound of Formula I, where $R^1$=alkyl, $R^2$=H and X=CH, can be prepared by oxidation of the thioether group in intermediates of Formula 1c. Intermediate 1c in turn can be prepared from coupling of reagents 1 and intermediates of Formula 2c via $S_NAr$ or palladium catalyzed reactions.

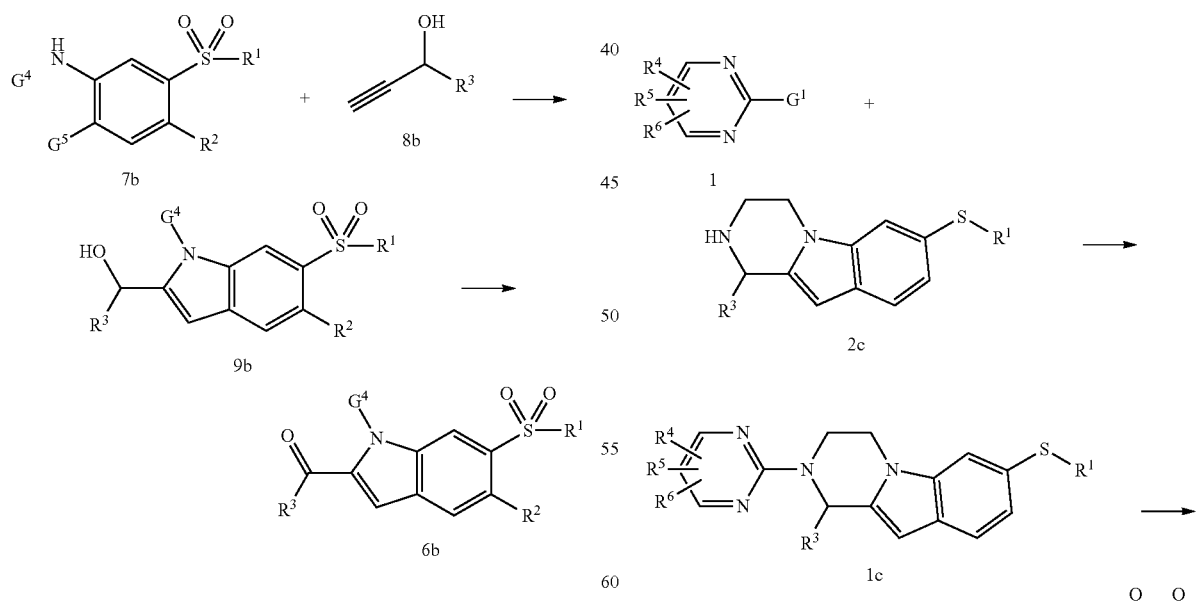

Intermediates 2c can be prepared according to following scheme.

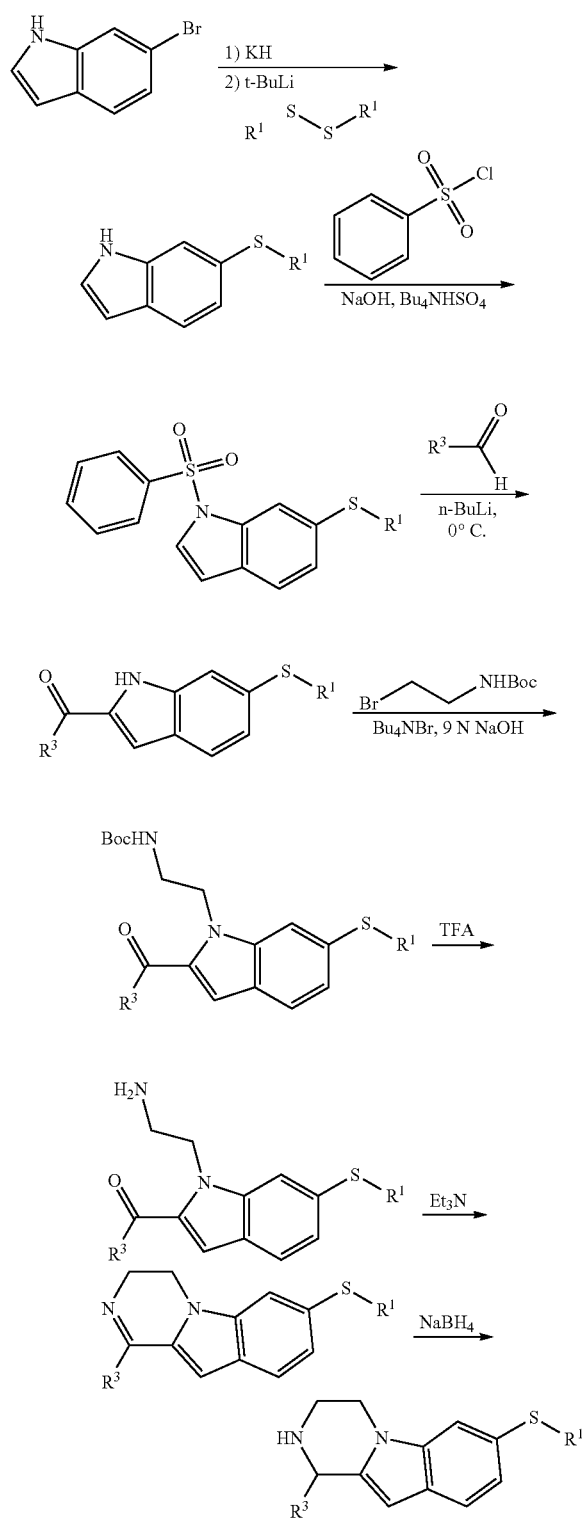

All patents, patent applications, books and literature cited in the specification are hereby incorporated by reference in their entirety. In the case of any inconsistencies, the present disclosure, including any definitions therein will prevail.

The invention will be further described by reference to the following detailed examples, which are given for illustration of the invention, and are not intended to be limiting thereof.

Preparation 1

Tert-butyl 1-isopropyl-7-(methylsulfonyl)-3,4-dihydrobenzo[4,5]imidazo[1,2-a]pyrazine-2(1H)-carboxylate

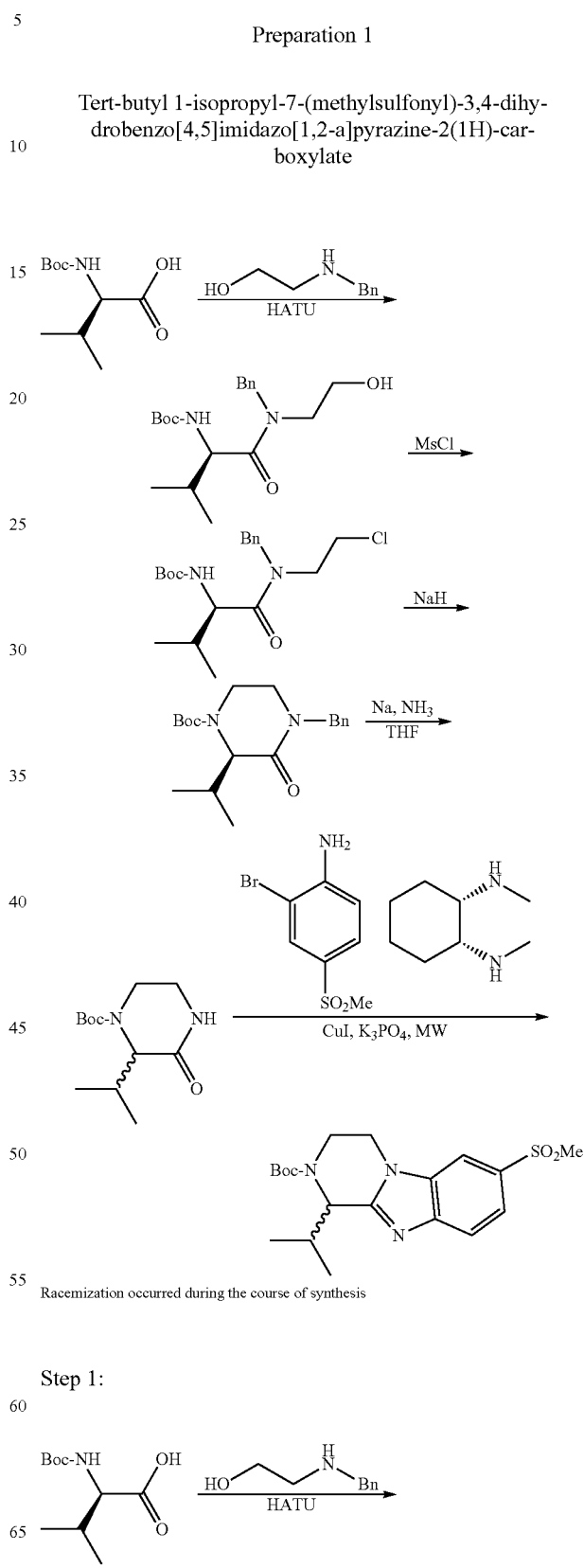

Racemization occurred during the course of synthesis

Step 1:

-continued

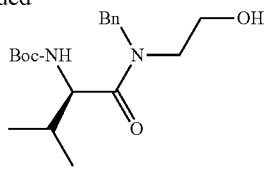

To a solution of (R)-2-((tert-butoxycarbonyl)amino)-3-methylbutanoic acid (2.0 g, 9.20 mmol) in CH$_2$Cl$_2$ (40 mL) were added 2-(benzylamino)ethanol (1.3 g, 8.80 mmol), HATU (5.30 g, 13.8 mmol) and Et$_3$N (2.80 g, 27.6 mmol) under N$_2$. The mixture was stirred at rt overnight. The mixture was diluted with water (20 mL) and extracted with EtOAc (3×30 mL). The combined organic layers were washed with brine (20 mL), dried over anhydrous Na$_2$SO$_4$, filtered, concentrated and purified by column chromatography on silica gel to afford (R)-tert-butyl (1-(benzyl(2-hydroxyethyl)amino)-3-methyl-1-oxobutan-2-yl)carbamate (2.80 g, 88% yield) as a white solid. LC-MS m/z 351.2 [M+H]$^+$.

Step 2:

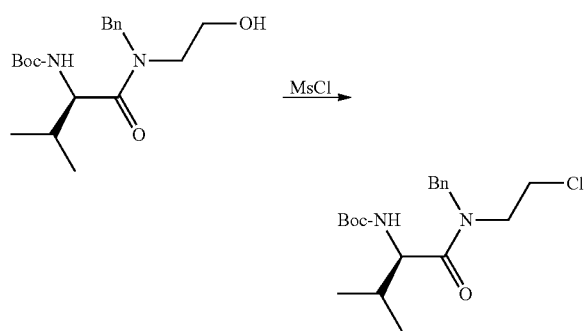

To a solution of (R)-tert-butyl (1-(benzyl(2-hydroxyethyl)amino)-3-methyl-1-oxobutan-2-yl)carbamate (2.80 g, 8.0 mmol) in CH$_2$Cl$_2$ (20 mL) were added Et$_3$N (1.60 g, 16 mmol) and MsCl (1.40 g, 12.0 mmol) dropwse at −10° C. under N$_2$. The mixture was stirred at rt overnight. The mixture was quenched with water (20 mL) and extracted with CH$_2$Cl$_2$ (3×20 mL). The combined organic layers were washed with brine (20 mL) and dried over anhydrous Na$_2$SO$_4$, filtered, concentrated to afford (R)-tert-butyl (1-(benzyl(2-chloroethyl)amino)-3-methyl-1-oxobutan-2-yl)carbamate (3.0 g, 100% yield) as a yellow solid, which was used for the next step without further purification. LC-MS m/z 369.2 [M+H]$^+$. $^1$H NMR (CDCl$_3$ 400 MHz): δ 7.37-7.28 (m, 3H), 7.22-7.20 (m, 2H), 5.27-5.18 (m, 1H), 4.93-4.86 (m, 1H), 4.64-4.39 (m, 2H), 3.85-3.66 (m, 2H), 3.61-3.39 (m, 2H), 2.03-1.97 (m, 1H), 1.45 (s, 9H), 0.98 (d, J=6.8 Hz, 3H), 0.93 (d, J=6.8 Hz, 3H).

Step 3:

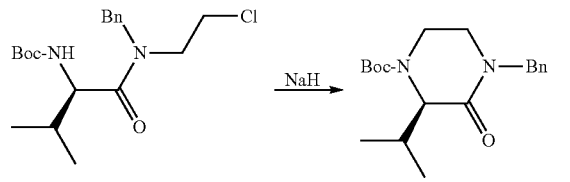

To a solution of (R)-tert-butyl (1-(benzyl(2-chloroethyl)amino)-3-methyl-1-oxobutan-2-yl)carbamate (2.0 g, 5.40 mmol) in DMF (30 mL) was added NaH (1.0 g, 27.0 mmol, 60% in oil mineral) at 0° C. under N$_2$. The mixture was stirred at rt for 2 h. The mixture was quenched with water (20 mL) and extracted with EtOAc (3×20 mL). The combined organic layers were washed with brine (20 mL) and dried over anhydrous Na$_2$SO$_4$, filtered, concentrated and purified by column chromatography to afford (R)-tert-butyl 4-benzyl-2-isopropyl-3-oxopiperazine-1-carboxylate (1.13 g, 63% yield) as a white solid. LC-MS m/z 277.1 [M-56+H]$^+$. $^1$H NMR (CDCl$_3$ 400 MHz): δ 7.38-7.29 (m, 3H), 7.29-7.22 (m, 2H), 5.02-4.86 (m, 1H), 4.49-4.39 (m, 1H), 4.31-4.06 (m, 2H), 3.41-3.18 (m, 3H), 2.42-2.31 (m, 1H), 1.46 (s, 9H), 1.12 (d, J=6.8 Hz, 3H), 1.00 (d, J=6.8 Hz, 3H).

Step 4:

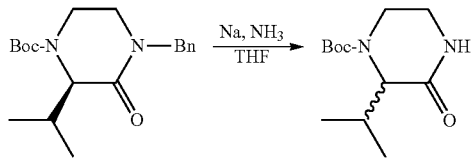

To a three-necked bottle containing THF (10 mL) was bubbled with NH$_3$ (gas) at −78° C. for 5 mins. Na (300 mg, 13.0 mmol) was added to the mixture slowly at −78° C. After stirring for 30 min, (R)-tert-butyl 4-benzyl-2-isopropyl-3-oxopiperazine-1-carboxylate (700 mg, 2.11 mmol) was added dropwise at −78° C. The mixture was stirred at −78° C. for 30 min. The mixture was quenched with sat. aq NH$_4$Cl (10 mL) and extracted with EtOAc (3×10 mL). The combined organic layers were washed with brine (10 mL), dried over anhydrous Na$_2$SO$_4$, filtered, concentrated and purified by preparative TLC with PE/EtOAc 1/1 to afford tert-butyl 2-isopropyl-3-oxopiperazine-1-carboxylate (300 mg, 59% yield) as a white solid. The product was found to be a racemic mixture. The cause of racemization was not investigated. LC-MS m/z 187.1 [M-56+H]$^+$, 265.1 [M+Na]$^+$. $^1$H NMR (CDCl$_3$ 400 MHz): δ 6.29 (s, 1H), 4.55-3.99 (m, 2H), 3.51-3.36 (m, 1H), 3.32-3.12 (m, 2H), 2.34-2.29 (m, 1H), 1.46 (s, 9H), 1.09 (d, J=6.8 Hz, 3H), 0.99 (d, J=7.2 Hz, 3H).

Step 5:

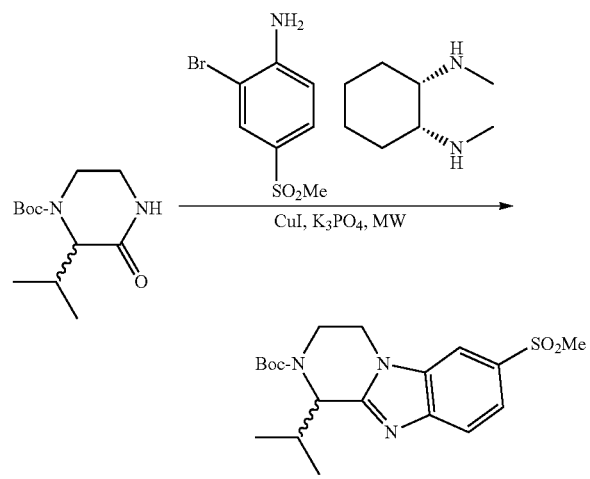

To a solution of tert-butyl 2-isopropyl-3-oxopiperazine-1-carboxylate (200 mg, 0.83 mmol) in NMP (3 mL) was added 2-bromo-4-(methylsulfonyl)aniline (207 mg, 0.83 mmol), (1R,2S)—N1,N2-dimethylcyclohexane-1,2-diamine (12.0 mg, 0.08 mmol), K₃PO₄.3H₂O (660 mg, 2.48 mmol), CuI (16 mg, 0.08 mmol). The mixture was stirred at 150° C. for 1 h under microwave. The mixture was diluted with water (10 mL) and extracted with EtOAc (3×10 mL). The combined organic layers were washed with brine (10 mL), dried over anhydrous Na₂SO₄, filtered, concentrated and purified by preparative TLC with CH₂Cl₂/MeOH 35/1 to afford tert-butyl 1-isopropyl-7-(methylsulfonyl)-3,4-dihydrobenzo[4,5]imidazo[1,2-a]pyrazine-2(1H)-carboxylate (110 mg, 34% yield) as a white solid.

LC-MS m/z 394.1 [M+H]⁺. ¹H NMR (CDCl₃ 400 MHz): δ 7.94 (s, 1H), 7.83-7.76 (m, 2H), 5.35-5.17 (m, 1H), 4.73-4.42 (m, 1H), 4.22-4.12 (m, 1H), 4.11-3.99 (m, 1H), 3.53-3.37 (m, 1H), 3.03 (s, 3H), 2.38-2.27 (m, 1H), 1.42 (s, 9H), 1.19 (d, J=6.8 Hz, 3H), 0.97 (d, J=6.8 Hz, 3H).

Preparation 2

(R)-2-tert-butyl 8-methyl 1-isopropyl-7-(methylsulfonyl)-3,4-dihydrobenzo[4,5]imidazo[1,2-a]pyrazine-2,8(1H)-dicarboxylate

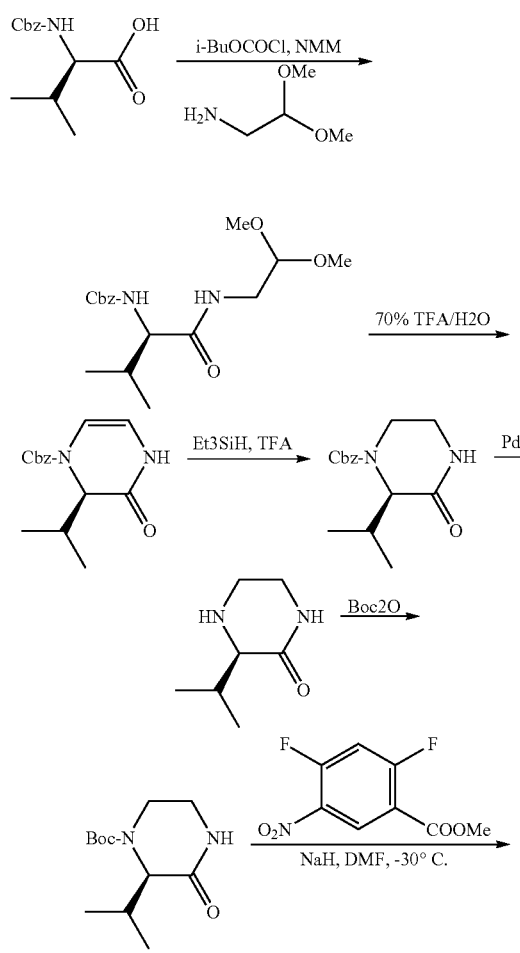

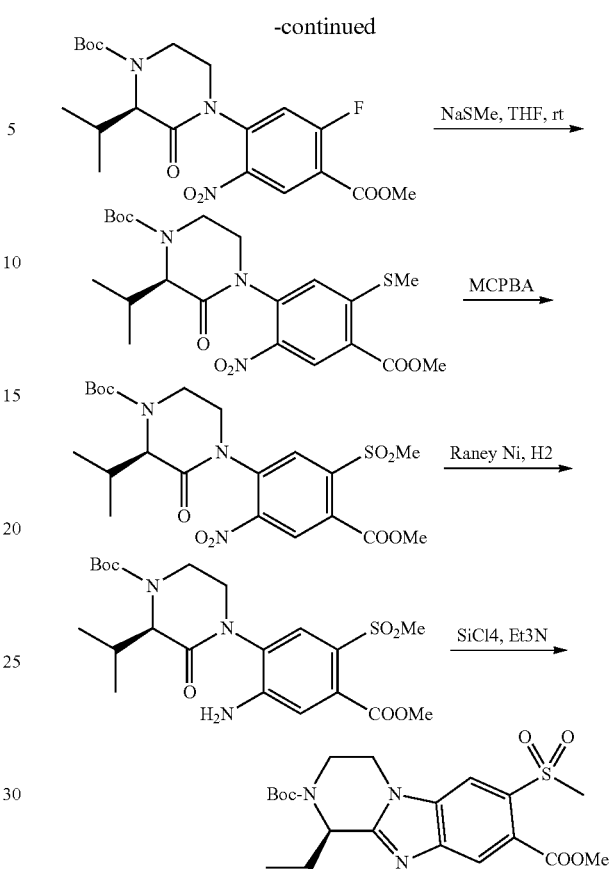

Step 1:

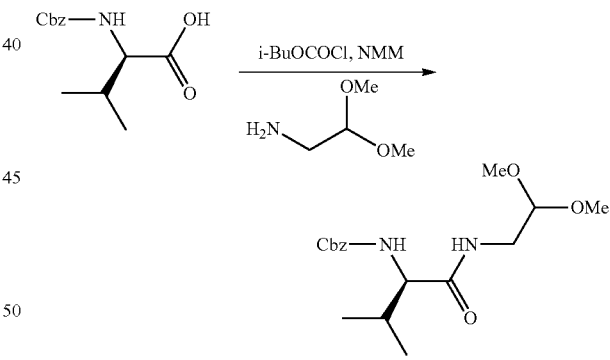

A solution of Cbz-D-Valine (500 g, 1.99 mol) and N-methylmorpholine (201.8 g, 1.99 mol) in anhydrous THF (8 L) was cooled to −15° C., i-butylchlorofomate (299 g, 2.19 mol) was added dropwise under stirring. After 30 min, a solution of 1-amino-2,2-dimethyoxypropane (209.5 g, 1.99 mol) in THF (1 L) was added slowly and the temperature was maintained at −15° C. for 2 h. The reaction mixture was washed with brine (2 L) and the organic phase was concentrated to remove the THF. The residue was diluted with EtOAc (4 L), washed with 1N aqueous HCl (2×2 L), washed with sat. NaHCO₃ (2 L) and Na₂CO₃ (2 L), and washed with brine (1.5 L). After drying over Na₂SO₄, the organic solvent was removed under reduce pressure to afford (R)-benzyl (1-((2,2-dimethoxyethyl)amino)-3-methyl-1-oxobutan-2-yl)carbamate as a white solid (670 g, yield 99.5%), which was used for next step without further purification. LC-MS m/z 360.9 [M+Na]+. 1H NMR (CD3OD 300 MHz): δ 7.35-7.30 (m, 5H), 5.08 (s, 2H), 4.45-4.35 (m, 1H), 3.95-3.85 (m, 1H), 3.34-3.25 (m, 8H), 2.10-1.90 (m, 1H), 0.94-0.91 (m, 6H).
Step 2:

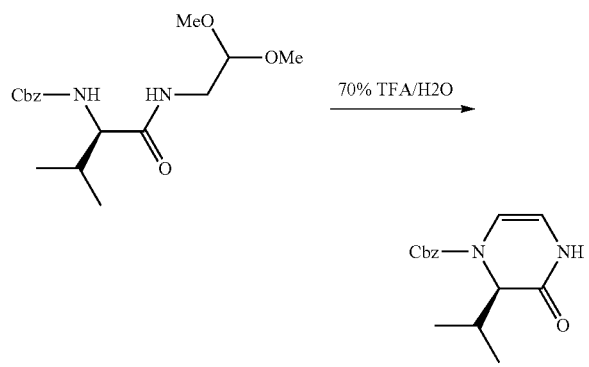

(R)-benzyl (1-((2,2-dimethoxyethyl)amino)-3-methyl-1-oxobutan-2-yl)carbamate (335 g, 0.99 mol) was added in portions to a cooled TFA-H2O (temperature <5° C., $V_{TFA}/V_{H2O}$=7/3, 2 L), and the solution was stirred at rt for 12 h. The solution was added slowly into a stirring cooled sat. aq. Na2CO3 (2.5 L) to keep the pH>8. Then the mixture was extracted with EtOAc (5×2 L). The combined organic layers were washed with brine (2 L), dried over anhydrous Na2SO4, filtered and evaporated in vacuo to give (R)-benzyl 2-isopropyl-3-oxo-3,4-dihydropyrazine-1(2H)-carboxylate as a white solid (259 g, 95.4%), which was used for next step without further purification. LC-MS m/z 274.9 [M+H]+. 1H NMR (CD3OD 300 MHz): δ7.36-7.34 (m, 5H), 6.33-6.30 (m, 1H), 5.79-5.68 (m, 1H), 5.26-5.13 (m, 2H), 4.38-4.29 (m, 1H), 2.01-1.96 (m, 1H), 1.00-0.84 (m, 6H).
Step 3:

To a stirring solution of (R)-benzyl 2-isopropyl-3-oxo-3,4-dihydropyrazine-1(2H)-carboxylate (400 g, 1.46 mol) in DCE (2 L) was added Et3SiH (424 g, 3.65 mol) and TFA (665 g, 5.8 mol) at rt. The reaction was stirred under reflux for 36 h. After cooled to rt, the solution was concentrated to remove the solvent. The residue was diluted with EtOAc (2 L), and it was added slowly into a stirring cooled sat. aq. NaHCO3 (2 L) to make sure that the pH>8. The mixture was extracted with EtOAc (2×2.5 L). The combined organic layers were washed with brine, dried over anhydrous Na2SO4, filter and concentrated to give (R)-benzyl 2-isopropyl-3-oxopiperazine-1-carboxylate (402 g, yield 99.75%), which was used for next step without further purification. LC-MS m/z 276.9 [M+H]+. 1H NMR (DMSO-d6 400 MHz): δ 7.93 (s, 1H), 7.39-7.31 (m, 5H), 5.09 (s, 2H), 4.06-4.01 (m, 1H), 3.99-3.92 (m, 1H), 3.23-3.14 (m, 3H), 2.20-2.12 (m, 1H), 0.96-0.94 (m, 3H), 0.85 (d, J=6.0 Hz, 3H).

Step 4:

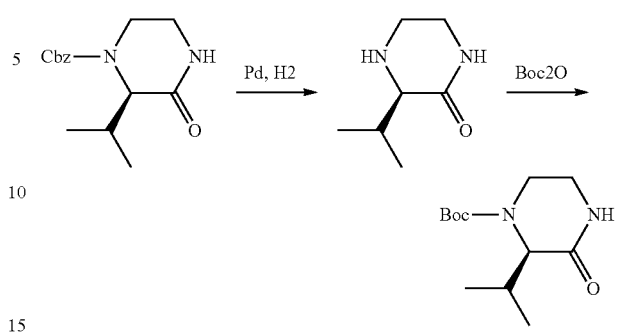

To a 1 L round-bottom flask containing (R)-benzyl 2-isopropyl-3-oxopiperazine-1-carboxylate (50 g, 0.181 mol) in MeOH (800 mL) was added Pd/C (dry, w/w 15%, 5 g). The mixture was stirred at rt under H2 (1 atm) overnight. When TLC and LCMS showed that the starting material was consumed, (Boc)2O (76.74 g, 0.352 mol) was added to the reaction mixture, and the mixture was stirred at rt overnight until the intermediate (R)-3-isopropylpiperazin-2-one was consumed. The mixture was filtered and concentrated under vacuum to give a residue. The residue was purified by column chromatography on silica gel (eluting with PE:EtOAc=3:1) to give (R)-tert-butyl 2-isopropyl-3-oxopiperazine-1-carboxylate as a white solid (26 g, yield 61%. For (R)-3-isopropylpiperazin-2-one: LC-MS m/z 143.2 [M+H]+. 1H NMR (HCl salt, CD3OD 400 MHz): δ 3.95 (d, J=3.6 Hz, 1H), 3.65-3.39 (m, 4H), 2.63-2.54 (m, 1H), 1.15 (d, J=6.8 Hz, 3H), 1.09 (d, J=7.2 Hz, 3H). For (R)-tert-butyl 2-isopropyl-3-oxopiperazine-1-carboxylate: LC-MS m/z 186.9 [M-56+H]+. 1H NMR (DMSO-d6 400 MHz): δ 7.93 (s, 1H), 4.02-3.82 (m, 2H), 3.17-3.15 (m, 3H), 2.16 (s, 1H), 1.41 (s, 9H), 0.98 (d, J=6.8 Hz, 3H), 0.89 (d, J=6.4 Hz, 3H).
Step 5:

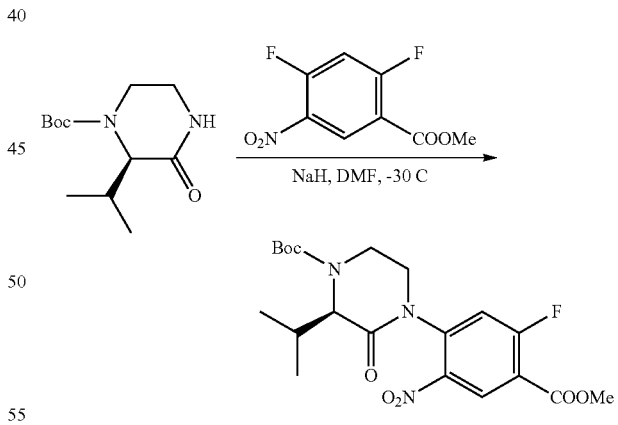

Under N2 atmosphere, NaH (8.8 g, 0.22 mol, 60% in mineral oil, 1.1 eq.) was added in portions at −10° C. to a 1 L three-neck flask containing (R)-tert-butyl 2-isopropyl-3-oxopiperazine-1-carboxylate (26.7 g, 0.11 mol) in DMF (300 mL). The mixture was stirred at −10° C. for 30 min. The mixture was added dropwise to a 1 L three-neck flask containing methyl 2,4-difluoro-5-nitrobenzoate (26.3 g, 0.121 mol, 1.1 eq.) in DMF (200 mL) at −20° C. over 10 min. After addition, the resulting mixture was stirred between −20° C. and −30° C. for another 10 min. The reaction was quenched with sat. aq. ammonium chloride (200 mL) and then water (800 mL). The aqueous layer was extracted with EtOAc (3×1 L). The combined organic layers were washed with water (3×1 L) and brine, and then dried over anhydrous $Na_2SO_4$. After the mixture was filtered and the filter was evaporated under vacuum, the residue was purified by column chromatography on silica gel eluting with PE:EtOAc 8:1~4:1 to give (R)-tert-butyl 4-(5-fluoro-4-(methoxycarbonyl)-2-nitrophenyl)-2-isopropyl-3-oxopiperazine-1-carboxylate (32 g, 66.3% yield) as a yellow solid. LC-MS MS (ESI) m/z 384.1 $[M-56+H]^+$, 462.1 $[M+Na]^+$. $^1H$ NMR ($CDCl_3$ 300 MHz): δ 8.63 (d, J=6.9 Hz, 1H), 7.16 (d, J=10.2 Hz, 1H), 4.61-4.30 (m, 2H), 3.97-3.89 (m, 4H), 3.62-3.48 (m, 2H), 2.40-2.34 (m, 1H), 1.49 (s, 9H), 1.08 (d, J=6.9 Hz, 3H), 1.01 (d, J=6.9 Hz, 3H).

Step 6:

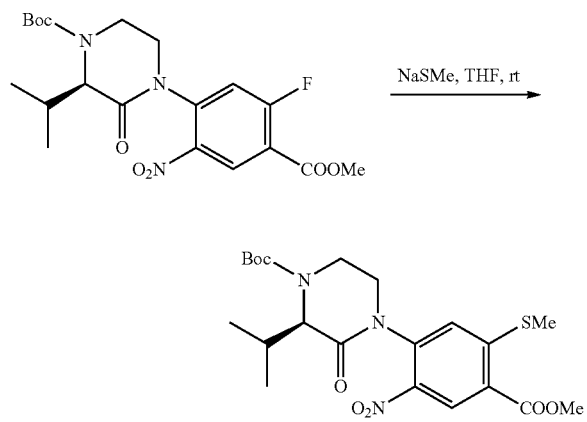 [SMILES: COC(=O)c1cc([N+](=O)[O-])c(N2CCN(C(=O)OC(C)(C)C)[C@H](C(C)C)C2=O)cc1F ; COC(=O)c1cc([N+](=O)[O-])c(N2CCN(C(=O)OC(C)(C)C)[C@H](C(C)C)C2=O)cc1SC]

To a 1 L round-bottom flask containing (R)-tert-butyl 4-(5-fluoro-4-(methoxycarbonyl)-2-added NaSMe (14.3 g, 0.204 mmol, 3 eq.). The mixture was stirred at rt for 1 h. Water (500 mL) was added and the mixture was concentrated under vacuum to remove THF. The aqueous layer was extracted with EtOAc (3×800 mL). The combined organic layers were washed with brine, dried over anhydrous $Na_2SO_4$, filtered and concentrated under vacuum to give (R)-tert-butyl 2-isopropyl-4-(4-(methoxycarbonyl)-5-(methylthio)-2-nitrophenyl)-3-oxopiperazine-1-carboxylate (31.9 g, 100% yield) as a yellow solid. The residue was used directly for the next step without further purification. LC-MS MS (ESI) m/z 412.1 $[M-56+H]^+$, 490.2 [M+Na].

Step 7:

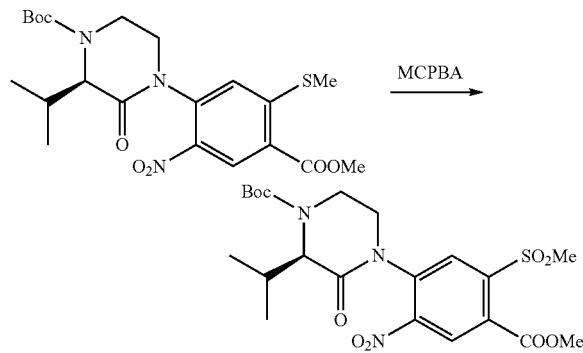

To a 2 L round-bottom flask containing (R)-tert-butyl 2-isopropyl-4-(4-(methoxycarbonyl)-5-(methylthio)-2-nitrophenyl)-3-oxopiperazine-1-carboxylate (crude 91.7 g, 0.196 mol) in $CH_2Cl_2$ (1 L) was added m-CPBA (84.6 g, 0.49 mmol, 2.5 eq). The mixture was stirred at rt overnight. Sat. $Na_2S_2O_3$ was added slowly to quench the reaction. The mixture was extracted with $CH_2Cl_2$ (4×3 L). The combined organic layers were washed successively with $Na_2S_2O_3$ solution (500 mL), $NaHCO_3$ solution (500 mL) and brine, dried over anhydrous $Na_2SO_4$, filtered and concentrated under vacuum. The residue was purified by column chromatography on silica gel eluting with dichloromethane to give (R)-tert-butyl 2-isopropyl-4-(4-(methoxycarbonyl)-5-(methylsulfonyl)-2-nitrophenyl)-3-oxopiperazine-1-carboxylate (83.7 g, 85.4% yield) as a yellow solid. LC-MS MS (ESI) m/z 444.0 $[M-56+H]^+$, 522.1 $[M+Na]^+$. $^1H$ NMR ($CDCl_3$ 300 MHz): δ 8.29 (s, 1H), 8.12 (s, 1H), 4.61-4.17 (m, 2H), 4.00-3.94 (m, 4H), 3.70-3.60 (m, 1H), 3.51-3.43 (m, 4H), 2.39-2.32 (m, 1H), 1.50 (s, 9H), 1.07 (d, J=6.9 Hz, 3H), 1.01 (d, J=6.9 Hz, 3H).

Step 8:

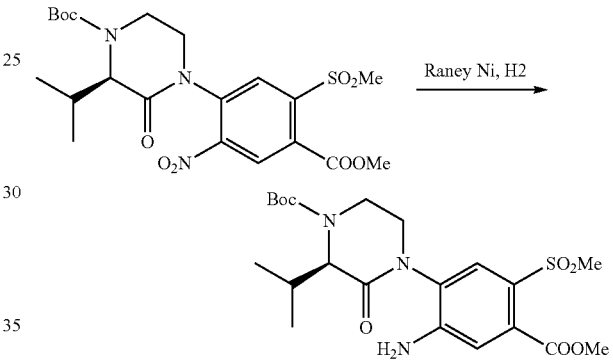

To a 1 L round-bottom flask containing (R)-tert-butyl 2-isopropyl-4-(4-(methoxycarbonyl)-5-(methylsulfonyl)-2-nitrophenyl)-3-oxopiperazine-1-carboxylate (26.3 g, 0.0526 mol) in THF (200 mL) and methanol (200 mL) was added Raney Nickel (in $H_2O$, 4 g). The mixture was stirred under $H_2$ (30 psi) at rt overnight. The mixture was filtered and concentrated under vacuum to give (R)-tert-butyl 4-(2-amino-4-(methoxycarbonyl)-5-(methylsulfonyl)phenyl)-2-isopropyl-3-oxopiperazine-1-carboxylate (24.7 g, 100% yield) as a yellow solid. The residue was used directly for the next step without further purification.

LC-MS MS (ESI) m/z 414.0 $[M-56+H]^+$, 492.0 [M+Na]. $^1H$ NMR ($CDCl_3$ 300 MHz): δ 7.77 (brs, 1H), 7.04 (s, 1H), 4.68-4.45 (m, 1H), 4.45-4.38 (m, 2H), 3.92 (s, 3H), 3.70-3.58 (m, 1H), 3.58-3.41 (m, 1H), 3.30 (s, 3H), 2.49-2.25 (m, 1H), 1.50 (s, 9H), 1.12 (d, J=6.9 Hz, 3H), 1.05 (d, J=6.9 Hz, 3H).

Step 9:

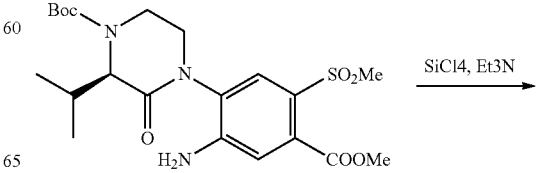

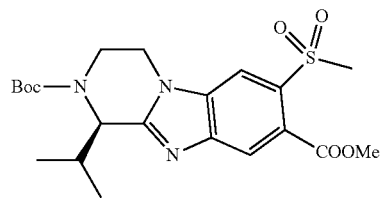

To a 1 L round-bottom flask containing (R)-tert-butyl 4-(2-amino-4-(methoxycarbonyl)-5-(methylsulfonyl)phenyl)-2-isopropyl-3-oxopiperazine-1-carboxylate (25 g, 0.0532 mol) in dichloromethane (500 mL) was added Et$_3$N (64.5 g, 0.638 mol, 12 eq.) and SiCl$_4$ (27.1 g, 0.160 mol, 3 eq.). The mixture was stirred at rt overnight. The mixture was added dropwise to aq. NaHCO$_3$ solution (54.1 g in 1 L of water, 0.644 mol, 12.1 eq.) at 0° C. slowly and adjusted to pH=8. The mixture was filtered and the aqueous layer was extracted with dichloromethane (3×600 mL). The combined organic layers were washed with brine, and then dried over anhydrous Na$_2$SO$_4$. The mixture was filtered and concentrated under vacuum to give the residue. The residue was purified by column chromatography on silica gel eluting with PE:EtOAc 2:1 to give (R)-2-tert-butyl 8-methyl 1-isopropyl-7-(methylsulfonyl)-3,4-dihydrobenzo[4,5]imidazo[1,2-a]pyrazine-2,8(1H)-dicarboxylate (13.2 g, 55% yield) as a pale yellow solid. Analytical chiral HPLC: t$_R$=9.03 min in 15 min chromatography (Method: OD-3_3_5_40_2.5 ML). LC-MS MS (ESI) m/z 452.2 [M+H]$^+$. $^1$H NMR (CD$_3$OD 400 MHz): δ 8.31 (s, 1H), 8.01 (s, 1H), 5.30-5.18 (m, 1H), 4.70-4.52 (m, 1H), 4.47 (dd, J=3.2 and 12.4 Hz, 1H), 4.18 (dt, J=5.2 and 11.6 Hz, 1H), 3.98 (s, 3H), 3.70-3.52 (m, 1H), 3.44 (s, 3H), 2.50-2.38 (m, 1H), 1.53 (s, 9H), 1.25 (d, J=6.8 Hz, 3H), 1.06 (d, J=6.8 Hz, 3H).

Preparation 3

1-isopropyl-7-(methylthio)-1,2,3,4-tetrahydropyrazino[1,2-a]indole

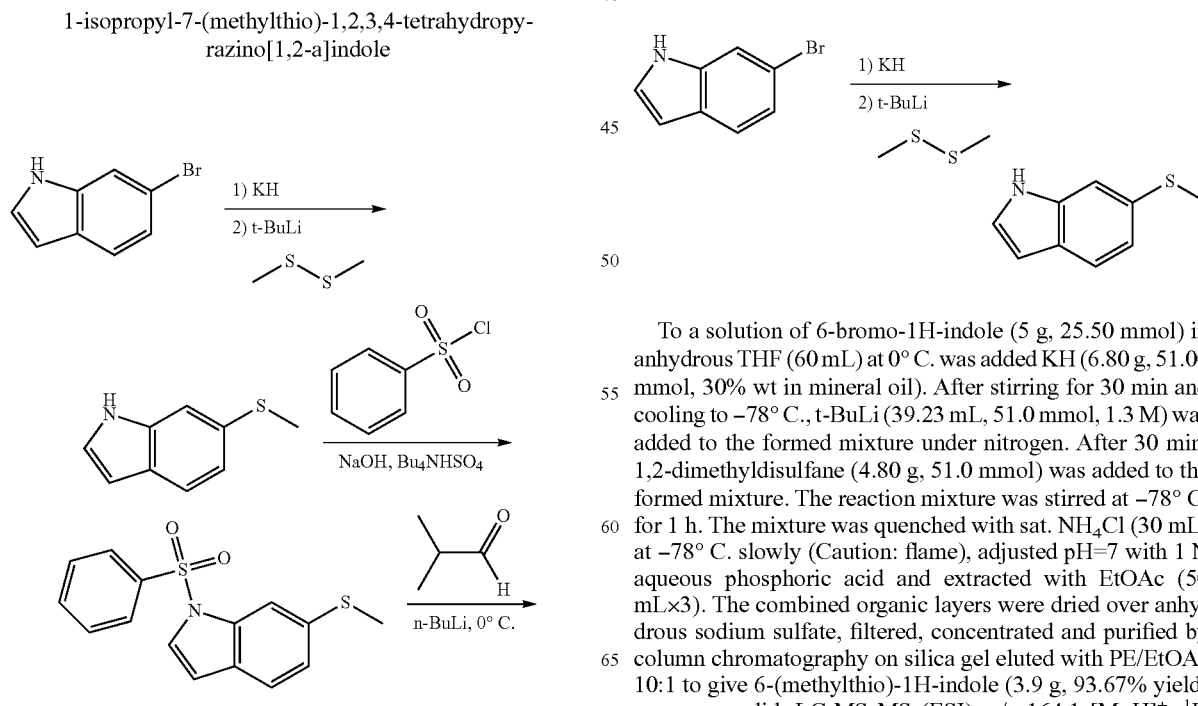

Step 1:

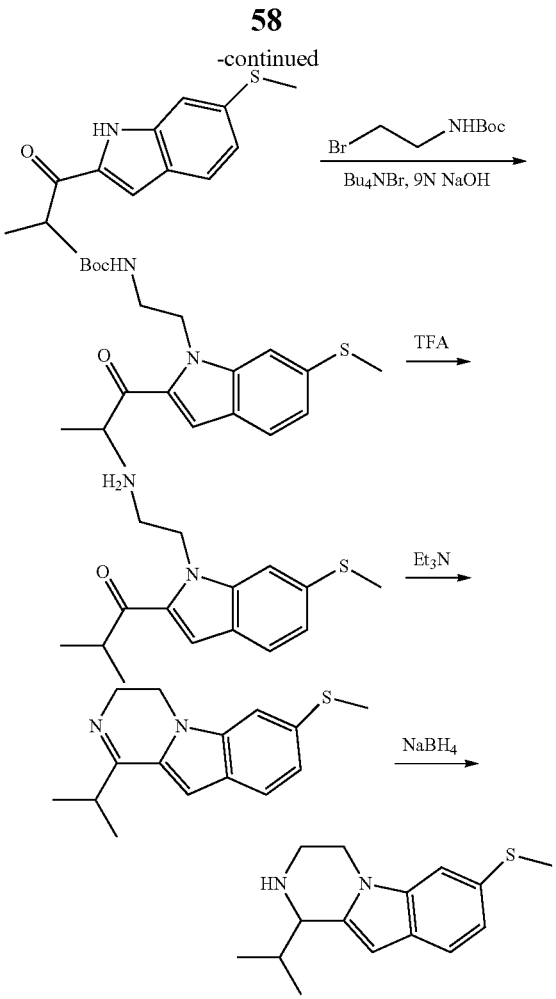

To a solution of 6-bromo-1H-indole (5 g, 25.50 mmol) in anhydrous THF (60 mL) at 0° C. was added KH (6.80 g, 51.00 mmol, 30% wt in mineral oil). After stirring for 30 min and cooling to −78° C., t-BuLi (39.23 mL, 51.0 mmol, 1.3 M) was added to the formed mixture under nitrogen. After 30 min, 1,2-dimethyldisulfane (4.80 g, 51.0 mmol) was added to the formed mixture. The reaction mixture was stirred at −78° C. for 1 h. The mixture was quenched with sat. NH$_4$Cl (30 mL) at −78° C. slowly (Caution: flame), adjusted pH=7 with 1 N aqueous phosphoric acid and extracted with EtOAc (50 mL×3). The combined organic layers were dried over anhydrous sodium sulfate, filtered, concentrated and purified by column chromatography on silica gel eluted with PE/EtOAc 10:1 to give 6-(methylthio)-1H-indole (3.9 g, 93.67% yield) as a grey solid. LC-MS MS (ESI) m/z 164.1 [M+H]$^+$. $^1$H NMR (CDCl₃ 400 MHz): δ 8.14 (brs, 1H), 7.56 (d, J=8.0 Hz, 1H), 7.37 (s, 1H), 7.18-7.11 (m, 1H), 6.56-6.51 (m, 1H), 2.52 (s, 3H).

Step 2:

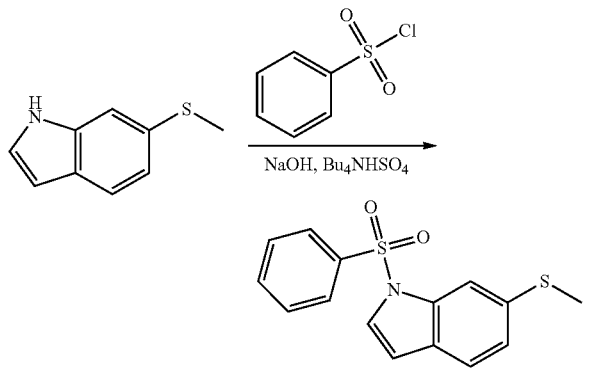

To a solution of 6-(methylthio)-1H-indole (1 g, 6.13 mmol), NaOH (4.90 g, 122.6 mmol) and Bu₄NHSO₄ (207.8 mg, 0.613 mmol) in dichloromethane (20 mL) was added benzenesulfonyl chloride (1.29 g, 7.36 mmol). The reaction mixture was stirred at rt overnight. The mixture was quenched with water (30 mL) and extracted with dichloromethane (30 mL×3). The combined organic layers were dried over anhydrous sodium sulfate, filtered, concentrated and purified by column chromatography on silica gel eluted with PE/EtOAc 10:1 to afford 6-(methylthio)-1-(phenylsulfonyl)-1H-indole (1.1 g, 59.18% yield) as a white solid.

LC-MS MS (ESI) m/z 304.0 [M+H]⁺. ¹H NMR (CDCl₃ 400 MHz): δ 7.93-7.75 (m, 3H), 7.58-7.41 (m, 5H), 7.17 (dd, J₁=8.0 Hz, J₂=1.6 Hz, 1H), 6.63-6.60 (m, 1H), 2.53 (s, 3H).

Step 3:

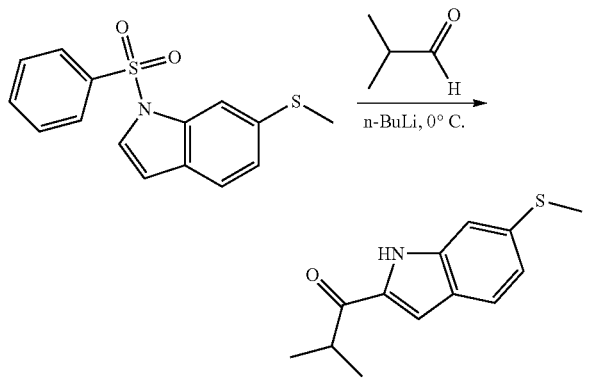

To a solution of 6-(methylthio)-1-(phenylsulfonyl)-1H-indole (890 mg, 2.93 mmol) in anhydrous THF (10 mL) at 0° C. under nitrogen was added n-BuLi (5.86 mL, 14.65 mmol, 2.5 M). After stirring for 30 min, isobutyraldehyde (1.05 g, 14.65 mmol) was added to the formed mixture. The reaction mixture was stirred at 0° C. for 1 h. The mixture was quenched with sat. NH₄Cl (10 mL) at 0° C. and extracted with EtOAc (20 mL×3). The combined organic layers were dried over anhydrous sodium sulfate, filtered, concentrated and purified by column chromatography on silica gel eluted with PE/EtOAc 20:1 to give 2-methyl-1-(6-(methylthio)-1H-indol-2-yl)propan-1-one (440 mg, 64.28% yield) as a colorless oil. LC-MS MS (ESI) m/z 234.1 [M+H]⁺. ¹H NMR (CDCl₃

400 MHz): δ 8.86 (brs, 1H), 7.52 (d, J=8.4 Hz, 1H), 7.19 (s, 1H), 7.14-7.11 (m, 1H), 7.01 (dd, J₁=8.4 Hz, J₂=1.6, 1H), 3.42-3.38 (m, 1H), 2.47 (s, 3H), 1.20 (d, J=6.8 Hz, 6H).

Step 4:

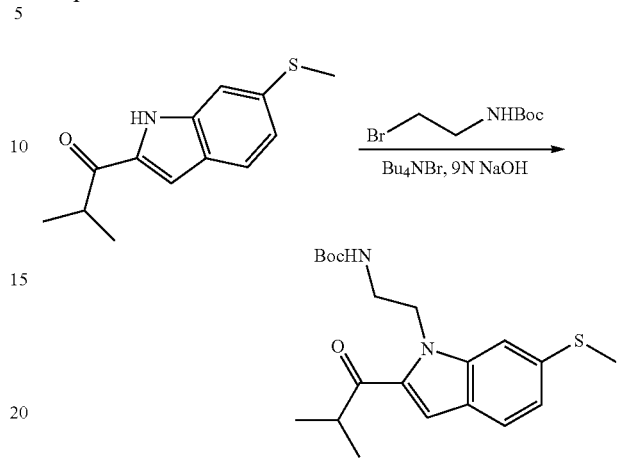

To a solution of 2-methyl-1-(6-(methylthio)-1H-indol-2-yl)propan-1-one (600 mg, 2.57 mmol) and Bu₄NBr (4.12 g, 12.85 mmol) in 9 N NaOH (10 mL, cooled) was added tert-butyl (2-bromoethyl)carbamate (2.87 g, 12.85 mmol). The reaction mixture was stirred at rt for 72 h. The mixture was diluted with water (20 mL) at 0° C., extracted with EtOAc (20 mL×3). The combined organic layers were dried over anhydrous sodium sulfate, filtered, concentrated and purified by column chromatography on silica gel eluting with PE/EtOAc 10:1 to afford tert-butyl (2-(2-isobutyryl-6-(methylthio)-1H-indol-1-yl)ethyl)carbamate (200 mg, 20.66% yield) as a colorless oil. LC-MS MS (ESI) m/z 321.1 [M-56+H]⁺, 277.1 [M-100+H]⁺. ¹H NMR (CDCl₃ 400 MHz): δ 7.57 (d, J=8.4 Hz, 1H), 7.38 (s, 1H), 7.29 (s, 1H), 7.10 (d, J=8.4 Hz, 1H), 4.80 (brs, 1H), 4.62 (t, J=6.4 Hz, 2H), 3.58-3.42 (m, 3H), 2.58 (s, 3H), 1.38 (s, 9H), 1.24 (d, J=6.8 Hz, 6H).

Step 5:

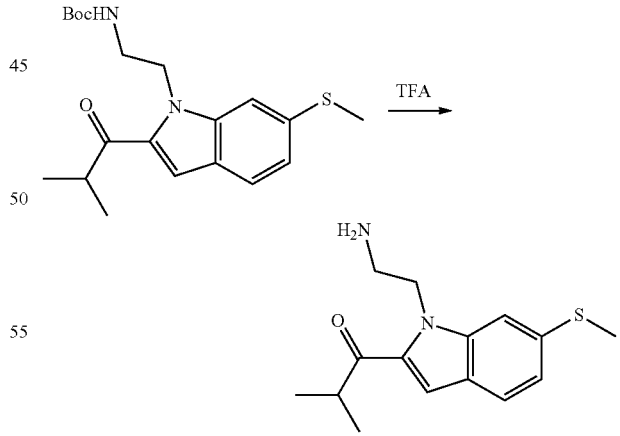

To a solution afford tert-butyl (2-(2-isobutyryl-6-(methylthio)-1H-indol-1-yl)ethyl)carbamate (200 mg, 0.53 mmol) in dichloromethane (9 mL) at 0° C. was added TFA (1 mL). The reaction mixture was stirred at rt for 1 h. The mixture was concentrated (T<25° C.), treated with water (5 mL), adjusted pH=11 with sat. NaHCO₃ and extracted with EtOAc (20 mL×3). The combined organic layers were dried over anhydrous sodium sulfate, filtered, concentrated to afford 1-(1-(2-aminoethyl)-6-(methylthio)-1H-indol-2-yl)-2-methylpropan-1-one (210 mg, 100% yield) as a colorless oil. LC-MS MS (ESI) m/z 258.8 [M-18+H]⁺.

Step 6:

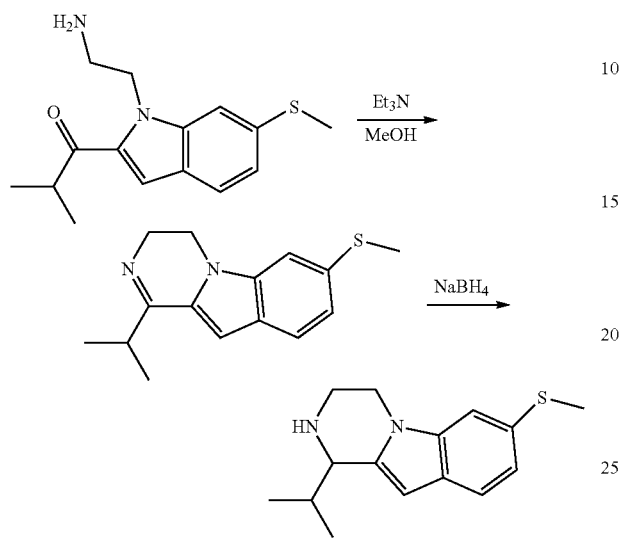

To a solution of 1-(1-(2-aminoethyl)-6-(methylthio)-1H-indol-2-yl)-2-methylpropan-1-one (200 mg, 0.724 mmol) in MeOH (5 mL) was added Et₃N (219.3 mg, 2.172 mmol). The reaction mixture was stirred at 60° C. for 1 h. Then NaBH₄ (82.53 mg, 2.172 mmol) was added to the formed mixture. The mixture was stirred at 60° C. for another 1 h. The mixture was concentrated, treated with water (10 mL) and extracted with EtOAc (20 mL×3). The combined organic layers were dried over anhydrous sodium sulfate, filtered, concentrated and purified by preparative TLC on silica gel eluted with PE/EtOAc 1:1 to afford 1-isopropyl-7-(methylthio)-1,2,3,4-tetrahydropyrazino[1,2-a]indole (80 mg, 42.46% yield, store at 0° C.) as a colorless oil. LC-MS of 1-Isopropyl-7-methylsulfanyl-3,4-dihydro-pyrazino[1,2-a]indole MS (ESI) m/z 259.1 [M+H]⁺. LC-MS of 1-isopropyl-7-(methylthio)-1,2,3,4-tetrahydropyrazino[1,2-a]indole MS (ESI) m/z 261.2 [M+H]⁺. ¹H NMR (CDCl₃ 400 MHz): δ 7.41 (d, J=8.4 Hz, 1H), 7.20 (s, 1H), 7.05 (dd, J₁=8.4 Hz, J₂=1.6 Hz, 1H), 6.12 (s, 1H), 4.02-3.97 (m, 2H), 3.86-3.80 (m, 1H), 3.46-3.42 (m, 1H), 3.16-3.10 (m, 1H), 2.48 (s, 3H), 2.32-2.27 (m, 1H), 1.09 (d, J=6.8 Hz, 3H), 0.86 (d, J=6.8 Hz, 3H).

Preparation 4

8-(((tert-butyldiphenylsilyl)oxy)methyl)-1-isopropyl-7-(methylsulfonyl)-1,2,3,4-tetrahydropyrazino[1,2-a]indole

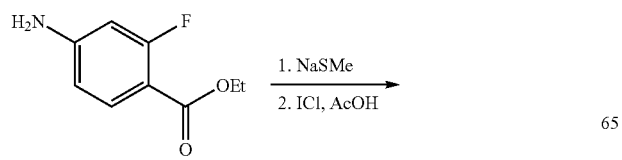

-continued

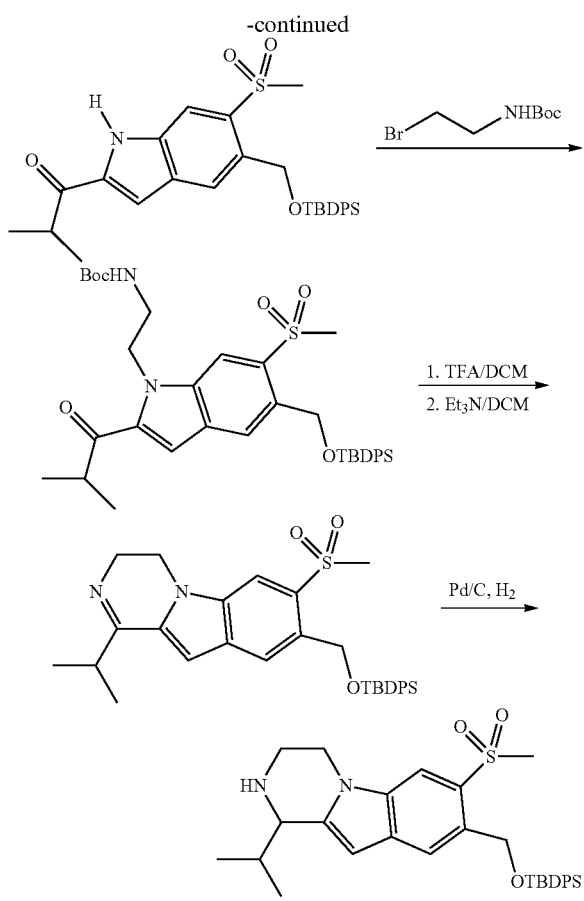

Step 1:

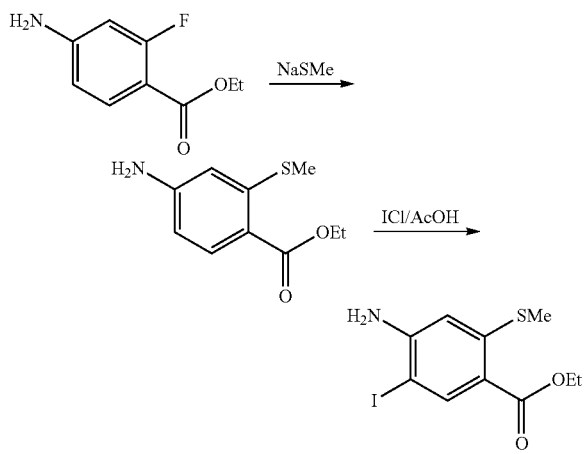

To a solution of ethyl 4-amino-2-fluorobenzoate (12 g, 65.5 mmol) in DMF (100 mL) was added NaSMe (9.17 g, 131 mmol) and the mixture was stirred at 60° C. for 20 h. After cooling to rt, the reaction was diluted with H₂O and extracted with EtOAc (3×100 mL). The combined organic phases were washed with brine, dried over anhydrous sodium sulfate, filtered and concentrated in vacuo to afford ethyl 4-amino-2-(methylthio)benzoate. To a pre-heated 60° C. solution of ethyl 4-amino-2-(methylthio)benzoate (65 mmol) in acetic acid (150 mL) was added ICl/AcOH solution (1M, 72 mL, 72 mmol) dropwise during 40 min and the temperature was maintained at 60° C. for 3 h. After cooling to rt the reaction was diluted with EtOAc (500 mL) and washed with 5% sodium thiosulfate solution (3×100 mL) and brine (200 mL), dried over anhydrous sodium sulfate, filtered and concentrated in vacuo. The crude product was purified by silica gel chromatography (0-20% EtOAc/Hexanes) to afford ethyl 4-amino-5-iodo-2-(methylthio)benzoate (13.67 g, 53% yield). For ethyl 4-amino-2-(methylthio)benzoate: LC-MS m/z 212 [M+H]⁺. For ethyl 4-amino-5-iodo-2-(methylthio)benzoate: LC-MS m/z 338 [M+H]⁺. ¹H NMR (400 MHz, CDCl₃): δ 8.29 (s, 1H), 6.47 (s, 1H), 4.49 (br s, 2H), 4.31 (q, J=7.2 Hz, 2H), 2.38 (s, 3H), 1.37 (t, J=7.2 Hz, 3H).

Step 2:

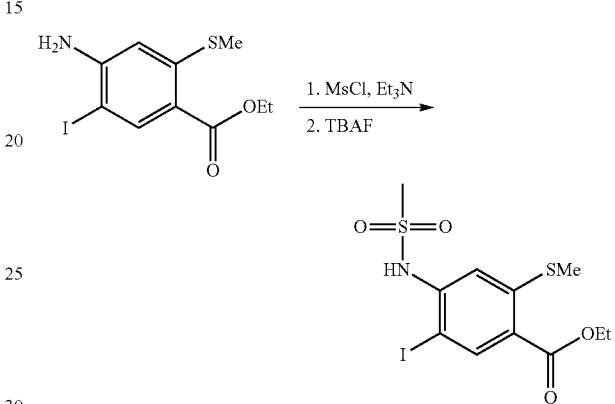

To a solution of ethyl 4-amino-5-iodo-2-(methylthio)benzoate (13.6 g, 40 mmol) in DCM (100 mL) was added Et₃N (13.8 mL, 100 mmol), followed by MsCl (7.7 mL, 100 mmol) at 0° C. After addition the mixture was stirred at rt for 2 h. 1N HCl solution (50 mL) was added to the mixture and the aqueous phase was extracted with DCM (1×100 mL). The organic solution was washed with brine, dried over anhydrous sodium sulfate, filtered and concentrated in vacuo to give ethyl 5-iodo-4-(N-(methylsulfonyl)methylsulfonamido)-2-(methylthio)benzoate.

The crude reaction mixture above was dissolved into 100 mL THF. To this solution was added TBAF THF solution (1 M, 100 mL) and the mixture was stirred at rt for 2 h. H₂O was added to the mixture and the aqueous phase was extracted with EtOAc (3×100 mL). The combined organic solution was washed with brine, dried over anhydrous sodium sulfate, filtered and concentrated in vacuo to afford ethyl 5-iodo-4-(methylsulfonamido)-2-(methylthio)benzoate. It was used for next step without further purification. For ethyl 5-iodo-4-(N-(methylsulfonyl)methylsulfonamido)-2-(methylthio)benzoate: LC-MS m/z 494 [M+H]⁺. For ethyl 5-iodo-4-(methylsulfonamido)-2-(methylthio)benzoate: LC-MS m/z 415 [M+H]⁺.

Step 3:

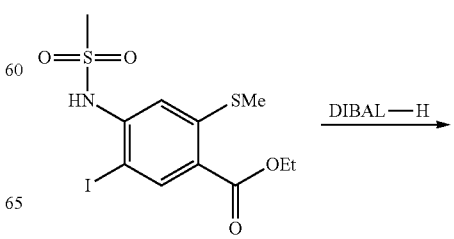

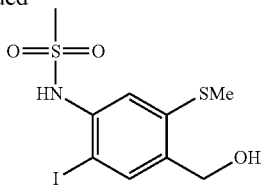

To a solution of ethyl 5-iodo-4-(methylsulfonamido)-2-(methylthio)benzoate (crude, from step 2) in dry toluene (200 mL) at 0° C. was added diisobutylaluminium hydride (1.0 M in toluene, 100 mL, 100 mmol) slowly. After addition, the mixture was stirred at 0° C. for 3 h and quenched with methanol/H$_2$O (1/1). The reaction mixture was poured into a vigorously stirred solution of potassium sodium tartrate (1M, 300 mL) and stirred vigorously for 2 h, after which time it settled to two clear phases. The organic layer was separated, and the aqueous layer was extracted with EtOAc (3×200 mL). The combined organic solution was washed with brine, dried over anhydrous sodium sulfate, filtered and concentrated in vacuo. The crude product was purified by silica gel chromatography (0-40% EtOAc/Hexanes) to afford N-(4-(hydroxymethyl)-2-iodo-5-(methylthio)phenyl)methanesulfonamide (11.9 g, 80% yield for two steps). LC-MS m/z 356 [M+H]$^+$. $^1$H NMR (400 MHz, CDCl$_3$): δ 7.82 (s, 1H), 7.49 (s, 1H), 4.67 (s, 2H), 2.99 (s, 3H), 2.50 (s, 3H).

Step 4:

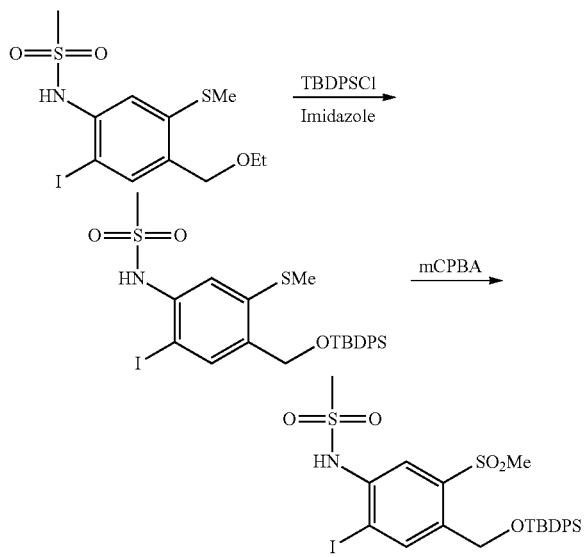

To a stirred solution of N-(4-(hydroxymethyl)-2-iodo-5-(methylthio)phenyl)methanesulfonamide (6.4 g, 17.2 mmol) and imidazole (1.76 g, 25.8 mmol) in CH$_2$Cl$_2$ (100 mL) and DMF (50 mL) at 0° C. was added tert-butyldiphenylsilyl chloride (5.8 mL, 22.4 mmol). The mixture was allowed to stir at rt overnight. The mixture was diluted with CH$_2$Cl$_2$ (100 mL), washed with 1N HCl solution, sat. aq. NaHCO$_3$ and brine, dried over anhydrous Na$_2$SO$_4$, filtered and concentrated in vacuo to afford N-(4-(((tert-butyldiphenylsilyl)oxy)methyl)-2-iodo-5-(methylthio)phenyl)methanesulfonamide. It was used for next step without further purification.

A suspension of crude N-(4-(((tert-butyldiphenylsilyl)oxy)methyl)-2-iodo-5-(methylthio)phenyl)methanesulfonamide, mCPBA (8.9 g, 51.6 mmol) in CH$_2$Cl$_2$ (100 mL) was stirred for 2 h at rt. Sat. aq. NaHCO$_3$ (50 mL) and Na$_2$S$_2$O$_3$ (50 mL) were added and the layers separated. The aqueous layer was extracted with CH$_2$Cl$_2$ (2×100 mL). Combined organic layers were dried over anhydrous Na$_2$SO$_4$, filtered and concentrated under reduced pressure. The residue was purified by flash chromatography over silica gel eluting with EtOAc/hexanes (3/7) to provide N-(4-(((tert-butyldiphenylsilyl)oxy)methyl)-2-iodo-5-(methylsulfonyl)phenyl)methanesulfonamide (8.8 g, 80% yield for two steps). For N-(4-(((tert-butyldiphenylsilyl)oxy)methyl)-2-iodo-5-(methylthio)phenyl)methanesulfonamide: LC-MS m/z 612 [M+H]$^+$. For N-(4-(((tert-butyldiphenylsilyl)oxy)methyl)-2-iodo-5-(methylsulfonyl)phenyl)methanesulfonamide: LC-MS m/z 644 [M+H]$^+$. $^1$H NMR (400 MHz, CDCl$_3$): δ 8.25 (s, 1H), 8.08 (s, 1H), 7.67-7.65 (m, 4H), 7.46-7.37 (m, 6H), 6.77 (s, 1H), 5.05 (s, 2H), 3.11 (s, 3H), 2.83 (s, 3H), 1.12 (s, 9H).

Step 5:

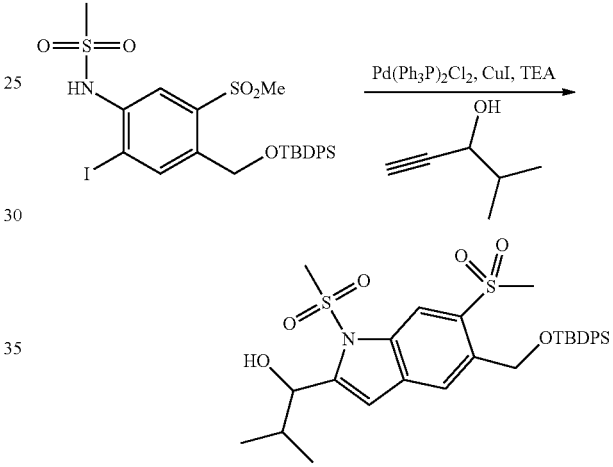

PdCl$_2$(PPh$_3$)$_2$ (277 mg, 0.38 mmol) and CuI (73 mg, 0.38 mmol) were added to a solution of N-(4-(((tert-butyldiphenylsilyl)oxy)methyl)-2-iodo-5-(methylsulfonyl)phenyl)methanesulfonamide (2.45 g, 3.8 mmol) in THF (20 mL) and Et$_3$N (10 mL). The mixture was purged with nitrogen for 10 mins followed by addition of 4-methylpent-1-yn-3-ol (745 mg, 7.6 mmol) and stirred at 65° C. for 8 h. The reaction mixture was diluted with EtOAc (50 mL) and washed with 1N HCl (50 mL). The organic layer was separated, and the aqueous layer was extracted with EtOAc (3×50 mL). The combined organic solution was washed with brine, dried over anhydrous Na$_2$SO$_4$, filtered and concentrated under reduced pressure. The residue was purified by flash chromatography over silica gel eluting with EtOAc/hexanes (3/7) to provide 1-(5-(((tert-butyldiphenylsilyl)oxy)methyl)-1,6-bis(methylsulfonyl)-1H-indol-2-yl)-2-methylpropan-1-ol (2.1 g, 90% yield). LC-MS m/z 614 [M+H]$^+$. $^1$H NMR (400 MHz, CDCl$_3$): δ 8.68 (s, 1H), 7.90 (s, 1H), 7.71-7.67 (s, 4H), 7.46-7.35 (m, 6H), 6.77 (s, 1H), 5.21 (d, J=3.2 Hz, 2H), 6.94 (t, J=6.8 Hz, 1H), 3.22 (s, 3H), 2.90 (s, 3H), 2.61 (d, J=6.8 Hz, 1H), 2.37-2.32 (m, 1H), 1.12 (s, 9H), 1.05 (d, J=6.8 Hz, 3H), 1.03 (d, J=6.8 Hz, 3H). $^{13}$C NMR (100 MHz, CDCl$_3$): δ 147.25, 135.54, 135.28, 135.00, 133.66, 133.00, 132.89, 129.96, 127.85, 121.68, 115.96, 108.69, 72.30, 62.98, 44.33, 41.59, 32.88, 26.89, 20.23, 19.30, 17.61.

Step 6:

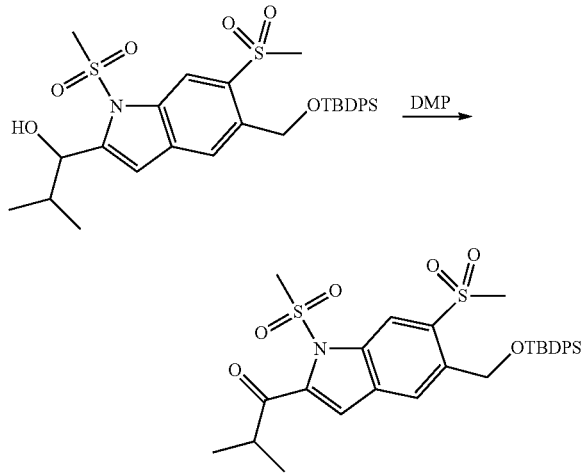

To a stirred solution of 1-(5-(((tert-butyldiphenylsilyl)oxy) methyl)-1,6-bis(methylsulfonyl)-1H-indol-2-yl)-2-methyl-propan-1-ol (2.3 g, 3.8 mmol) in dry CH$_2$Cl$_2$ (25 mL) was added Dess-Martin periodiane (1.94 g, 4.56 mmol) in one portion. The mixture was allowed to stir at rt for 2 h. The reaction was quenched with a solution of Na$_2$S$_2$O$_3$ (5 g in 30 mL H$_2$O) and sat. NaHCO$_3$ solution (40 mL). The mixture was extracted with EtOAc (3×80 mL). The combined organic solution was washed with brine, dried over anhydrous Na$_2$SO$_4$, filtered and concentrated under reduced pressure. The residue was purified by flash chromatography over silica gel eluting with EtOAc/hexanes (2/8) to provide 1-(5-(((tert-butyldiphenylsilyl)oxy)methyl)-1,6-bis(methylsulfonyl)-1H-indol-2-yl)-2-methylpropan-1-one (2.0 g, 86% yield). LC-MS m/z 612 [M+H]$^+$. $^1$H NMR (400 MHz, CDCl$_3$): δ 8.69 (s, 1H), 8.03 (s, 1H), 7.70-7.68 (m, 4H), 7.46-7.36 (m, 6H), 7.22 (s, 1H), 5.20 (s, 2H), 3.80 (s, 3H), 3.36 (m, 1H), 2.89 (s, 3H), 1.29 (d, J=6.8 Hz, 6H), 1.13 (s, 9H). $^{13}$C NMR (100 MHz, CDCl$_3$): δ 197.83, 141.53, 136.69, 136.05, 135.50, 135.04, 132.81, 131.14, 129.99, 127.88, 123.17, 117.12, 114.21, 62.87, 44.19, 44.03, 39.09, 26.88, 19.30, 18.41.

Step 7:

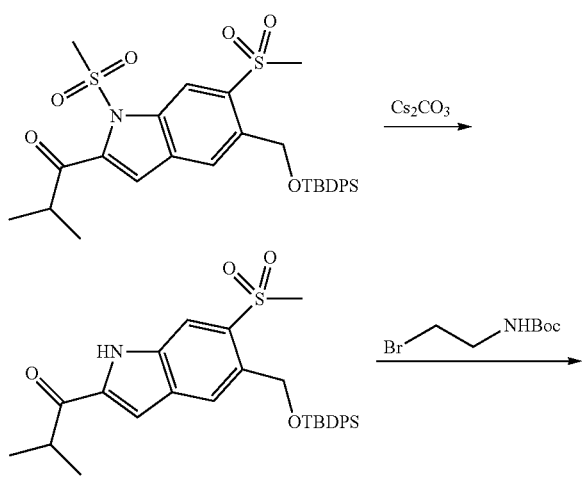

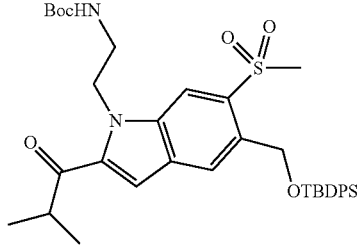

To a stirred solution of 1-(5-(((tert-butyldiphenylsilyl)oxy) methyl)-1,6-bis(methylsulfonyl)-1H-indol-2-yl)-2-methyl-propan-1-one (780 mg, 1.27 mmol) in THF/methanol (15 mL/15 mL) was added Cs$_2$CO$_3$ (1.25 g, 3.83 mmol) in one portion. The mixture was allowed to stir at rt for 4 h and concentrated in vacuo to afford the crude product 1-(5-(((tert-butyldiphenylsilyl)oxy)methyl)-6-(methylsulfonyl)-1H-indol-2-yl)-2-methylpropan-1-one. It was used for the next step reaction without further purification. To a solution of crude 1-(5-(((tert-butyldiphenylsilyl)oxy)methyl)-6-(methylsulfonyl)-1H-indol-2-yl)-2-methylpropan-1-one, 2-(Boc-amino) ethyl bromide (2.8 g, 12 mmol) and tetrabutylammonium iodide (235 mg, 0.63 mmol) in CH$_2$Cl$_2$/toluene (2 mL/4 mL) was added 40% NaOH aq. solution (20 mL). The mixture was allowed to stir at rt for 20 h. The reaction mixture was diluted with CH$_2$Cl$_2$ (40 mL) and washed with H$_2$O (50 mL). The organic layer was separated, and the aqueous layer was extracted with CH$_2$Cl$_2$ (4×50 mL). The combined organic solution was washed with brine, dried over anhydrous Na$_2$SO$_4$, filtered and concentrated under reduced pressure. The residue was purified by flash chromatography over silica gel eluting with CH$_2$Cl$_2$/methanol (95/5) to provide tert-butyl (2-(5-(((tert-butyldiphenylsilyl)oxy)methyl)-2-isobutyryl-6-(methylsulfonyl)-1H-indol-1-yl)ethyl)carbamate (300 mg, 35% yield for two steps). For 1-(5-(((tert-butyldiphenylsilyl)oxy)methyl)-6-(methylsulfonyl)-1H-indol-2-yl)-2-methyl-propan-1-one: LC-MS m/z 556 [M+Na]$^+$. For tert-butyl (2-(5-(((tert-butyldiphenylsilyl)oxy)methyl)-2-isobutyryl-6-(methylsulfonyl)-1H-indol-1-yl)ethyl)carbamate: LC-MS m/z 699 [M+Na]$^+$. $^1$H NMR (400 MHz, CDCl$_3$): δ 8.20 (s, 1H), 7.93 (s, 1H), 7.72 (dd, J$_1$=8.0 Hz, J$_2$=1.6 Hz, 4H), 7.47-7.35 (m, 7H), 5.21 (s, 2H), 4.72 (d, J=6.8 Hz, 2H), 3.55 (d, J=6.8 Hz, 2H), 3.33-3.26 (m, 1H), 3.00 (s, 3H), 1.46 (s, 9H), 1.30 (d, J=6.4 Hz, 3H), 1.28 (d, J=6.4 Hz, 3H), 1.11 (s, 9H).

Step 8:

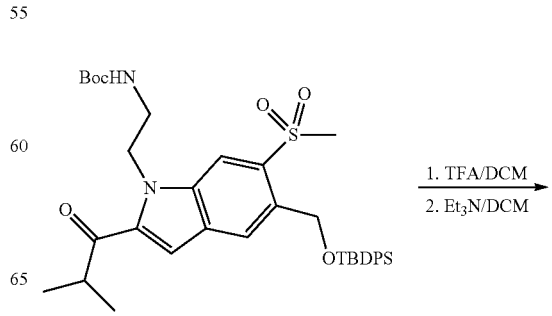

-continued

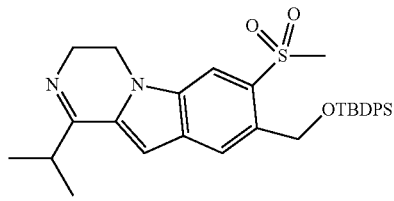

To a solution of tert-butyl (2-(5-(((tert-butyldiphenylsilyl)oxy)methyl)-2-isobutyryl-6-(methylsulfonyl)-1H-indol-1-yl)ethyl)carbamate (250 mg, 0.37 mmol) in $CH_2Cl_2$ (5.0 mL) was added trifluoroacetic acid (1.0 mL) and the mixture was allowed to stir at rt for 1 h. The excess amount of TFA was removed by azeotropic evaporation with toluene under reduced pressure. The residue was redissolved in $CH_2Cl_2$ (5 mL) and $Et_3N$ (0.5 mL) was added. The reaction mixture was stirred at rt for 45 min and concentrated in vacuo. The residue was purified by flash chromatography over silica gel eluting with $CH_2Cl_2$/methanol (98/2) to provide 8-(((tert-butyldiphenylsilyl)oxy)methyl)-1-isopropyl-7-(methylsulfonyl)-3,4-dihydropyrazino[1,2-a]indole (135 mg, 65% yield). LC-MS m/z 559 $[M+H]^+$.

Step 9:

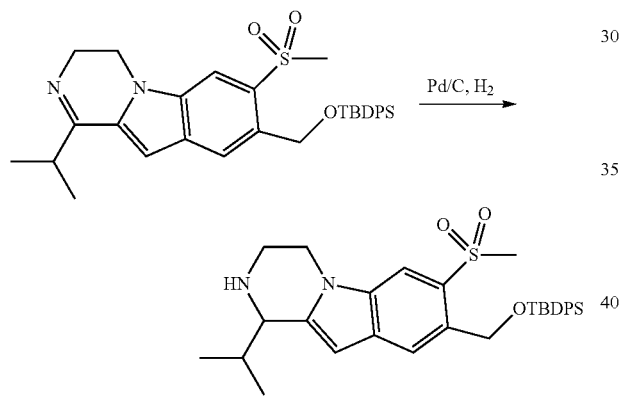

A solution of 8-(((tert-butyldiphenylsilyl)oxy)methyl)-1-isopropyl-7-(methylsulfonyl)-3,4-dihydropyrazino[1,2-a]indole (140 mg, 0.25 mmol), 10% Palladium on charcoal (37 mg, 0.025 mmol) and methanol (5 mL) was stirred at rt under 1 atmosphere of hydrogen for 3 h. The mixture was filtered through Celite® and the Celite® was washed thoroughly with methanol. Combined solvent was removed under reduced pressure to afford 8-(((tert-butyldiphenylsilyl)oxy)methyl)-1-isopropyl-7-(methylsulfonyl)-1,2,3,4-tetrahydropyrazino[1,2-a]indole. It was used directly without further purification. A small portion of product was purified by chromatography for characterization. LC-MS m/z 561 $[M+H]^+$. $^1$H NMR (400 MHz, $CD_3OD$): δ 8.00 (s, 1H), 7.73-7.70 (m, 5H), 7.47-7.40 (m, 6H), 6.36 (s, 1H), 5.20 (d, J=2.0 Hz, 2H), 4.24-4.19 (m, 1H), 4.11-4.00 (m, 2H), 3.52-3.47 (m, 1H), 3.20-3.13 (m, 1H), 3.03 (s, 3H), 2.47-2.39 (m, 1H), 1.18 (d, J=6.8 Hz, 3H), 1.09 (s, 9H), 0.96 (d, J=6.8 Hz, 3H). $^{13}$C NMR (100 MHz, $CDCl_3$): δ 143.06, 135.68, 134.04, 133.31, 131.52, 130.26, 129.79, 129.51, 127.77, 121.39, 111.22, 97.14, 63.76, 59.28, 45.00, 42.94, 42.47, 31.55, 26.94, 19.72, 19.31, 16.49.

Preparation 5

1-(2-chloro-4-(trifluoromethyl)pyrimidin-5-yl)ethanone

Method 1:

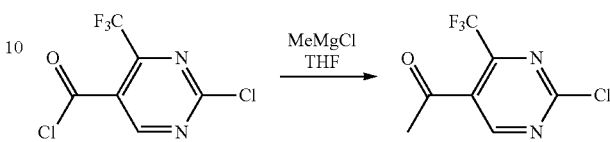

At −78° C., to a solution of 2-chloro-4-(trifluoromethyl)pyrimidine-5-carbonyl chloride (2.45 g, 10 mmol) in dry THF (50 mL) was added MeMgCl THF solution (3.0 M, 4 mL, 12 mmol) slowly and the reaction mixture was allowed to stir at −78° C. for 45 min. Sat. aq. $NH_4Cl$ (2 mL) and water (4 mL) were added. The aqueous layer was extracted with EtOAc (2×10 mL), and the combined extracts were dried with $Na_2SO_4$ and concentrated under reduced pressure. The crude residue was purified by silica chromatography eluting with EtOAc/hexanes (1/9) to give to give 1-(2-chloro-4-(trifluoromethyl)pyrimidin-5-yl)ethanone (675 mg, 30% yield). LC-MS m/z 225 $[M+H]^+$. $^1$H NMR (400 MHz, $CDCl_3$): δ 8.86 (s, 1H), 2.65 (s, 3H).

Method 2:

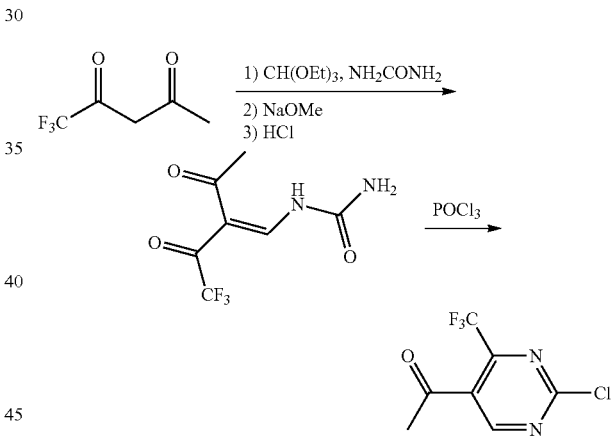

To a solution of 1,1,1-trifluoropentane-2,4-dione (200 g, 1.30 mol) in ethanol (200 mL) were added urea (78 g, 1.30 mol) and $CH(OEt)_3$ (211.5 g, 1.43 mol). The mixture was stirred at 80° C. for 4 h. The resulting slurry was filtered. The filter cake was suspended in methanol (300 mL) and MeONa (77.2 g, 1.43 mol) was added. The mixture was stirred at reflux for 5 h, followed by slow addition of HCl (4N) to pH 3 at rt. The resulting slurry was filtered and the filter cake was dried under vacuum to give compound (E)-1-(2-acetyl-4,4,4-trifluoro-3-oxobut-1-en-1-yl)urea (196 g, 67.3% yield) as a white solid. $^1$H NMR (DMSO-$d_6$ 300 MHz): (WE) δ 10.15-10.13 (m, 1H), 8.64 (s, 1H), 7.69-7.66 (m, 2H), 2.25 (s, 3H). LC-MS MS (ESI) m/z 206.8 $[M-18+H]^+$.

A mixture of compound (E)-1-(2-acetyl-4,4,4-trifluoro-3-oxobut-1-en-1-yl)urea (55 g, 0.25 mol) and $POCl_3$ (240.7 g, 1.57 mol) was stirred at 100° C. for 3 h. The mixture was added dropwise to water (1.5 L) at rt and extracted with EtOAc (3×500 mL). The combined organic layers were washed with brine (500 mL), dried over anhydrous $Na_2SO_4$, filtered and concentrated. The residue was purified by column chromatography eluting with PE/EtOAc 3/1 to give compound 1-(2-chloro-4-(trifluoromethyl)pyrimidin-5-yl)ethanone (23.5 g, 42.7% yield) as a pale-yellow oil. $^1$H NMR (CDCl$_3$ 300 MHz): δ 8.80 (s, 1H), 2.58 (s, 3H). $^{19}$F NMR (920-083-1A CDCl$_3$ 400 MHz): δ-65.5 ppm. $^{13}$C NMR (903-158-1A CDCl$_3$ 400 MHz): δ 195.9, 162.3, 160.1, 153.8 (dd, J=50 Hz), 130.9, 119.5 (dd, J=366 Hz), 30.7.

1-(2-chloro-4-(trifluoromethyl)pyrimidin-5-yl)propan-1-one and 1-(2-chloro-4-(trifluoromethyl)pyrimidin-5-yl)butan-1-one

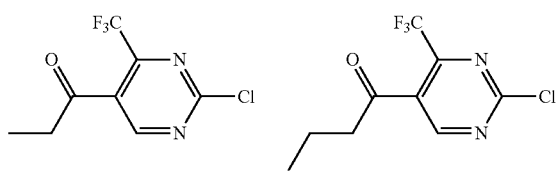 [SMILES: CCC(=O)c1cnc(Cl)nc1C(F)(F)F ; CCCC(=O)c1cnc(Cl)nc1C(F)(F)F]

The title compounds were prepared by method 1 using appropriate Grignard reagents.

Preparation 6

5-bromo-2-chloro-4-(trifluoromethyl)pyrimidine

The title compound was prepared using a modified procedure based on Ondi, L. et al., Eur. J. Org. Chem. 2004, 3714.

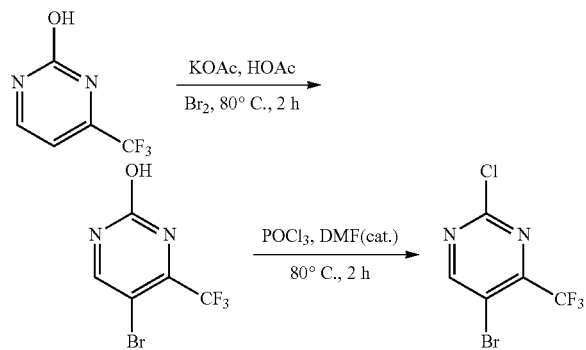

A mixture of 4-(trifluoromethyl)pyrimidin-2-ol (6.05 g, 36.9 mmol), KOAc (10.85 g, 3 eq.), acetic acid (80 mL), and bromine (5.9 g, 1 eq.) was heated for 2 h at 80° C. After being cooled to rt, the mixture was concentrated. The residue was partitioned between EtOAc and water. The aqueous layer was extracted with EtOAc (2×). The combined organic layers were washed with brine, dried over Na$_2$SO$_4$. After filtration and concentration, the crude white solid product (9.38 g, quant. yield) was used for next steps without further purification.

A mixture of 5-bromo-4-(trifluoromethyl)pyrimidin-2-ol (1.35 g, 5.56 mmol), POCl$_3$ (15 mL), and DMF (2 drops, cat. Amount) was heated for 2 h at 80° C. The mixture was cooled to 0° C. by ice/water bath. Some ice pellets were added to the stirred mixture (exotherm). After stirring for 20 min. (the ice added should have melted), some sat. aq. NaHCO$_3$ (c.a. 15 mL) was added carefully to neutralize some acid. The mixture was extracted with hexanes (3×). The combined organic layers were washed with brine, dried over Na$_2$SO$_4$. After filtration and concentration (by rotavapor only! The product is volatile), 5-bromo-2-chloro-4-(trifluoromethyl)pyrimidine, as a clear oil (1.32 g, 91% yield) was used as crude for next steps without further purification.

Example 1

1-(2-(1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone

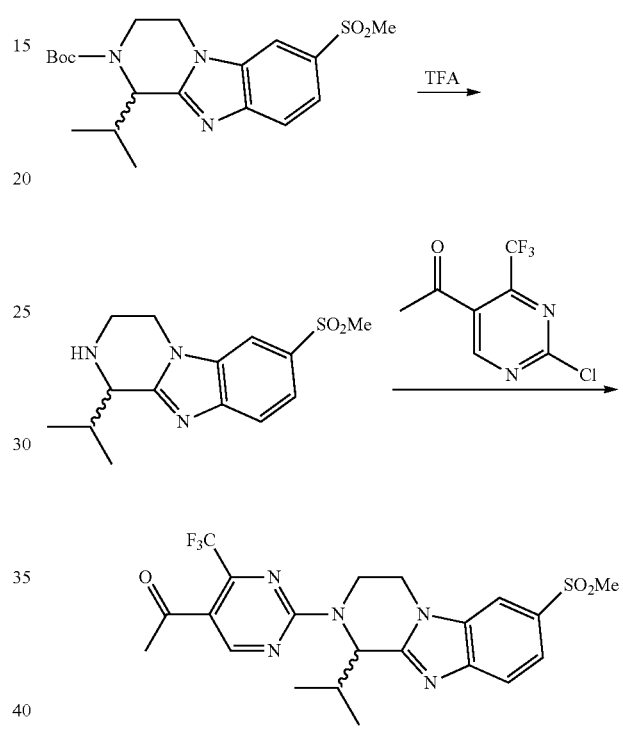

To a solution of tert-butyl 1-isopropyl-7-(methylsulfonyl)-3,4-dihydrobenzo[4,5]imidazo[1,2-a]pyrazine-2(1H)-carboxylate (30 mg, 0.08 mmol, from preparation 1) in CH$_2$Cl$_2$ (1 mL) was added TFA (0.2 mL) under N$_2$. The mixture was stirred at rt for 1 h. The mixture was concentrated to afford 1-isopropyl-7-(methylsulfonyl)-1,2,3,4-tetrahydrobenzo[4,5]imidazo[1,2-a]pyrazine (30 mg, TFA salt) as a yellow solid, which was used for the next step without further purification.

To a solution of 1-isopropyl-7-(methylsulfonyl)-1,2,3,4-tetrahydrobenzo[4,5]imidazo[1,2-a]pyrazine (7.50 mg, 0.03 mmol) in DMSO (1 mL) were added 1-(2-chloro-4-(trifluoromethyl)pyrimidin-5-yl)ethanone (11.5 mg, 0.05 mmol) and DIEA (9.90 mg, 0.08 mmol) under N$_2$. The mixture was stirred at 100° C. for 2 h. The mixture was diluted with water (10 mL) and extracted with EtOAc (3×10 mL). The combined organic layers were washed with brine (10 mL), dried over anhydrous Na$_2$SO$_4$, filtered, concentrated and then purified by preparative HPLC to afford a racemic mixture of 1-(2-(1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone (2.40 mg, 20% yield) as a white solid. LC-MS m/z 482.1 [M+H]$^+$. $^1$H NMR (CD$_3$OD 400 MHz): δ 8.76 (s, 1H), 8.02 (s, 1H), 7.91 (d, J=8.4 Hz, 1H), 7.84-7.83 (m, 1H), 6.15 (d, J=8.0 Hz, 1H), 5.45 (d, J=13.6 Hz, 1H), 4.42-4.36 (m, 1H), 4.20 (brs, 1H), 3.91-3.80 (m, 1H), 3.09 (s, 3H), 2.60-2.46 (m, 4H), 1.34 (d, J=6.8 Hz, 3H), 1.09 (d, J=6.0 Hz, 3H).

Example 2

2-(2-(1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol

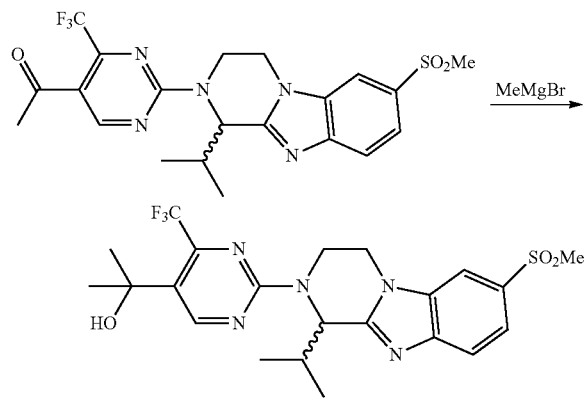

To a solution of 1-(2-(1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone (20 mg, 0.04 mmol, prepared according to example 1) in THF (5 mL) was added MeMgBr (0.6 mL, 0.20 mmol) dropwise at 0° C. under $N_2$. The mixture was stirred at 0° C. for 2 h. The mixture was quenched with sat. aq. $NH_4Cl$ (10 mL) and extracted with $CH_2Cl_2$ (3×10 mL). The combined organic layers were washed with brine (10 mL), dried over anhydrous $Na_2SO_4$, filtered, concentrated and then purified by preparative TLC to afford a racemic mixture of 2-(2-(1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol (6.90 mg, 33% yield) as a white solid. LC-MS m/z 498.2 [M+H]$^+$. $^1$H NMR (CDCl$_3$ 400 MHz): δ 8.79 (s, 1H), 7.99 (d, J=1.2 Hz, 1H), 7.90-7.81 (m, 2H), 6.08 (d, J=8.0 Hz, 1H), 5.35 (dd, J=4.4 and 14.0 Hz, 1H), 4.33-4.27 (m, 1H), 4.25-4.12 (m, 1H), 3.88-3.73 (m, 1H), 3.09 (s, 3H), 2.57-2.48 (m, 1H), 1.99 (s, 1H), 1.66 (s, 6H), 1.32 (d, J=6.8 Hz, 3H), 1.09 (d, J=6.8 Hz, 3H).

Example 3

Ethyl 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate

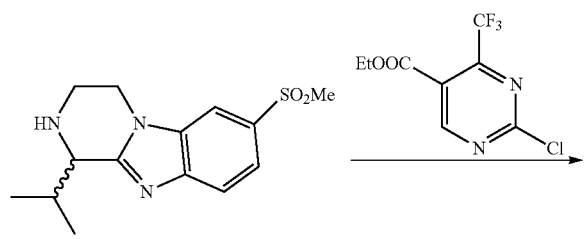

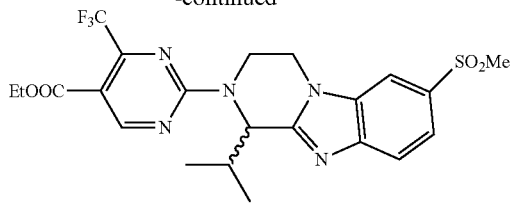

To a solution of 1-isopropyl-7-(methylsulfonyl)-1,2,3,4-tetrahydrobenzo[4,5]imidazo[1,2-a]pyrazine (5.0 mg, 0.02 mmol, prepared according to example 1) in DMSO (1 mL) was added ethyl 2-chloro-4-(trifluoromethyl)pyrimidine-5-carboxylate (8.7 mg, 0.03 mmol), DIEA (6.6 mg, 0.05 mmol) under $N_2$. The mixture was stirred at 100° C. for 2 h. The mixture was diluted with water (5 mL) and extracted with EtOAc (3×5 mL). The combined organic layers were washed with brine (5 mL), dried over anhydrous $Na_2SO_4$, filtered, concentrated and then purified by preparative TLC to afford a racemic mixture of ethyl 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate (5.6 mg, 64% yield) as a white solid. LC-m/z 512.2 [M+H]$^+$. $^1$H NMR (CDCl$_3$ 400 MHz): δ 8.98 (s, 1H), 8.07-7.98 (m, 1H), 7.93-7.83 (m, 2H), 6.16 (d, J=6.4 Hz, 1H), 5.53-5.41 (m, 1H), 4.43-4.32 (m, 3H), 4.28-4.16 (m, 1H), 3.92-3.79 (m, 1H), 3.09 (s, 3H), 2.61-2.46 (m, 1H), 1.40 (s, 3H), 1.38-1.32 (m, 3H), 1.08 (d, J=6.8 Hz, 3H).

Example 4

(2-(1-isopropyl-7-(methylsulfonyl)-3,4-dihydrobenzo[4,5]imidazo[1,2-a]pyrazin-2(1H)-yl)-4-(trifluoromethyl)pyrimidin-5-yl)methanol

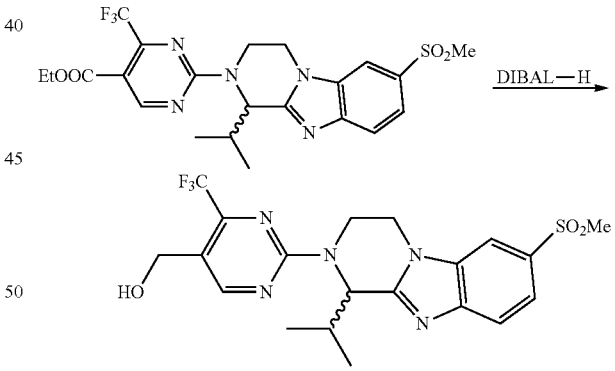

To a solution of ethyl 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate (10 mg, 0.02 mmol, prepared according to example 3) in anhydrous toluene (0.5 mL) was added DIBAL-H (0.2 mL, 0.20 mmol, 1M in THF) dropwise at −78° C. under $N_2$. The mixture was stirred at −78° C. for 2 h. Sat. $NH_4Cl$ (5 mL) at −78° C. was added to the mixture, which was then extracted with EtOAc (3×5 mL). The combined organic layers were washed with brine (5 mL), dried over anhydrous $Na_2SO_4$, filtered, concentrated and then purified by basic preparative HPLC to afford a racemic mixture of (2-(1-isopropyl-7-(methylsulfonyl)-3,4-dihydrobenzo[4,5]imidazo[1,2-a]pyrazin-2(1H)-yl)-4-

(trifluoromethyl)pyrimidin-5-yl)methanol (5.80 mg, 63% yield) as a white solid. LC-MS m/z 470.1 [M+H]+. 1H NMR (CDCl3 400 MHz): δ 8.68 (s, 1H), 8.01 (s, 1H), 7.93-7.81 (m, 2H), 6.11 (d, J=8.0 Hz, 1H), 5.38 (dd, J=5.2 Hz, J=14.4 Hz, 1H), 4.74 (s, 2H), 4.38-4.30 (m, 1H), 4.25-4.15 (m, 1H), 3.86-3.76 (m, 1H), 3.10 (s, 3H), 2.56-2.47 (m, 1H), 1.32 (d, J=6.8 Hz, 3H), 1.08 (d, J=6.8 Hz, 3H).

Example 5

2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide

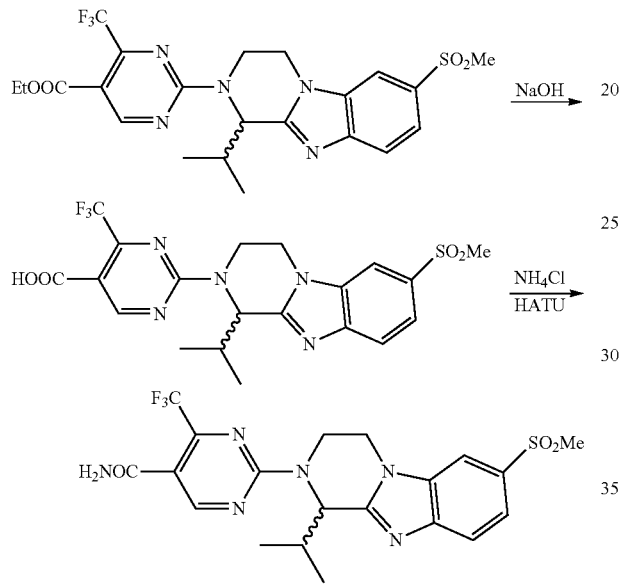

To a solution of ethyl 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate (20 mg, 0.04 mmol, prepared according to example 3) in MeOH (3 mL), H2O (1 mL) was added NaOH (4.7 mg, 0.12 mmol). The mixture was stirred at rt overnight. The mixture was diluted with water (10 mL), acidified with 1N HCl to pH=3-4 and extracted with EtOAc (3×10 mL). The combined organic layers were washed with brine (10 mL), dried over anhydrous Na2SO4, filtered, and concentrated to afford 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid (20 mg, 100% yield) as a yellow solid, which was used for the next step without further purification.

To a solution of 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid (50 mg, 0.10 mmol) in DMF (10 mL) was added HATU (59 mg, 0.16 mmol), NH4Cl (100 mg, 1.97 mmol), Et3N (30 mg, 0.31 mmol) under N2. The mixture was stirred at rt for 2 h. The mixture was diluted with water (15 mL) and extracted with EtOAc (3×15 mL). The combined organic layers were washed with brine (15 mL), dried over anhydrous Na2SO4, filtered, concentrated and purified by basic preparative HPLC to afford a racemic mixture of 2-(1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide (13.4 mg, 27% yield) as a white solid. LC-MS m/z 483.1 [M+H]+. 1H NMR (CDCl3 400 MHz): δ 8.77 (s, 1H), 8.02 (s, 1H), 7.92-7.83 (m, 2H), 6.12 (d, J=8.4 Hz, 1H), 8.78 (brs, 2H), 5.48-5.38 (m, 1H), 4.41-4.34 (m, 1H), 4.25-4.12 (m, 1H), 3.87-3.77 (m, 1H), 3.10 (s, 3H), 2.52 (brs, 1H), 1.34 (d, J=6.8 Hz, 3H), 1.10 (d, J=6.8 Hz, 3H).

Example 6

(R)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone and (S)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone

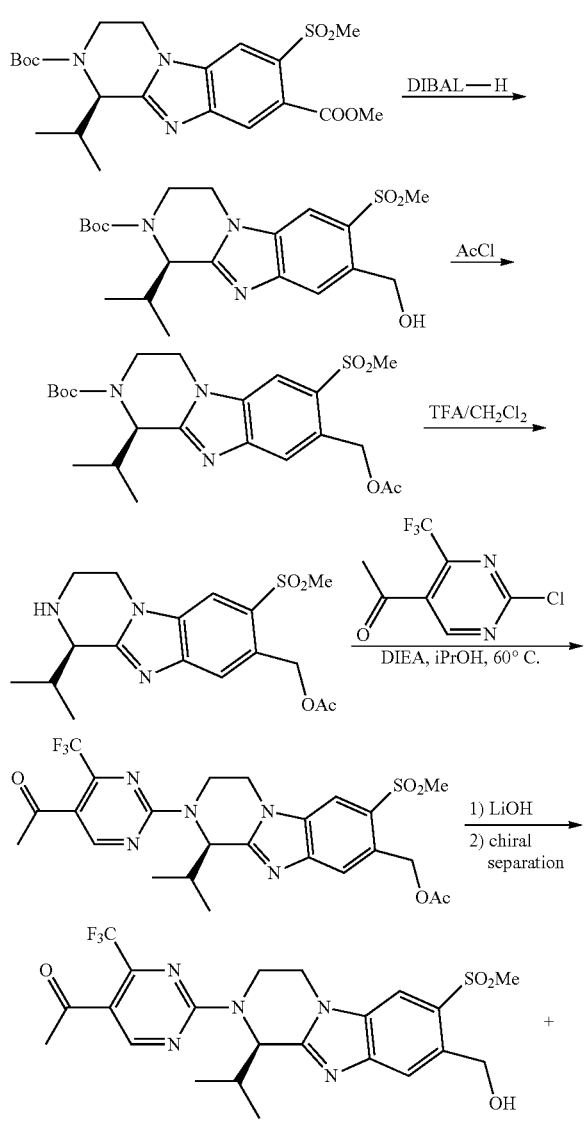

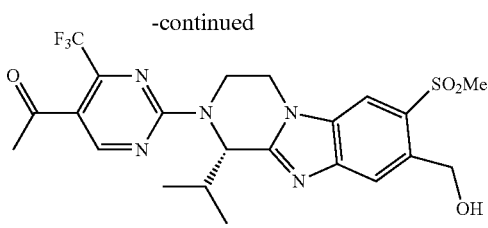

Racemization occurred during the course of synthesis

Step 1

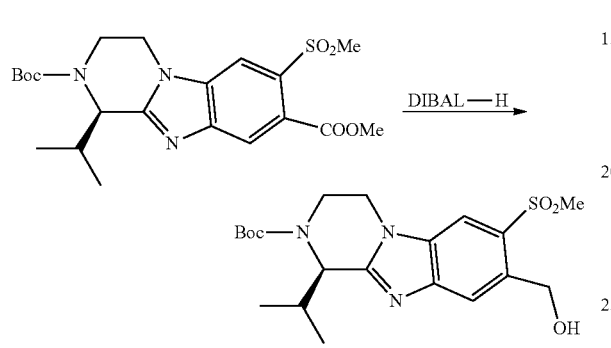

To a 50 mL three-necked flask containing (R)-2-tert-butyl 8-methyl 1-isopropyl-7-(methylsulfonyl)-3,4-dihydrobenzo[4,5]imidazo[1,2-a]pyrazine-2,8(1H)-dicarboxylate (250 mg, 0.554 mmol, from preparation 2) in DCM (5 mL) was added DIBAL-H (1.70 mL, 1.67 mmol, 1.0 M in toluene) dropwise at −78° C. under N$_2$. The mixture was stirred at −78° C. for 3 h. The reaction was quenched with sat. aq. ammonium chloride (10 mL) at −78° C. The aqueous layer was extracted with EtOAc (3×20 mL). The combined organic layers were washed with water (15 mL) and brine, and then dried over anhydrous Na$_2$SO$_4$. The mixture was filtered and the filtrate was evaporated under reduced pressure. The residue was purified by column chromatography on silica gel eluting with PE: EtOAc 8:1~2:1 to give (R)-tert-butyl 8-(hydroxymethyl)-1-isopropyl-7-(methylsulfonyl)-3,4-dihydrobenzo[4,5]imidazo[1,2-a]pyrazine-2(1H)-carboxylate (175 mg, 74.1% yield) as a white solid.

Step 2

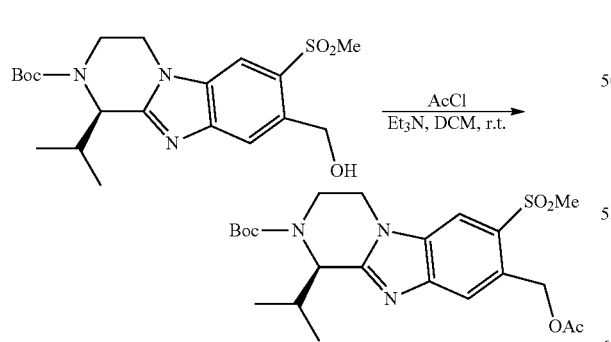

To a 50 mL round-bottomed flask containing (R)-tert-butyl 8-(hydroxymethyl)-1-isopropyl-7-(methylsulfonyl)-3,4-dihydrobenzo[4,5]imidazo[1,2-a]pyrazine-2(1H)-carboxylate (236 mg, 0.558 mmol) in CH$_2$Cl$_2$ (5 mL) was added Et$_3$N (169 mg, 1.67 mmol) and AcCl (87 mg, 1.12 mmol) under N$_2$. The mixture was stirred at rt for 10 min. The reaction was quenched with water (20 mL). The aqueous layer was extracted with CH$_2$Cl$_2$ (3×20 mL). The combined organic layers were washed with water (25 mL) and brine, and then dried over anhydrous Na$_2$SO$_4$. The mixture was filtered and the filtrate was evaporated under reduced pressure. The residue was purified by column chromatography on silica gel eluting with PE: EtOAc 8:1-4:1 to give (R)-tert-butyl 8-(acetoxymethyl)-1-isopropyl-7-(methylsulfonyl)-3,4-dihydrobenzo[4,5]imidazo[1,2-a]pyrazine-2(1H)-carboxylate (210 mg, 81.1% yield) as a yellow solid.

Step 3

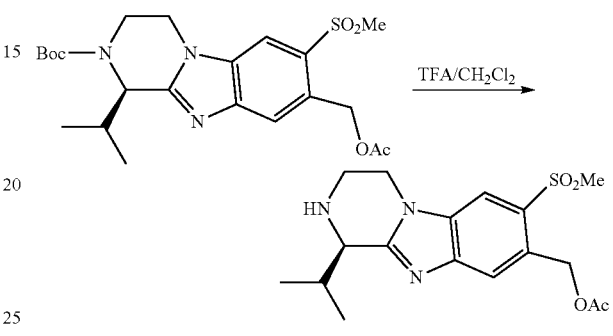

TFA (1 mL) was added dropwise to a solution containing (R)-tert-butyl 8-(acetoxymethyl)-1-isopropyl-7-(methylsulfonyl)-3,4-dihydrobenzo[4,5]imidazo[1,2-a]pyrazine-2(1H)-carboxylate (210 mg, 0.452 mmol) in DCM (5 mL) at rt. The mixture was stirred at rt for 2 h. TLC showed compound 3 was consumed completely. The solvents were removed under reduced pressure at 30° C. and then DCM (10 mL) was added. The mixture was neutralized by sat. NaHCO$_3$ solution to pH=8. The mixture was extracted with DCM (3×20 mL) and the combined organic layers were dried over anhydrous Na$_2$SO$_4$, filtered and concentrated under vacuum to afford (R)-(1-isopropyl-7-(methylsulfonyl)-1,2,3,4-tetrahydrobenzo[4,5]imidazo[1,2-a]pyrazin-8-yl)methyl acetate (160 mg, 97.1% yield) as a white solid, which was used directly for the next step without further purification.

Step 4

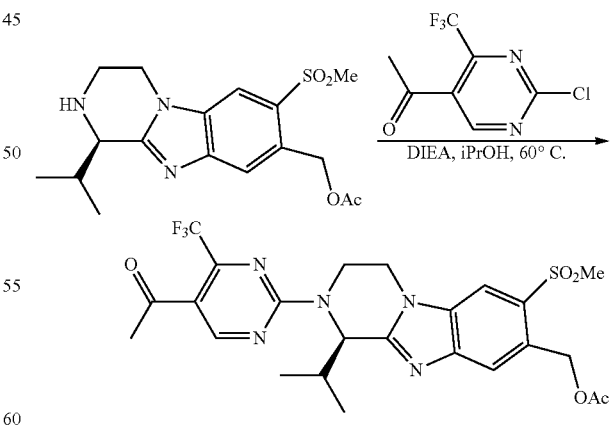

To a solution of (R)-(1-isopropyl-7-(methylsulfonyl)-1,2,3,4-tetrahydrobenzo[4,5]imidazo[1,2-a]pyrazin-8-yl)methyl acetate (160 mg, 0.456 mmol) in $^i$PrOH (4 mL) and DCM (2 mL) was added 1-(2-chloro-4-(trifluoromethyl)pyrimidin-5-yl)ethanone (306 mg, 1.37 mmol) and DIEA (353 mg, 2.74 mmol). The mixture was stirred at 60° C. overnight. Water (5 mL) was added to the mixture and the aqueous layer was extracted with EtOAc (2×10 mL). The combined organic layers were washed with water (2×10 mL) and brine, dried over anhydrous Na$_2$SO$_4$, filtered and concentrated under reduced pressure. The residue was purified by preparative TLC to afford (R)-(2-(5-acetyl-4-(trifluoromethyl)pyrimidin-2-yl)-1-isopropyl-7-(methylsulfonyl)-1,2,3,4-tetrahydrobenzo[4,5]imidazo[1,2-a]pyrazin-8-yl)methyl acetate (150 mg, 44.4% yield) as a yellow oil.

Step 5

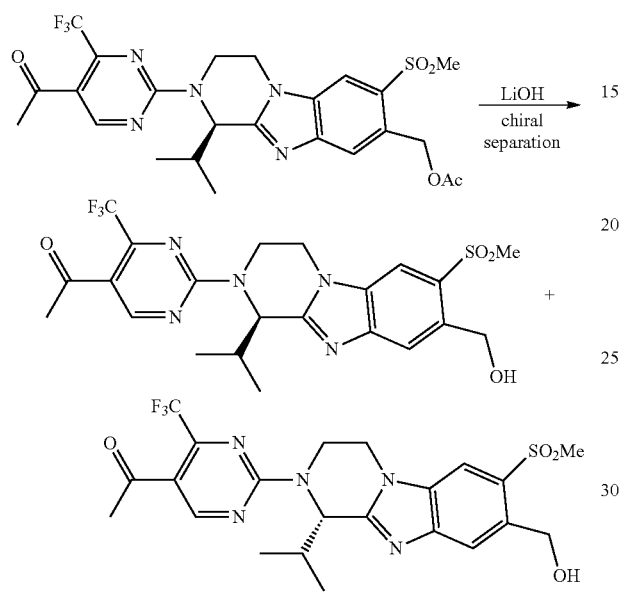

To a solution of (R)-(2-(5-acetyl-4-(trifluoromethyl)pyrimidin-2-yl)-1-isopropyl-7-(methylsulfonyl)-1,2,3,4-tetrahydrobenzo[4,5]imidazo[1,2-a]pyrazin-8-yl)methyl acetate (100 mg, 0.181 mmol) in THF (2 mL) and H$_2$O (2 mL) was added LiOH (38 mg, 0.905 mmol). The mixture was stirred at rt for 10 min. The mixture was extracted with EtOAc (3×10 mL). The combined organic layers were washed with brine, dried over anhydrous Na$_2$SO$_4$, filtered and concentrated under vacuum. The residue was purified by basic preparative HPLC to afford the crude product (53.1 mg, 55.9% yield). The crude product was separated by SFC to afford (R)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone (32.90 mg, isomer 1) as a white solid and (S)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone (16.90 mg, isomer 2) as a white solid. Isomer 1: (R)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone. Analytical chiral HPLC: t$_R$=7.280 min in 15 min chromatography (Method: AS-H_5_5_40_2.35 ML). LC-MS m/z 512.1 [M+H]$^+$. $^1$H NMR (CD$_3$OD 400 MHz): δ 9.00 (s, 1H), 8.23 (s, 1H), 7.95 (s, 1H), 6.11-6.07 (m, 1H), 5.49-5.32 (m, 1H), 5.10 (s, 2H), 4.54 (dd, J=3.6 Hz and 12.4 Hz, 1H), 4.24 (dt, J=4.8 and 12.0 Hz, 1H), 3.98-3.90 (m, 1H), 3.25 (s, 3H), 2.61-2.57 (m, 1H), 2.56 (s, 3H), 1.29 (d, J=6.8 Hz, 3H), 1.07 (d, J=6.8 Hz, 3H). Isomer 2: (S)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanone Analytical chiral HPLC: t$_R$=8.485 min in 15 min chromatography (Method: AS-H_5_5_40_2.35 ML). LC-MS m/z 512.1 [M+H]$^+$. $^1$H NMR (CD$_3$OD 400 MHz): δ 9.00 (s, 1H), 8.24 (s, 1H), 7.96 (s, 1H), 6.12-6.08 (m, 1H), 5.48-5.31 (m, 1H), 5.11 (s, 2H), 4.56 (dd, J=3.6 Hz and 12.4 Hz, 1H), 4.24 (dt, J=4.8 and 12.0 Hz, 1H), 3.98-3.91 (m, 1H), 3.26 (s, 3H), 2.61-2.58 (m, 1H), 2.56 (s, 3H), 1.29 (d, J=6.0 Hz, 3H), 1.07 (d, J=6.8 Hz, 3H).

Example 7

(R)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol and (S)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol

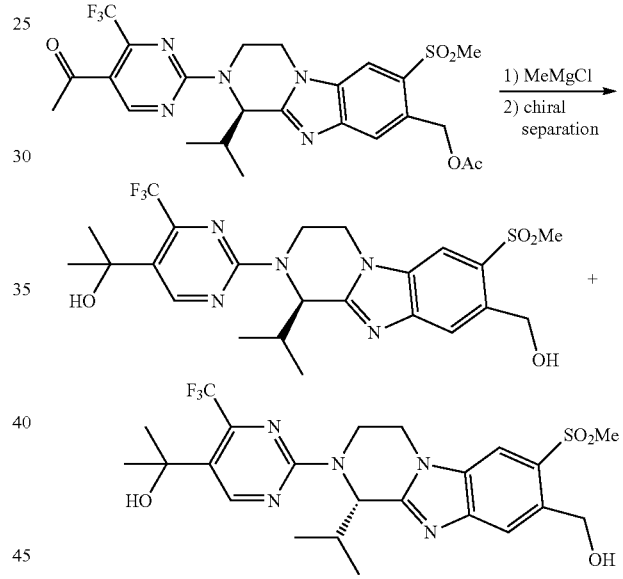

Starting material partially racemized (R)-(2-(5-acetyl-4-(trifluoromethyl)pyrimidin-2-yl)-1-isopropyl-7-(methylsulfonyl)-1,2,3,4-tetrahydrobenzo[4,5]imidazo[1,2-a]pyrazin-8-yl)methyl acetate (150 mg, 0.271 mmol, partially racemized) was added MeMgCl (3.0 M in toluene, 0.50 mL, 1.36 mmol) at −10° C. The mixture was stirred at −10° C. for 3 h. Sat. NH$_4$Cl solution (10 mL) was added at −10° C. and the mixture was filtered. The aqueous layer was extracted with DCM (3×20 mL). The combined organic layers were washed with brine, dried over anhydrous Na$_2$SO$_4$, filtered and concentrated under reduced pressure. The residue was purified by preparative TLC to give the racemic mixture (65.0 mg, 45.5% yield) as a white solid. The racemic mixture was purified by SFC separation to give (R)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol (16.20 mg, isomer 1) and (S)-2-(2-(8-(hydroxymethyl)-1-isopropyl-7-(methylsulfonyl)-3,4-dihydrobenzo[4,5]imidazo[1,2-a]

pyrazin-2(1H)-yl)-4-(trifluoromethyl)pyrimidin-5-yl)propan-2-ol (9.10 mg, isomer 2) as white solids.

Isomer 1: (R)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol. Analytical chiral HPLC: $t_R$=8.600 min in 15 min chromatography (Method: OD-H_3_5_40_2.35 ML). LC-MS MS (ESI) m/z 528.2 [M+H]$^+$. $^1$H NMR (CD$_3$OD 400 MHz): δ 8.87 (s, 1H), 8.20 (s, 1H), 7.93 (s, 1H), 6.02 (d, J=8.0 Hz, 1H), 5.31 (dd, J=5.2 and 14.4 Hz, 1H), 5.09 (s, 2H), 4.50-4.46 (m, 1H), 4.23-4.16 (m, 1H), 3.90-3.83 (m, 1H), 3.24 (s, 3H), 2.59-2.51 (m, 1H), 1.59 (s, 6H), 1.26 (d, J=6.8 Hz, 3H), 1.05 (d, J=6.8 Hz, 3H).

Isomer 1 can be recrystallized as a hydrochloric acid salt according to following procedure:

To a solution of (R)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol (52 mg, 0.1 mmol) in methanol (2 mL) was added acetyl chloride (7 μL, 0.1 mmol) and the mixture was stirred at rt for 4 h. Methanol was removed under reduced pressure. The crude resultant was dissolved into mixture of acetone and EtOAc (2.5 mL/2.5 mL) followed by filtration. To the filtrate, hexanes (0.4 mL) were slowly added with intermittent heating. Leave the solution stay at rt until crystals form. The crystal was collected by filtration. m.p. 176-179° C.

LC-MS m/z 528 [M+H]$^+$. $^1$H NMR (400 MHz, CD$_3$OD): δ 8.95 (s, 1H), 8.48 (s, 1H), 8.17 (s, 1H), 6.28 (d, J=8.0 Hz, 1H), 5.43 (dd, J$_1$=14.4 Hz, J$_2$=4.8 Hz, 1H), 5.15 (s, 2H), 4.70 (dd, J$_1$=12.8 Hz, J$_2$=3.6 Hz, 1H), 4.34 (td, J$_1$=12.0 Hz, J$_2$=4.8 Hz, 1H), 3.92 (dddd, J$_1$=14.4 Hz, J$_2$=12.8 Hz, J$_3$=4.8 Hz, 1H), 3.26 (s, 3H), 2.70-2.62 (m, 1H), 1.60 (s, 6H), 1.31 (d, J=6.8 Hz, 3H), 1.13 (d, J=6.8 Hz, 3H).

Isomer 2: (S)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol. Analytical chiral HPLC: $t_R$=6.680 min in 15 min chromatography (Method: OD-H_3_5_40_2.35 ML). LC-MS MS (ESI) m/z 528.2 [M+H]$^+$. $^1$H NMR (CD$_3$OD 400 MHz): δ 8.87 (s, 1H), 8.22 (s, 1H), 7.94 (s, 1H), 6.03 (d, J=8.0 Hz, 1H), 5.31 (dd, J=4.4 and 14.0 Hz, 1H), 5.09 (s, 2H), 4.51-4.47 (m, 1H), 4.23-4.16 (m, 1H), 3.91-3.83 (m, 1H), 3.25 (s, 3H), 2.60-2.51 (m, 1H), 1.59 (s, 6H), 1.26 (d, J=6.8 Hz, 3H), 1.05 (d, J=6.8 Hz, 3H).

Alternatively, a racemic mixture of 2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol were prepared by following method.

(rac)-2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol

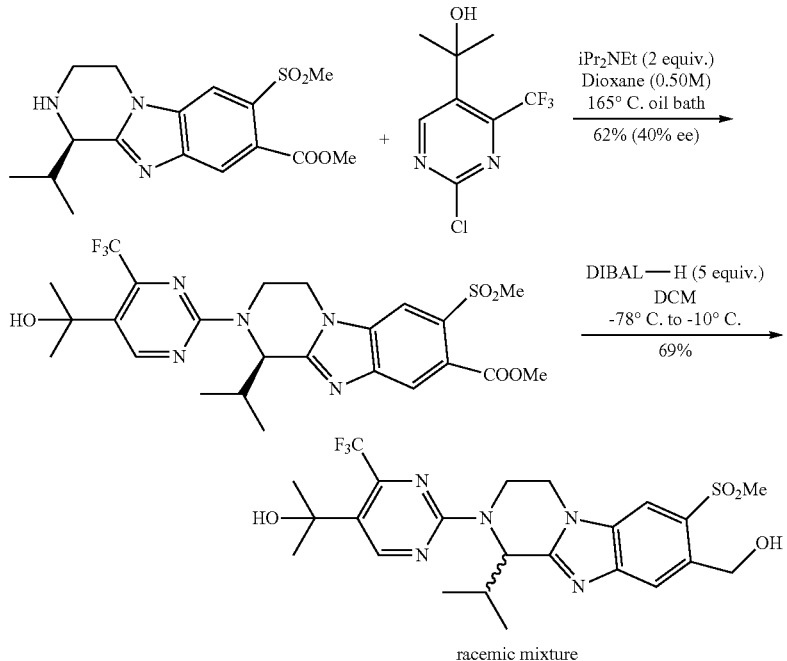

racemic mixture (R)-methyl-1-isopropyl-7-(methylsulfonyl)-1,2,3,4-tetrahydrobenzo[4,5]imidazo[1,2-a]pyrazine-8-carboxylate (224 mg, 0.639 mmol) and 2-(2-chloro-4-(trifluoromethyl)pyrimidin-5-yl)propan-2-ol (192 mg, 0.799 mmol) were combined in a small vial and azeotroped with benzene to remove any residual water. A mixture of dioxane (1 mL) and iPr$_2$NEt (0.22 mL, 1.28 mmol) was degassed with N$_2$ for 10 minutes. This mixture was then added to the reaction vial and sealed with a Teflon® coated cap which was then wrapped with Teflon® tape. The resulting suspension was then placed in a 165° C. silicone oil bath at which point the mixture became homogeneous. The resulting solution stirred at 165° C. for 21 h. After the solvents were removed by rotovap, the mixture was purified using ISCO FCC, eluting with 50% EtOAc in Hexanes to obtain 219 mg of (R)-methyl-2-(5-(2-hydroxypropan-2-yl)-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate as a white solid (62% yield, 40% ee).

LC-MS MS (ESI) m/z 556.0 [M+H]$^+$. $^1$H NMR (CD$_3$OD, 400 MHz): δ 8.88 (s, 1H), 8.28 (s, 1H), 7.98 (s, 1H), 6.05 (d,

J=8.0 Hz, 1H), 5.32 (dd, J=4.8 and 14.0 Hz, 1H), 4.53 (dd, J=3.2 and 12 Hz, 1H), 4.27-4.20 (m, 1H), 3.95 (s, 3H), 3.90-3.83 (m, 1H), 3.41 (s, 3H), 2.61-2.52 (m, 1H), 1.59 (s, 6H), 1.27 (d, J=6.8 Hz, 3H), 1.06 (d, J=6.8 Hz, 3H).

To a solution of (R)-methyl-2-(5-(2-hydroxypropan-2-yl)-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (109 mg, 0.196 mmol) in DCM (4 mL) was added a solution of DIBAL-H in DCM (0.98 mL of a 1.0 M solution, 0.98 mmol) dropwise at −78° C. The reaction slowly warmed to −10° C. over approximately 1 h, at which point 1 mL of MeOH was added to quench the excess DIBAL-H. Sat. aq. Rochelle salt (potassium sodium tartrate ($KNaC_4H_4O_6$)) solution (5 mL) and DCM (5 mL) were added and the mixture stirred vigorously for 15 min. The DCM layer was separated and the aqueous layer was extracted with DCM (2×5 mL). The DCM layers were combined, dried using $Na_2SO_4$ and evaporated to give the crude product. Purification using ISCO FCC eluting with 70% EtOAc in Hexanes gave 71 mg of 2-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-2-ol as a racemic mixture (69%). LC-MS MS (ESI) m/z 528.25 [M+H]+. 1H NMR ($CDCl_3$, 400 MHz): δ 8.72 (s, 1H), 8.05 (s, 1H), 7.80 (s, 1H), 6.01 (d, J=7.6 Hz, 1H), 5.27 (d, J=4.4 and 14.0 Hz, 1H), 5.00-4.86 (m, 2H), 4.26-4.08 (m, 2H), 3.74-3.67 (m, 1H), 3.15 (s, 3H), 3.15-3.10 (m, 1H), 2.47-2.40 (m, 1H), 1.96 (b, 1H), 1.59 (s, 6H), 1.23 (d, J=6.8 Hz, 3H), 1.10 (d, J=6.8 Hz, 3H).

2-(2-chloro-4-(trifluoromethyl)pyrimidin-5-yl)propan-2-ol was prepared as following:

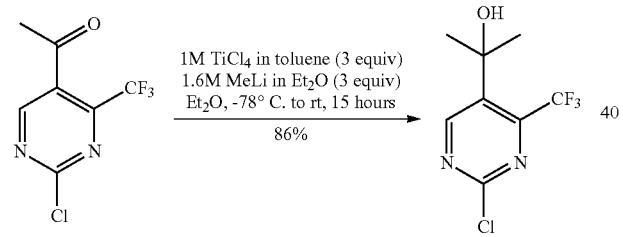

To a 1.0 M solution of $TiCl_4$ in toluene (6.67 mL, 6.67 mmol) was added a 1.6 M solution of MeLi in $Et_2O$ (4.18 mL, 6.69 mmol) dropwise a −78° C. (dry ice/acetone bath). The resulting dark solution stirred at −78° C. for 30 minutes. A solution of 1-(2-chloro-4-(trifluoromethyl)pyrimidin-5-yl)ethanone (500 mg, 2.23 mmol) in $Et_2O$ (3 mL) was added dropwise at −78° C. The reaction was slowly allowed to warm to rt in the dewar over a 15 h period. TLC analysis showed complete conversion to the more polar tertiary alcohol product. The mixture was then cooled to 0° C. and quenched with sat. aq. $NH_4Cl$ (10 mL) followed by EtOAc (10 mL) for the workup. The EtOAc layer was separated and the aqueous layer was extracted with EtOAc (2×10 mL). The EtOAc layers were combined, dried using $Na_2SO_4$ and evaporated to give the crude product. Purification using ISCO FCC eluting with 20% EtOAc in Hexanes gave 459 mg of 2-(2-chloro-4-(trifluoromethyl)pyrimidin-5-yl)propan-2-ol (86% yield) as a colorless oil. LC-MS MS (ESI) m/z 241.12 [M+H]+. 1H NMR ($CDCl_3$, 400 MHz): δ 9.05 (s, 1H), 1.99 (s, 1H), 1.67 (s, 6H).

Example 8

1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)ethanol
(4 isomers)

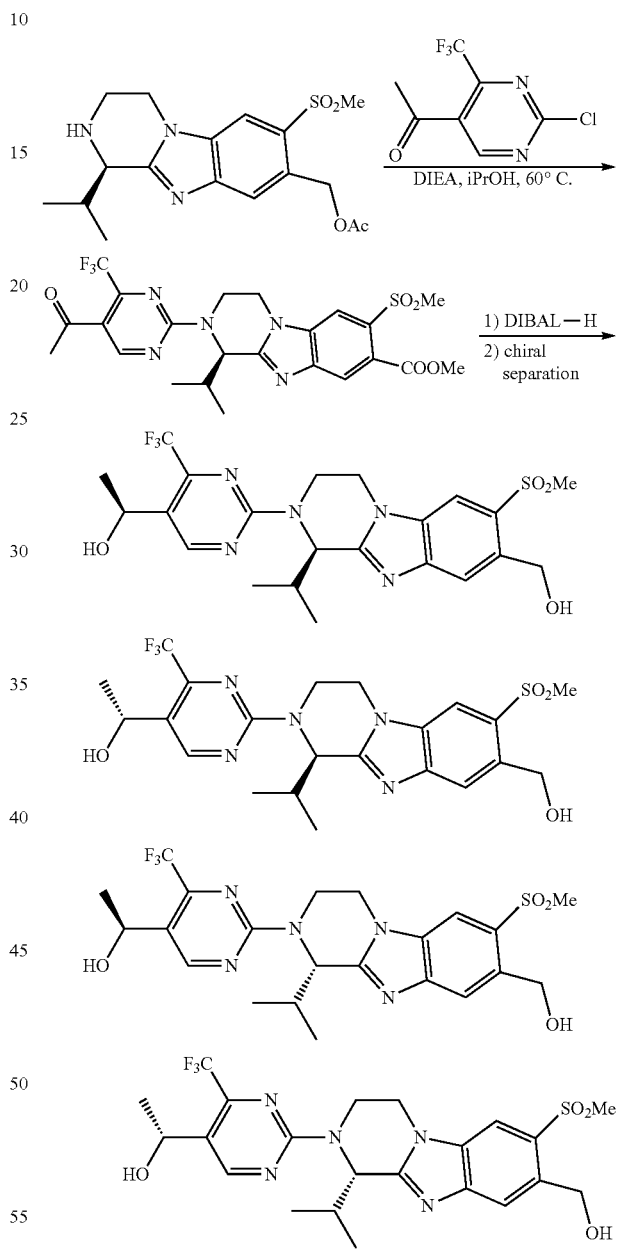

Racemization occurred during the course of synthesis

To a solution of (R)-methyl 1-isopropyl-7-(methylsulfonyl)-1,2,3,4-tetrahydrobenzo[4,5]imidazo[1,2-a]pyrazine-8-carboxylate (220 mg, 0.627 mmol) in *i*PrOH (4 mL) and DCM (2 mL) was added 1-(2-chloro-4-(trifluoromethyl)pyrimidin-5-yl)ethanone (421 mg, 1.88 mmol) and DIEA (485 mg, 3.76 mmol). The mixture was stirred at 60° C. overnight. Water (5 mL) was added to the mixture and the aqueous layer was extracted with EtOAc (2×10 mL). The combined organic layers were washed with water (2×10 mL) and brine, dried over anhydrous Na$_2$SO$_4$, filtered and concentrated under reduced pressure. The residue was purified by preparative TLC to afford (R)-methyl 2-(5-acetyl-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (150 mg, 44.4% yield) as a yellow solid.

To a 50 mL three-necked flask containing (R)-methyl 2-(5-acetyl-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (150 mg, 0.278 mmol) in DCM (3 mL) was added DIBAL-H (1.10 mL, 1.11 mmol, 1.0 M in toluene) dropwise at −78° C. under N$_2$. The mixture was stirred at −78° C. for 3 h. Sat. NH$_4$Cl solution (10 mL) was added at −78° C. and the mixture was filtered. The aqueous layer was extracted with DCM (3×20 mL). The combined organic layers were washed with brine, dried over anhydrous Na$_2$SO$_4$, filtered and concentrated under reduced pressure. The residue was purified by preparative TLC to give the racemic mixture (81.0 mg, 56.7% yield) as a white solid. The racemic mixture was purified by SFC separation to give isomer 1 (10.60 mg, 47.1% yield) as a white solid, isomer 2 (7.10 mg, 31.6% yield) as a white solid, isomer 3 (4.70 mg, 26.1% yield) as a white solid and isomer 4 (6.00 mg, 33.3% yield) as a white solid.

Isomer 1

Analytical chiral HPLC: t$_R$=8.397 min in 15 min chromatography (Method: OD-H_5_5_40_2.35 ML). LC-MS MS (ESI) m/z 514.1 [M+H]$^+$. $^1$H NMR (CD$_3$OD 400 MHz): δ 8.89 (s, 1H), 8.20 (s, 1H), 7.93 (s, 1H), 6.03 (d, J=8.0 Hz, 1H), 5.32 (dd, J=4.4 and 14.4 Hz, 1H), 5.11-5.08 (m, 3H), 4.50-4.46 (m, 1H), 4.28-4.16 (m, 1H), 3.90-3.83 (m, 1H), 3.24 (s, 3H), 2.72-2.39 (m, 1H), 1.42 (d, J=6.4 Hz, 3H), 1.26 (d, J=6.8 Hz, 3H), 1.04 (d, J=6.8 Hz, 3H).

Isomer 2

Analytical chiral HPLC: t$_R$=6.700 min in 15 min chromatography (Method: AS-H_5_5_40_2.35 ML). LC-MS MS (ESI) m/z 514.1 [M+H]$^+$. $^1$H NMR (CD$_3$OD 400 MHz): δ 8.89 (s, 1H), 8.21 (s, 1H), 7.93 (s, 1H), 6.03 (d, J=8.0 Hz, 1H), 5.32 (dd, J=4.4 and 14.4 Hz, 1H), 5.11-5.08 (m, 3H), 4.50-4.46 (m, 1H), 4.23-4.16 (m, 1H), 3.95-3.79 (m, 1H), 3.25 (s, 3H), 2.59-2.51 (m, 1H), 1.42 (d, J=6.0 Hz, 3H), 1.26 (d, J=6.4 Hz, 3H), 1.04 (d, J=6.4 Hz, 3H).

Isomer 3

Analytical chiral HPLC: t$_R$=7.666 min in 15 min chromatography (Method: AS-H_5_5_40_2.35 ML). LC-MS MS (ESI) m/z 514.2 [M+H]$^+$. $^1$H NMR (CD$_3$OD 400 MHz): δ 8.89 (s, 1H), 8.22 (s, 1H), 7.94 (s, 1H), 6.03 (d, J=8.0 Hz, 1H), 5.32 (dd, J=4.0 and 14.0 Hz, 1H), 5.11-5.08 (m, 3H), 4.51-4.47 (m, 1H), 4.24-4.15 (m, 1H), 3.91-3.84 (m, 1H), 3.25 (s, 3H), 2.61-2.43 (m, 1H), 1.42 (d, J=6.0 Hz, 3H), 1.26 (d, J=6.8 Hz, 3H), 1.05 (d, J=6.8 Hz, 3H).

Isomer 4

Analytical chiral HPLC: t$_R$=9.621 min in 15 min chromatography (Method: OD-H_5_5_40_2.35 ML). LC-MS MS (ESI) m/z 514.1 [M+H]$^+$. $^1$H NMR (CD$_3$OD 400 MHz): δ 8.89 (s, 1H), 8.21 (s, 1H), 7.93 (s, 1H), 6.03 (d, J=8.0 Hz, 1H), 5.32 (dd, J=4.0 and 14.0 Hz, 1H), 5.11-5.08 (m, 3H), 4.50-4.23 (m, 1H), 4.23-4.15 (m, 1H), 3.91-3.80 (m, 1H), 3.25 (s, 3H), 2.59-2.51 (m, 1H), 1.42 (d, J=6.4 Hz, 3H), 1.26 (d, J=6.8 Hz, 3H), 1.05 (d, J=6.8 Hz, 3H).

Example 9

(R)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)

propan-1-one and (S)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl) propan-1-one

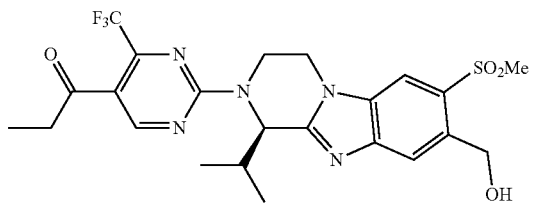

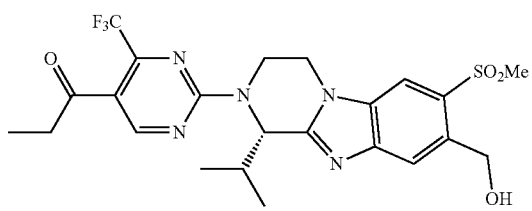

The title compounds were prepared following procedure analogous to those described in Example 6 by using 1-(2-chloro-4-(trifluoromethyl)pyrimidin-5-yl)propan-1-one in stead of 1-(2-chloro-4-(trifluoromethyl)pyrimidin-5-yl)ethanone.

Isomer 1: (R)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-1-one. Analytical chiral HPLC: t$_R$=6.87 min in 15 min chromatography (Method: OJ-H_3_5_40_2.5 ML). LC-MS m/z 526.1 [M+H]$^+$. $^1$H NMR (CD$_3$OD 400 MHz): δ 8.94 (s, 1H), 8.24 (s, 1H), 7.96 (s, 1H), 6.17-6.02 (m, 1H), 5.43-5.32 (m, 1H), 5.11 (s, 2H), 4.54 (dd, J=4.0 and 12.0 Hz, 1H), 4.24 (dt, J=4.8 and 12.0 Hz, 1H), 3.98-3.90 (m, 1H), 3.27 (s, 3H), 2.93 (q, J=6.8 Hz, 2H), 2.61-2.55 (m, 1H), 1.29 (d, J=6.8 Hz, 3H), 1.15 (t, J=7.2 Hz, 3H), 1.07 (d, J=6.8 Hz, 3H).

Isomer 2: (S)-1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-1-one. Analytical chiral HPLC: t$_R$=8.40 min in 15 min chromatography (Method: OJ-H_3_5_40_2.5 ML). LC-MS m/z 526.1 [M+H]$^+$. $^1$H NMR (CD$_3$OD 400 MHz): δ 8.93 (s, 1H), 8.21 (s, 1H), 7.93 (s, 1H), 6.15-6.01 (m, 1H), 5.47-5.31 (m, 1H), 5.09 (s, 2H), 4.53 (dd, J=4.0 and 12.0 Hz, 1H), 4.24 (dt, J=4.8 and 12.0 Hz, 1H), 3.97-3.90 (m, 1H), 3.24 (s, 3H), 2.92 (q, J=6.8 Hz, 2H), 2.60-2.55 (m, 1H), 1.28 (d, J=6.8 Hz, 3H), 1.14 (t, J=7.2 Hz, 3H), 1.07 (d, J=6.8 Hz, 3H).

Example 10

1-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)propan-1-ol (4 isomers)

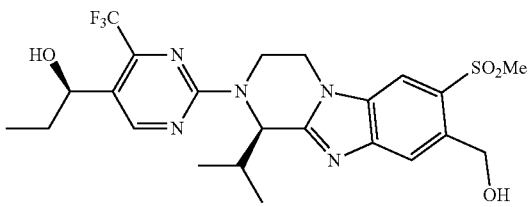

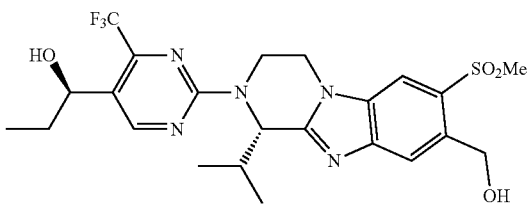

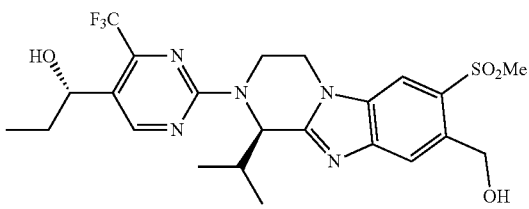

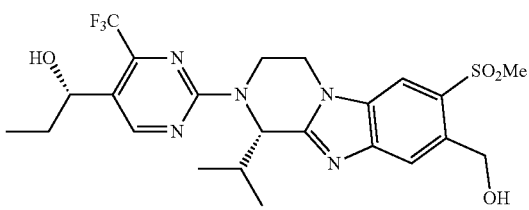

The title compounds were prepared following procedure analogous to those described in Example 8 by using 1-(2-chloro-4-(trifluoromethyl)pyrimidin-5-yl)propan-1-one instead of 1-(2-chloro-4-(trifluoromethyl)pyrimidin-5-yl)ethanone.

Isomer 1: a white solid. Analytical chiral HPLC: $t_R$=6.529 min in 15 min chromatography (Method: OD-H_3_5_40_2.35 ML). LC-MS m/z 528.2 [M+H]$^+$. $^1$H NMR (CDCl$_3$ 400 MHz): δ 8.81 (s, 1H), 8.13 (s, 1H), 7.88 (s, 1H), 6.10 (d, J=7.6 Hz, 1H), 5.38-5.34 (m, 1H), 5.05-5.02 (m, 2H), 4.98-4.90 (m, 1H), 4.34-4.30 (m, 1H), 4.21-4.17 (m, 1H), 3.82-3.74 (m, 1H), 3.23 (s, 3H), 3.06 (t, J=7.2 Hz, 1H), 2.52-2.50 (m, 1H), 1.94-1.93 (m, 1H), 1.80-1.76 (m, 2H), 1.31 (d, J=6.8 Hz, 3H), 1.08 (d, J=6.8 Hz, 3H), 0.99 (t, J=7.2 Hz, 3H).

Isomer 2: a white solid. Analytical chiral HPLC: $t_R$=7.502 min in 15 min chromatography (Method: OD-H_3_5_40_2.35 ML). LC-MS m/z 528.2 [M+H]$^+$. $^1$H NMR (CDCl$_3$ 400 MHz): δ 8.82 (s, 1H), 8.13 (s, 1H), 7.88 (s, 1H), 6.10 (d, J=7.6 Hz, 1H), 5.39-5.34 (m, 1H), 5.05-5.02 (m, 2H), 4.98-4.90 (m, 1H), 4.34-4.30 (m, 1H), 4.21-4.16 (m, 1H), 3.82-3.74 (m, 1H), 3.22 (s, 3H), 3.10 (t, J=6.8 Hz, 1H), 2.52-2.49 (m, 1H), 2.01-2.00 (m, 1H), 1.80-1.75 (m, 2H), 1.30 (d, J=6.8 Hz, 3H), 1.08 (d, J=6.8 Hz, 3H), 0.99 (t, J=7.2 Hz, 3H).

Isomer 3: a white solid. Analytical chiral HPLC: $t_R$=5.173 min in 15 min chromatography (Method: OJ-H_3_5_40_2.35 ML). LC-MS m/z 528.2 [M+H]$^+$. $^1$H NMR (CDCl$_3$ 400 MHz): δ 8.81 (s, 1H), 8.13 (s, 1H), 7.88 (s, 1H), 6.10 (d, J=7.6 Hz, 1H), 5.38-5.34 (m, 1H), 5.05-5.02 (m, 2H), 4.98-4.90 (m, 1H), 4.34-4.30 (m, 1H), 4.21-4.17 (m, 1H), 3.82-3.76 (m, 1H), 3.23 (s, 3H), 3.07 (t, J=6.8 Hz, 1H), 2.52-2.50 (m, 1H), 1.94-1.93 (m, 1H), 1.80-1.75 (m, 2H), 1.31 (d, J=6.8 Hz, 3H), 1.08 (d, J=6.8 Hz, 3H), 0.99 (t, J=7.2 Hz, 3H).

Isomer 4: a white solid. Analytical chiral HPLC: $t_R$=5.817 min in 15 min chromatography (Method: OJ-H_3_5_40_2.35 ML). LC-MS m/z 528.2 [M+H]$^+$. $^1$H NMR (CDCl$_3$ 400 MHz): δ 8.81 (s, 1H), 8.13 (s, 1H), 7.88 (s, 1H), 6.10 (d, J=8.0 Hz, 1H), 5.38-5.35 (m, 1H), 5.05-5.04 (m, 2H), 4.98-4.90 (m, 1H), 4.34-4.30 (m, 1H), 4.21-4.18 (m, 1H), 3.81-3.76 (m, 1H), 3.23 (s, 3H), 3.06 (t, J=6.4 Hz, 1H), 2.52-2.50 (m, 1H), 1.94-1.93 (m, 1H), 1.81-1.75 (m, 2H), 1.31 (d, J=6.8 Hz, 3H), 1.08 (d, J=6.8 Hz, 3H), 0.99 (t, J=7.2 Hz, 3H).

Example 11

(R)-1-(2-((R)-8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)butan-1-ol and (S)-1-(2-((R)-8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)butan-1-ol

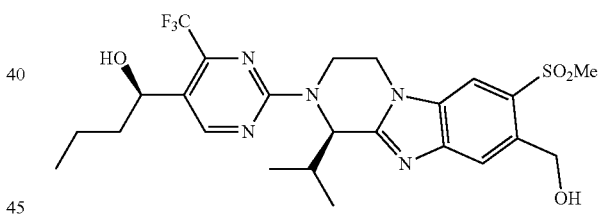

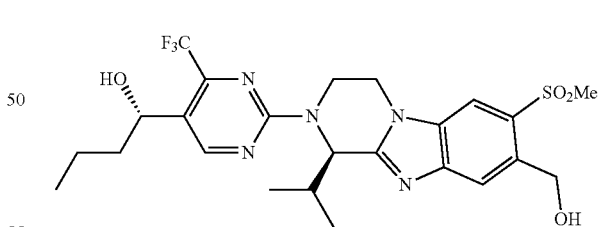

The title compounds were prepared following procedure analogous to those described in Example 8 by using 1-(2-chloro-4-(trifluoromethyl)pyrimidin-5-yl)butan-1-one instead of 1-(2-chloro-4-(trifluoromethyl)pyrimidin-5-yl)ethanone.

Isomer 1: Analytical chiral HPLC: $t_R$=8.450 min in 15 min chromatography (Method: OD-H_3_5_40_2.35 ML). LC-MS MS (ESI) m/z 542.1 [M+H]$^+$. $^1$H NMR (CD$_3$OD 400 MHz): δ 8.87 (s, 1H), 8.26 (s, 1H), 7.98 (s, 1H), 6.06 (d, J=8.0 Hz, 1H), 5.36-5.33 (m, 1H), 5.14 (s, 2H), 4.54-4.51 (m, 1H), 4.27-4.20 (m, 1H), 3.94-3.86 (m, 1H), 3.29 (s, 3H), 2.60-2.52

(m, 1H), 1.78-1.71 (m, 1H), 1.60-1.49 (m, 2H), 1.43-1.26 (m, 5H), 1.08 (d, J=6.8 Hz, 3H), 0.96 (t, J=6.8 Hz, 3H).

Isomer 2: Analytical chiral HPLC: $t_R$=10.264 min in 15 min chromatography (Method: OD-H_3_5_40_2.35 ML). LC-MS MS (ESI) m/z 542.1 [M+H]$^+$. $^1$H NMR (CD$_3$OD 400 MHz): δ 8.87 (s, 1H), 8.26 (s, 1H), 7.98 (s, 1H), 6.06 (d, J=8.0 Hz, 1H), 5.36-5.33 (m, 1H), 5.14 (s, 2H), 4.54-4.51 (m, 1H), 4.27-4.20 (m, 1H), 3.94-3.86 (m, 1H), 3.29 (s, 3H), 2.60-2.52 (m, 1H), 1.78-1.71 (m, 1H), 1.60-1.49 (m, 2H), 1.43-1.26 (m, 5H), 1.08 (d, J=6.8 Hz, 3H), 0.96 (t, J=6.8 Hz, 3H).

Example 12

(R)-ethyl 2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate

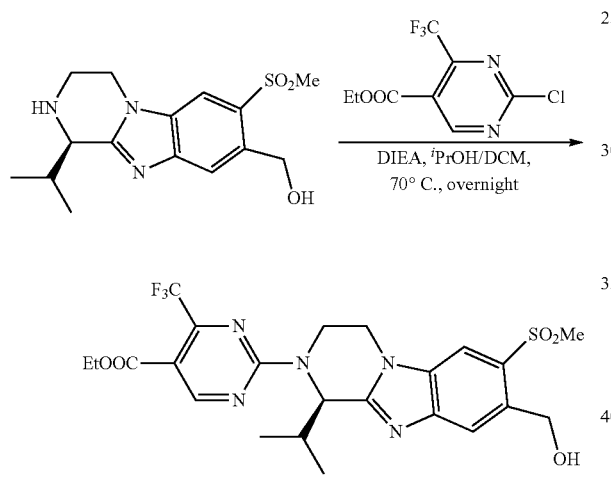

To a solution of (R)-(1-isopropyl-7-(methylsulfonyl)-1,2,3,4-tetrahydrobenzo[4,5]imidazo[1,2-a]pyrazin-8-yl)methanol (30 mg, 0.093 mmol) in CH$_2$Cl$_2$ (0.5 mL) and $^i$PrOH (0.5 mL) was added ethyl 2-chloro-4-(trifluoromethyl)pyrimidine-5-carboxylate (36 mg, 0.14 mmol) and DIEA (36 mg, 0.28 mmol). The mixture was stirred at 70° C. overnight. The mixture was concentrated under reduced pressure. Water (5 mL) was added to the mixture and the aqueous layer was extracted with EtOAc (3×10 mL). The combined organic layers were washed with water and brine, dried over anhydrous Na$_2$SO$_4$, filtered and concentrated under vacuum. The residue was purified by preparative TLC to afford (R)-ethyl 2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate (42.0 mg, 83.7% yield) as a white solid. Analytical chiral HPLC: $t_R$=9.927 min in 15 min chromatography, 96.74% ee (Method: OD-H_5_5_40_2.35 ML). LC-MS MS (ESI) m/z 542.1 [M+H]$^+$. $^1$H NMR (CD$_3$OD 300 MHz): δ 8.96 (s, 1H), 8.12 (s, 1H), 7.85 (s, 1H), 6.12-6.00 (m, 1H), 5.45-5.29 (m, 1H), 5.01 (s, 2H), 4.51-4.47 (m, 1H), 4.33-4.18 (m, 3H), 3.91 (t, J=10.8 Hz, 1H), 3.18 (s, 3H), 2.63-2.47 (m, 1H), 1.35-1.26 (m, 6H), 1.05 (d, J=6.6 Hz, 3H).

Example 13

(R)-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)methanol and (S)-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)methanol

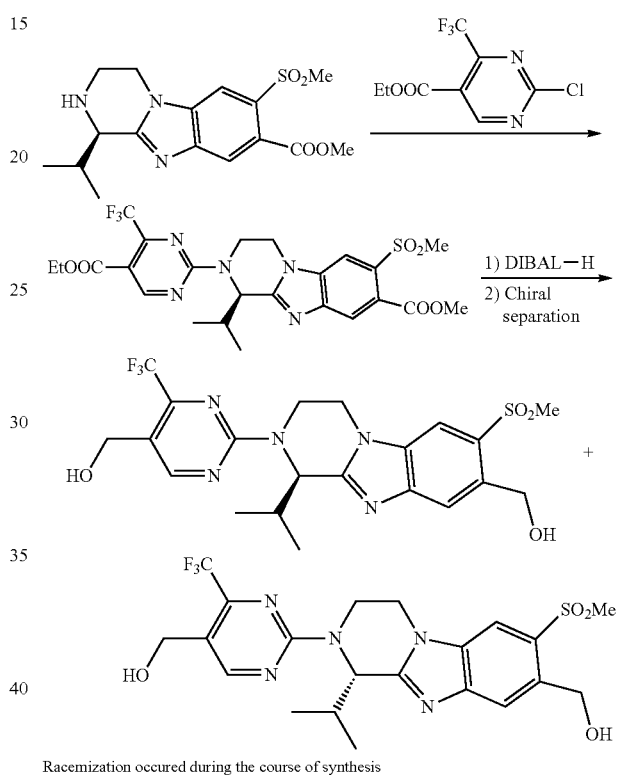

Racemization occured during the course of synthesis

To a solution of (R)-methyl 1-isopropyl-7-(methylsulfonyl)-1,2,3,4-tetrahydrobenzo[4,5]imidazo[1,2-a]pyrazine-8-carboxylate (80 mg, 0.228 mmol) in $^i$PrOH (2 mL) and DCM (1 mL) was added ethyl 2-chloro-4-(trifluoromethyl)pyrimidine-5-carboxylate (174 mg, 0.684 mmol) and DIEA (177 mg, 1.37 mmol). The mixture was stirred at 60° C. overnight. Water (5 mL) was added to the mixture and the aqueous layer was extracted with EtOAc (2×10 mL). The combined organic layers were washed with water (2×10 mL) and brine, dried over anhydrous Na$_2$SO$_4$, filtered and concentrated under vacuum. The residue was purified by preparative TLC to afford (R)-methyl 2-(5-(ethoxycarbonyl)-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (75 mg, 57.8% yield) as a yellow solid.

To a solution of (R)-methyl 2-(5-(ethoxycarbonyl)-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (75 mg, 0.132 mmol) in DCM (3 mL) was added DIBAL-H (1M in toluene, 0.50 mL, 0.528 mmol) at −78° C. The mixture was stirred at −78° C. for 3 h. Sat. NH$_4$Cl solution (10 mL) was added at −78° C. and the mixture was filtered. The aqueous layer was extracted with DCM (3×20 mL). The combined organic layers were washed with brine, dried over anhydrous Na₂SO₄, filtered and concentrated under reduced pressure. The residue was purified by preparative TLC to give the racemic mixture (56.0 mg, 85.1% yield) as a white solid. The racemic mixture was separated by SFC separation to give (R)-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl) methanol (38.10 mg, isomer 1) and (S)-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)methanol (11.90 mg, isomer 2) as white solids.

Isomer 1: (R)-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)methanol. Analytical chiral HPLC: $t_R$=10.281 min in 15 min chromatography (Method: AD-H_5_5_40_2.35 ML). LC-MS MS (ESI) m/z 500.1 [M+H]⁺. ¹H NMR (CD₃OD 400 MHz): δ 8.73 (s, 1H), 8.20 (s, 1H), 7.93 (s, 1H), 6.04 (d, J=8.0 Hz, 1H), 5.33 (dd, J=4.4 and 14.0 Hz, 1H), 5.09 (s, 2H), 4.63 (s, 2H), 4.50-4.46 (m, 1H), 4.28-4.06 (m, 1H), 3.91-3.83 (m, 1H), 3.24 (s, 3H), 2.59-2.47 (m, 1H), 1.26 (d, J=6.8 Hz, 3H), 1.04 (d, J=6.8 Hz, 3H).

Isomer 2: (S)-(2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidin-5-yl)methanol. Analytical chiral HPLC: $t_R$=8.340 min in 15 min chromatography (Method: AD-H_5_5_40_2.35 ML). LC-MS MS (ESI) m/z 500.1 [M+H]⁺. ¹H NMR (CD₃OD 400 MHz): δ 8.73 (s, 1H), 8.22 (s, 1H), 7.94 (s, 1H), 6.04 (d, J=8.4 Hz, 1H), 5.33 (dd, J=4.8 and 14.4 Hz, 1H), 5.09 (s, 2H), 4.63 (s, 2H), 4.52-4.45 (m, 1H), 4.24-4.17 (m, 1H), 3.91-3.84 (m, 1H), 3.25 (s, 3H), 2.68-2.46 (m, 1H), 1.26 (d, J=6.8 Hz, 3H), 1.05 (d, J=6.8 Hz, 3H).

Example 14

(R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid and (S)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid

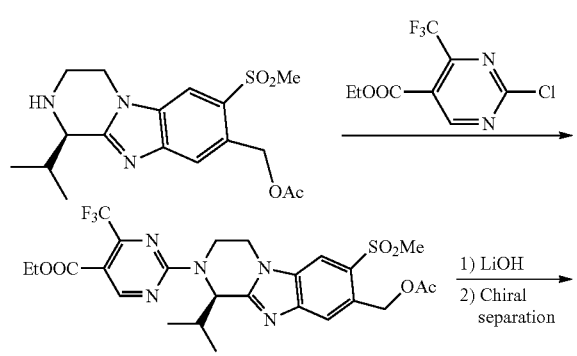

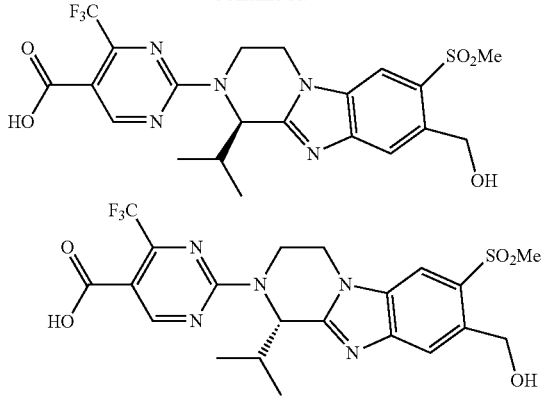

Racemization occured during the course of synthesis

The mixture of (R)-(1-isopropyl-7-(methylsulfonyl)-1,2,3,4-tetrahydrobenzo[4,5]imidazo[1,2-a]pyrazin-8-yl)methyl acetate (284 mg, 0.8 mmol), ethyl 2-chloro-4-(trifluoromethyl)pyrimidine-5-carboxylate (296 mg, 1.2 mmol, 1.5 eq.) and DIEA (310 mg, 2.4 mmol, 3 eq.) in CH₂Cl₂/i-PrOH (3 mL/3 mL) was stirred at 80° C. for 16 h. TLC showed compound was consumed completely PE:EtOAc=1:1. The solvents were removed under vacuum and the residue was dissolved in EtOAc (10 mL). Water (10 mL) was added to the mixture. The mixture was extracted with EtOAc (10 mL×3). The organic layers were dried over anhydrous Na₂SO₄, filtered and concentrated under vacuum. The residue was purified by column chromatography on silica gel eluting with PE:EtOAc 5:1 to give (R)-ethyl 2-(8-(acetoxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate (0.41 g, 87% yield) as a pale yellow solid.

(R)-ethyl 2-(8-(acetoxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate (0.1 g, 0.17 mmol) in MeOH/H₂O (5 mL/1 mL) was added LiOH H₂O (86 mg, 2 mmol). The mixture was stirred at rt for 16 h. The excess methanol was removed by vacuum at 40° C. Water (5 ml) was added and the mixture was neutralized by 1N HCl at 0° C. slowly to pH=6. The aqueous layer was extracted with CH₂Cl₂ (4×10 mL). The combined organic layers were dried over anhydrous Na₂SO₄, filtered and concentrated under vacuum to give crude product. The crude product was purified by SFC to afford (R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid (34.50 mg, 40% yield, isomer 1) as a white solid and (S)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid (6.40 mg, 7% yield, isomer 2) as white solid.

Isomer 1: (R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid. Analytical chiral HPLC: $t_R$=6.474 min in 15 min chromatography (Method: OJ-H_3_5_40_2.35 ML). LC-MS MS (ESI) m/z 514.0 [M+H]⁺. ¹H NMR (CD₃OD 400 MHz): δ 9.05 (s, 1H), 8.20 (s, 1H), 7.91 (s, 1H), 6.20-6.15 (m, 1H), 5.50-5.35 (m, 1H), 5.08 (s, 2H), 4.60-4.50 (m, 1H), 4.35-4.20 (m, 1H), 4.03-3.89 (m, 1H), 3.25 (s, 3H), 2.70-2.53 (m, 1H), 1.30 (d, J=6.8 Hz, 3H), 1.08 (d, J=6.8 Hz, 3H).

Isomer 2: (S)-2-(8-(hydroxymethyl)-1-isopropyl-7-(methylsulfonyl)-3,4-dihydrobenzo[4,5]imidazo[1,2-a]pyrazin-2

(1H)-yl)-4-(trifluoromethyl)pyrimidine-5-carboxylic acid. Analytical chiral HPLC: $t_R$=8.468 min in 15 min chromatography (Method: OJ-H_3_5_40_2.35 ML). LC-MS MS (ESI) m/z 514.0 [M+H]$^+$. $^1$H NMR (CD$_3$OD 400 MHz): δ 9.02 (s, 1H), 8.25 (s, 1H), 8.00 (s, 1H), 6.20-6.15 (m, 1H), 5.50-5.35 (m, 1H), 5.12 (s, 2H), 4.60-4.50 (m, 1H), 4.35-4.20 (m, 1H), 4.03-3.89 (m, 1H), 3.28 (s, 3H), 2.70-2.50 (m, 1H), 1.30 (d, J=6.8 Hz, 3H), 1.08 (d, J=6.8 Hz, 3H).

Example 15

(R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide and (S)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide

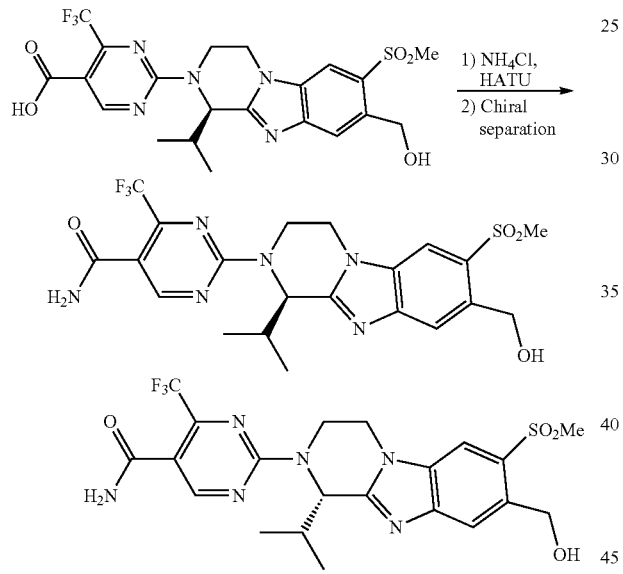

Starting material partially racemized

To a solution of (R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylic acid (100 mg, 0.19 mmol, partially racemized) in DMF (2 mL) was added HATU (97 mg, 0.25 mmol) and Et$_3$N (52 mg, 0.51 mmol). The mixture was stirred at rt for 1 h. NH$_4$Cl (19 mg, 0.34 mmol) was added in one portion. The mixture was stirred at rt for 16 h. Water (10 mL) was added and the aqueous layer was extracted with EtOAc (4×10 mL). The combined organic layers were washed with water (3×10 mL) and brine, dried over anhydrous Na$_2$SO$_4$, filtered and concentrated under vacuum. The residue was purified by preparative TLC and SFC separation to afford (R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide (55.2 mg, 56.7% yield, isomer 1) as a white solid and (S)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide (10.5 mg, 10.8% yield, isomer 2) as white solid.

Isomer 1: (R)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide. Analytical chiral HPLC: $t_R$=6.084 min in 15 min chromatography (Method: OJ-H_3_5_40_2.35 ML). LC-MS MS (ESI) m/z 513.0 [M+H]$^+$. $^1$H NMR (CD$_3$OD 400 MHz): δ 8.71 (s, 1H), 8.25 (s, 1H), 7.97 (s, 1H), 6.13-6.01 (m, 1H), 5.45-5.30 (m, 1H), 5.13 (s, 2H), 4.59-4.50 (m, 1H), 4.31-4.18 (m, 1H), 4.00-3.86 (m, 1H), 3.27 (s, 3H), 2.65-2.50 (m, 1H), 1.28 (d, J=6.8 Hz, 3H), 1.06 (d, J=6.8 Hz, 3H).

Isomer 2: (S)-2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxamide.

Analytical chiral HPLC: $t_R$=7.218 min in 15 min chromatography (Method: OJ-H_3_5_40_2.35 ML). LC-MS MS (ESI) m/z 513.1 [M+H]$^+$. $^1$H NMR (CD$_3$OD 400 MHz): δ 8.71 (s, 1H), 8.25 (s, 1H), 7.97 (s, 1H), 6.13-6.02 (m, 1H), 5.45-5.30 (m, 1H), 5.12 (s, 2H), 4.60-4.50 (m, 1H), 4.32-4.18 (m, 1H), 4.00-3.86 (m, 1H), 3.28 (s, 3H), 2.65-2.50 (m, 1H), 1.28 (d, J=6.8 Hz, 3H), 1.06 (d, J=6.8 Hz, 3H).

Example 16

(R)-2-(8-(hydroxymethyl)-1-isopropyl-7-(methylsulfonyl)-3,4-dihydrobenzo[4,5]imidazo[1,2-a]pyrazin-2(1H)-yl)-N-methyl-4-(trifluoromethyl)pyrimidine-5-carboxamide and (S)-2-(8-(hydroxymethyl)-1-isopropyl-7-(methylsulfonyl)-3,4-dihydrobenzo[4,5]imidazo[1,2-a]pyrazin-2(1H)-yl)-N-methyl-4-(trifluoromethyl)pyrimidine-5-carboxamide

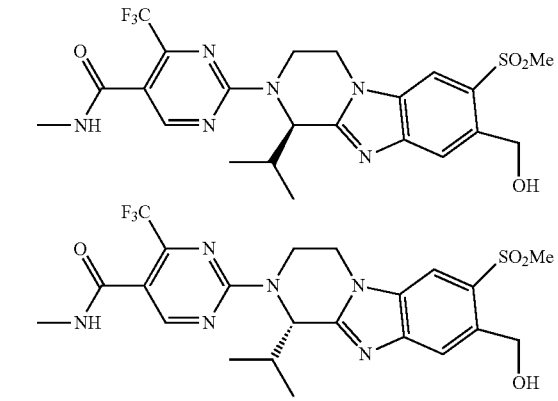

The title compounds were prepared by a procedure analogous to those described in Example 15 by using methylamine hydrochloric acid salt instead of ammonium chloride as a reagent.

Isomer 1: (R)-2-(8-(hydroxymethyl)-1-isopropyl-7-(methylsulfonyl)-3,4-dihydrobenzo[4,5]imidazo[1,2-a]pyrazin-2(1H)-yl)-N-methyl-4-(trifluoromethyl)pyrimidine-5-carboxamide. Analytical chiral HPLC: $t_R$=6.355 min in 15 min chromatography (Method: AS-H_3_5_40_2.35 ML). LC-MS MS (ESI) m/z 548.9 [M+Na]. $^1$H NMR (CD$_3$OD 400 MHz): δ 8.68 (s, 1H), 8.27 (s, 1H), 7.99 (s, 1H), 6.14-6.00 (m, 1H), 5.45-5.30 (m, 1H), 5.13 (s, 2H), 4.60-4.50 (m, 1H), 4.30-4.18 (m, 1H), 4.00-3.86 (m, 1H), 3.30 (s, 3H), 2.90 (s, 3H), 2.66-2.51 (m, 1H), 1.31 (d, J=6.8 Hz, 3H), 1.15 (d, J=6.8 Hz, 3H).

Isomer 2: (S)-2-(8-(hydroxymethyl)-1-isopropyl-7-(methylsulfonyl)-3,4-dihydrobenzo[4,5]imidazo[1,2-a]pyrazin-2(1H)-yl)-N-methyl-4-(trifluoromethyl)pyrimidine-5-carboxamide. Analytical chiral HPLC: $t_R$=6.486 min in 15 min chromatography (Method: AS-H_3_5_40_2.35 ML). LC-MS MS (ESI) m/z 549.0 [M+Na]. $^1$H NMR (CD$_3$OD 400 MHz): δ 8.68 (s, 1H), 8.29 (s, 1H), 8.00 (s, 1H), 6.14-6.00 (m, 1H), 5.45-5.30 (m, 1H), 5.13 (s, 2H), 4.62-4.52 (m, 1H), 4.32-4.20 (m, 1H), 4.02-3.87 (m, 1H), 3.30 (s, 3H), 2.91 (s, 3H), 2.67-2.51 (m, 1H), 1.31 (d, J=6.8 Hz, 3H), 1.11 (d, J=6.8 Hz, 3H).

Example 17

(R)-2-(8-(hydroxymethyl)-1-isopropyl-7-(methylsulfonyl)-3,4-dihydrobenzo[4,5]imidazo[1,2-a]pyrazin-2(1H)-yl)-N,N-dimethyl-4-(trifluoromethyl)pyrimidine-5-carboxamide and (S)-2-(8-(hydroxymethyl)-1-isopropyl-7-(methylsulfonyl)-3,4-dihydrobenzo[4,5]imidazo[1,2-a]pyrazin-2(1H)-yl)-N,N-dimethyl-4-(trifluoromethyl)pyrimidine-5-carboxamide

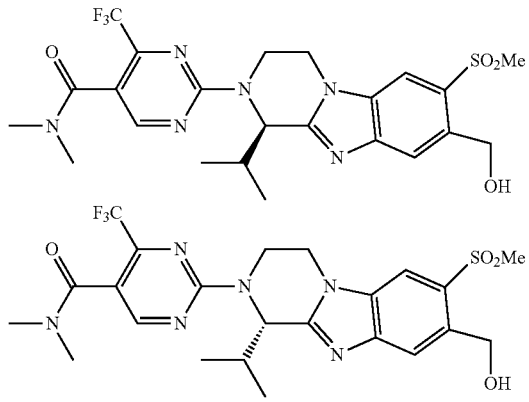

The title compounds were prepared by a procedure analogous to those described in Example 15 by using dimethylamine hydrochloric acid salt instead of ammonium chloride as a reagent.

Isomer 1: (R)-2-(8-(hydroxymethyl)-1-isopropyl-7-(methylsulfonyl)-3,4-dihydrobenzo[4,5]imidazo[1,2-a]pyrazin-2(1H)-yl)-N,N-dimethyl-4-(trifluoromethyl)pyrimidine-5-carboxamide. Analytical chiral HPLC: $t_R$=3.649 min in 8 min chromatography (Method: AS-H_S_3_5_40_3 ML). LC-MS MS (ESI) m/z 563.1 [M+Na]$^+$. $^1$H NMR (CD$_3$OD 400 MHz): δ 8.62 (s, 1H), 8.23 (d, J=6.4 Hz, 1H), 7.95 (d, J=5.2 Hz, 1H), 6.09-5.98 (m, 1H), 5.50-5.26 (m, 1H), 5.10 (d, J=4.4 Hz, 2H), 4.59-4.50 (m, 1H), 4.32-4.20 (m, 1H), 4.03-3.87 (m, 1H), 3.30-3.25 (m, 3H), 3.11 (s, 3H), 2.95 (s, 3H), 2.67-2.51 (m, 1H), 1.31 (d, J=6.8 Hz, 3H), 1.09 (d, J=6.8 Hz, 3H).

Isomer 2: (S)-2-(8-(hydroxymethyl)-1-isopropyl-7-(methylsulfonyl)-3,4-dihydrobenzo[4,5]imidazo[1,2-a]pyrazin-2(1H)-yl)-N,N-dimethyl-4-(trifluoromethyl)pyrimidine-5-carboxamide. Analytical chiral HPLC: $t_R$=4.502 min in 8 min chromatography (Method: AS-H_S_3_5_40_3 ML). LC-MS MS (ESI) m/z 563.1 [M+Na]$^+$.

$^1$H NMR (CD$_3$OD 400 MHz): δ 8.62 (s, 1H), 8.27 (s, 1H), 7.98 (s, 1H), 6.09-5.98 (m, 1H), 5.49-5.28 (m, 1H), 5.13 (s, 2H), 4.59-4.50 (m, 1H), 4.33-4.20 (m, 1H), 4.05-3.90 (m, 1H), 3.30 (s, 3H), 3.12 (s, 3H), 2.95 (s, 3H), 2.68-2.52 (m, 1H), 1.32 (d, J=6.8 Hz, 3H), 1.10 (d, J=6.8 Hz, 3H).

Example 18

(R)-(1-isopropyl-2-(4-methoxy-5-(trifluoromethyl)pyrimidin-2-yl)-7-(methylsulfonyl)-1,2,3,4-tetrahydrobenzo[4,5]imidazo[1,2-a]pyrazin-8-yl)methanol

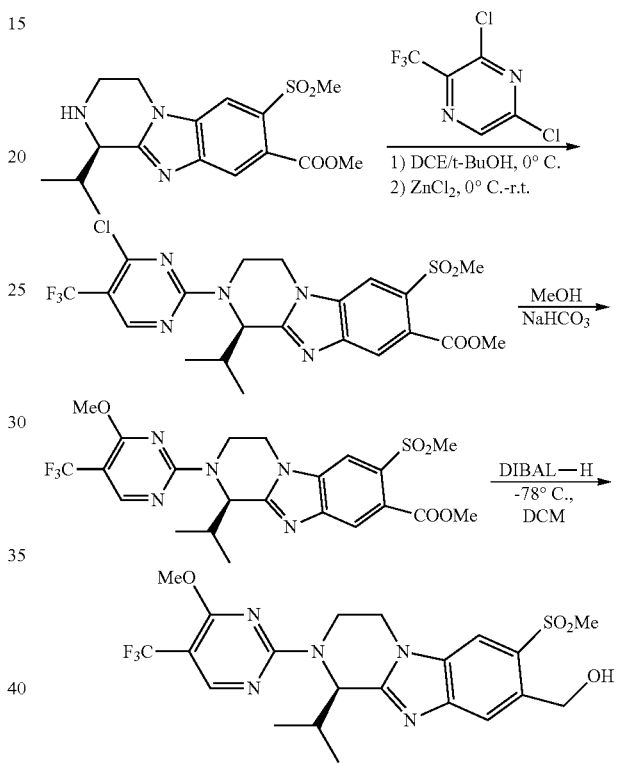

To a solution of 2,4-dichloro-5-(trifluoromethyl)pyrimidine (20.0 mg, 0.092 mmol) in DCE (1 mL) and t-BuOH (1 mL) was added ZnCl$_2$ (1M in diethyl ether, 0.2 mL, 0.2 mmol) at 0° C. The mixture was stirred at 0° C. for 1 h. Then a solution of (R)-methyl 1-isopropyl-7-(methylsulfonyl)-1,2,3,4-tetrahydrobenzo[4,5]imidazo[1,2-a]pyrazine-8-carboxylate (31 mg, 0.09 mmol) in DCE (1 mL) and t-BuOH (1 mL) was added to the reaction mixture via syringe over 1 min at 0° C. After addition, the resulting mixture was stirred at rt overnight. The reaction mixture was concentrated under vacuum. Water (5 mL) and EtOAc (5 mL) were added to the mixture. The aqueous phase was extracted with EtOAc (3×10 mL). The combined organic layers were washed with brine, dried over anhydrous Na$_2$SO$_4$, filtered and concentrated under vacuum. The residue was purified by preparative TLC to afford (R)-methyl 2-(4-chloro-5-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (20 mg, 42.6% yield) as a white solid.

To a solution of (R)-methyl 2-(4-chloro-5-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (15 mg, 0.028 mmol) in methanol (4 mL) was added NaHCO$_3$ (25 mg, 0.29 mmol). The mixture was stirred at 60° C. for 20 h. The mixture was concentrated under vacuum. Water (5 mL) and EtOAc (5 mL) were added to the mixture. The aqueous phase was extracted with EtOAc (3×10 mL). The combined organic layers were washed with brine, dried over anhydrous Na$_2$SO$_4$, filtered and concentrated under vacuum. The residue was purified by preparative TLC to afford (R)-methyl 1-isopropyl-2-(4-methoxy-5-(trifluoromethyl)pyrimidin-2-yl)-7-(methylsulfonyl)-1,2,3,4-tetrahydrobenzo[4,5]imidazo[1,2-a]pyrazine-8-carboxylate (13.0 mg, 87.2% yield) as a white solid.

To a solution of (R)-methyl 1-isopropyl-2-(4-methoxy-5-(trifluoromethyl)pyrimidin-2-yl)-7-(methylsulfonyl)-1,2,3,4-tetrahydrobenzo[4,5]imidazo[1,2-a]pyrazine-8-carboxylate (15 mg, 0.028 mmol) in CH$_2$Cl$_2$ (2 mL) was added DIBAL H (1M in toluene, 0.1 mL, 0.1 mmol) at −78° C. The mixture was stirred at −78° C. for 2 h and warmed to rt for 6 h. Sat. NH$_4$Cl solution (1 mL) was added and the mixture was filtered. The filtrate was concentrated under vacuum. Water (5 mL) and EtOAc (5 mL) were added to the mixture. The aqueous layer was extracted with EtOAc (3×5 mL). The combined organic layers were washed with brine, dried over anhydrous Na$_2$SO$_4$, filtered and concentrated under vacuum. The residue was purified by preparative TLC to afford (R)-(1-isopropyl-2-(4-methoxy-5-(trifluoromethyl)pyrimidin-2-yl)-7-(methylsulfonyl)-1,2,3,4-tetrahydrobenzo[4,5]imidazo[1,2-a]pyrazin-8-yl)methanol (3.50 mg, 24.6% yield) as a white solid. Analytical chiral HPLC: t$_R$=6.598 min in 15 min chromatography, 94.60% ee (Method: OD-H_3_5_40_2.35 ML). LC-MS MS (ESI) m/z 500.1 [M+H]$^+$. $^1$H NMR (CDCl$_3$ 300 MHz): δ 8.31 (s, 1H), 8.12 (s, 1H), 7.86 (s, 1H), 6.02-5.98 (m, 1H), 5.43-5.38 (m, 1H), 5.04-4.98 (m, 2H), 4.32-4.28 (m, 1H), 4.16 (dt, J=5.1 and 12.0 Hz, 1H), 4.01 (s, 3H), 3.77-3.68 (m, 1H), 3.21 (s, 3H), 3.11-3.06 (m, 1H), 2.50-2.47 (m, 1H), 1.30 (d, J=6.6 Hz, 3H), 1.07 (d, J=6.6 Hz, 3H).

Example 19

(R)-(2-(8-(hydroxymethyl)-1-isopropyl-7-(methylsulfonyl)-3,4-dihydrobenzo[4,5]imidazo[1,2-a]pyrazin-2(1H)-yl)-4-methylpyrimidin-5-yl)methanol

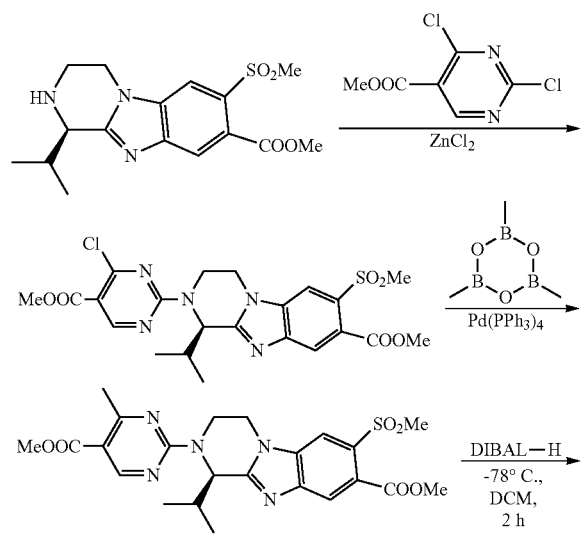

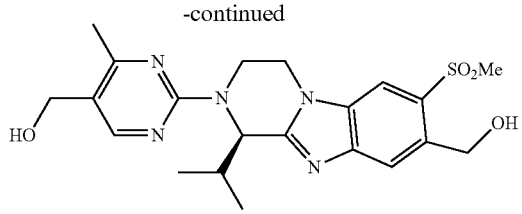

A solution of methyl 2,4-dichloropyrimidine-5-carboxylate (27 mg, 0.13 mmol) in dichloroethane/t-butanol (1:1, 2 mL) was cooled to 0° C. ZnCl$_2$ solution (1.0 M in ether, 0.29 mL, 0.29 mmol, 2.2 eq.) was added. After stirring for 1 h, a solution of (R)-methyl 1-isopropyl-7-(methylsulfonyl)-1,2,3,4-tetrahydrobenzo[4,5]imidazo[1,2-a]pyrazine-8-carboxylate (30 mg, 0.09 mmol) in dichloroethane/t-butanol (1:1, 2 mL) was added slowly at 0° C. The mixture was stirred at rt overnight. Water (10 mL) was added and the mixture was extracted with EtOAc (10 mL×3). The combined organic layers were dried over anhydrous Na$_2$SO$_4$, filtered and concentrated under vacuum. The residue was purified by preparative TLC to afford (R)-methyl 2-(4-chloro-5-(methoxycarbonyl)pyrimidin-2-yl)-1-isopropyl-7-(methylsulfonyl)-1,2,3,4-tetrahydrobenzo[4,5]imidazo[1,2-a]pyrazine-8-carboxylate (34 mg, 77.3% yield) as a solid.

To a solution of (R)-methyl 2-(4-chloro-5-(methoxycarbonyl)pyrimidin-2-yl)-1-isopropyl-7-(methylsulfonyl)-1,2,3,4-tetrahydrobenzo[4,5]imidazo[1,2-a]pyrazine-8-carboxylate (20 mg, 0.04 mmol) and 2,4,6-trimethyl-1,3,5,2,4,6-trioxatriborinane (50 mg, 0.4 mmol) in 5 mL of dioxane was added K$_2$CO$_3$ (54 mg, 0.4 mmol) followed by Pd(PPh$_3$)$_4$ (5 mg, 0.004 mmol) under N$_2$ with stirring. The mixture was refluxed for 2 h until the material was disappeared. The reaction mixture was cooled to rt. The dioxane was removed under vacuum. Water (10 mL) was added and the mixture was extracted with EtOAc (10 mL×3). The organic layers were dried over anhydrous Na$_2$SO$_4$, filtered and concentrated under vacuum. The residue was purified by preparative TLC to afford (R)-methyl 1-isopropyl-2-(5-(methoxycarbonyl)-4-methylpyrimidin-2-yl)-7-(methylsulfonyl)-1,2,3,4-tetrahydrobenzo[4,5]imidazo[1,2-a]pyrazine-8-carboxylate (15 mg, 75% yield) as a colorless oil. LC-MS MS (ESI) m/z 502.1 [M+H]$^+$.

To a solution of (R)-methyl 1-isopropyl-2-(5-(methoxycarbonyl)-4-methylpyrimidin-2-yl)-7-(methylsulfonyl)-1,2,3,4-tetrahydrobenzo[4,5]imidazo[1,2-a]pyrazine-8-carboxylate (15 mg, 0.03 mmol) in toluene (2 mL) was added DIBAL H (1M in toluene, 0.3 mL, 0.3 mmol) at −78° C. The mixture was stirred at −78° C. for 2 h and then rt for 30 mins. Sat. NH$_4$Cl solution (5 mL) was added slowly at 0° C. and the mixture was filtered. The aqueous layer was extracted with EtOAc (3×10 mL). The combined organic layers were washed with brine, dried over anhydrous Na$_2$SO$_4$, filtered and concentrated under vacuum. The residue was purified by preparative TLC to afford (R)-(2-(8-(hydroxymethyl)-1-isopropyl-7-(methylsulfonyl)-3,4-dihydrobenzo[4,5]imidazo[1,2-a]pyrazin-2(1H)-yl)-4-methylpyrimidin-5-yl)methanol (1.6 mg, 12.3% yield) as a colorless oil. LC-MS MS (ESI) m/z 446.2 [M+H]$^+$. $^1$H NMR (CD$_3$OD 400 MHz): δ 8.26 (s, 1H), 8.23 (s, 1H), 7.99 (s, 1H), 6.00 (d, J=8.8 Hz, 1H), 5.17 (s, 2H), 4.90-4.79 (m, 1H), 4.67 (s, 2H), 4.45-4.44 (m, 1H), 4.25-4.18 (m, 1H), 4.15-4.04 (m, 1H), 3.31 (s, 3H), 2.58-2.49 (m, 1H), 2.45 (s, 3H), 1.25 (d, J=6.8 Hz, 3H), 1.12 (d, J=6.8 Hz, 3H).

Example 20

(R)-(4-cyclopropyl-2-(8-(hydroxymethyl)-1-isopropyl-7-(methylsulfonyl)-3,4-dihydrobenzo[4,5]imidazo[1,2-a]pyrazin-2(1H)-yl)pyrimidin-5-yl)methanol and (S)-(4-cyclopropyl-2-(8-(hydroxymethyl)-1-isopropyl-7-(methylsulfonyl)-3,4-dihydrobenzo[4,5]imidazo[1,2-a]pyrazin-2(1H)-yl)pyrimidin-5-yl)methanol

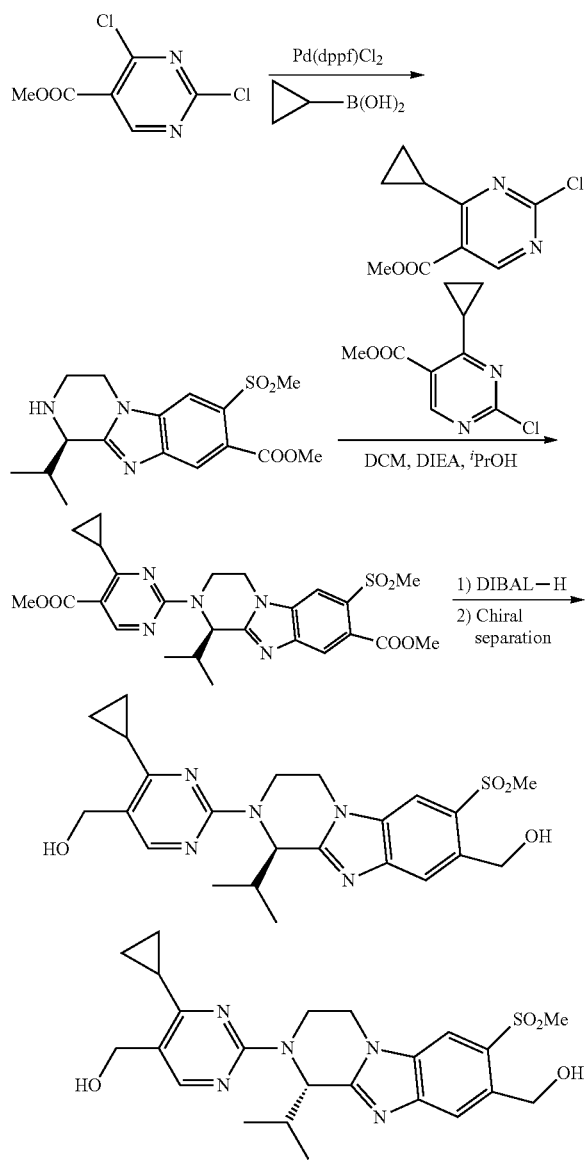

Racemization occured during the course of synthesis

To a solution of methyl 2,4-dichloropyrimidine-5-carboxylate (852 mg, 4 mmol) and cyclopropylboronic acid (344 mg, 4 mmol) in THF (10 mL) was added $K_3PO_4$ (3.1 g, 12 mmol) followed by Pd(dppf)$Cl_2$ (292 mg, 0.4 mmol) under $N_2$. The mixture was refluxed for 4 h until the material was disappeared. The reaction mixture was cooled to rt. THF was removed under vacuum. Water (20 mL) was added and the mixture was extracted with EtOAc (20 mL×3). The organic layers were dried over anhydrous $Na_2SO_4$, filtered and concentrated under vacuum. The residue was purified by preparative TLC to afford methyl 2-chloro-4-cyclopropylpyrimidine-5-carboxylate (220 mg, 26% yield) as a white solid.

The mixture of (R)-methyl 1-isopropyl-7-(methylsulfonyl)-1,2,3,4-tetrahydrobenzo[4,5]imidazo[1,2-a]pyrazine-8-carboxylate (77 mg, 0.22 mmol), methyl 2-chloro-4-cyclopropylpyrimidine-5-carboxylate (57 mg, 0.26 mmol, 1.2 eq.) and DIEA (172 mg, 1.3 mmol, 6 eq.) in $CH_2Cl_2$/i-PrOH (1 mL/1 mL) was stirred at 120° C. for 16 h. TLC showed (R)-methyl 1-isopropyl-7-(methylsulfonyl)-1,2,3,4-tetrahydrobenzo[4,5]imidazo[1,2-a]pyrazine-8-carboxylate was consumed completely (PE:EtOAc=1:1). Water (10 mL) was added and the mixture was extracted with EtOAc (10 mL×3). The organic layers were dried over anhydrous $Na_2SO_4$, filtered and concentrated under vacuum. The residue was purified by preparative TLC to afford (R)-methyl 2-(4-cyclopropyl-5-(methoxycarbonyl)pyrimidin-2-yl)-1-isopropyl-7-(methylsulfonyl)-1,2,3,4-tetrahydrobenzo[4,5]imidazo[1,2-a]pyrazine-8-carboxylate (50 mg, 43% yield) as a colorless oil.

To a solution of (R)-methyl 2-(4-cyclopropyl-5-(methoxycarbonyl)pyrimidin-2-yl)-1-isopropyl-7-(methylsulfonyl)-1,2,3,4-tetrahydrobenzo[4,5]imidazo[1,2-a]pyrazine-8-carboxylate (50 mg, 0.1 mmol) in $CH_2Cl_2$ (2 mL) was added DIBAL H (1M in toluene, 1 mL, 1 mmol) at −78° C. The mixture was stirred at −78° C. for 1 h and then rt for 1 h. Sat. $NH_4Cl$ solution (5 mL) was added slowly at 0° C. and the mixture was filtered. The aqueous layer was extracted with EtOAc (3×5 mL). The combined organic layers were washed with brine, dried over anhydrous $Na_2SO_4$, filtered and concentrated under vacuum. The residue was purified by preparative TLC and then SFC separation to afford (R)-(4-cyclopropyl-2-(8-(hydroxymethyl)-1-isopropyl-7-(methylsulfonyl)-3,4-dihydrobenzo[4,5]imidazo[1,2-a]pyrazin-2(1H)-yl)pyrimidin-5-yl)methanol (11.50 mg, 24.5% yield, isomer 1) as a colorless oil and (S)-(4-cyclopropyl-2-(8-(hydroxymethyl)-1-isopropyl-7-(methylsulfonyl)-3,4-dihydrobenzo[4,5]imidazo[1,2-a]pyrazin-2(1H)-yl)pyrimidin-5-yl)methanol (7.10 mg, 15.1% yield, isomer 2) as a colorless oil.

Isomer 1: (R)-(4-cyclopropyl-2-(8-(hydroxymethyl)-1-isopropyl-7-(methylsulfonyl)-3,4-dihydrobenzo[4,5]imidazo[1,2-a]pyrazin-2(1H)-yl)pyrimidin-5-yl)methanol.
Analytical chiral HPLC: $t_R$=9.898 min in 15 min chromatography (Method: OD-H_3_5_40_2.35 ML). LC-MS MS (ESI) m/z 472.2 [M+H]$^+$. $^1$H NMR (CD$_3$OD 400 MHz): δ 8.23 (s, 1H), 8.18 (s, 1H), 8.00 (s, 1H), 6.00 (d, J=8.0 Hz, 1H), 5.27-5.18 (m, 1H), 5.13 (s, 2H), 4.63 (s, 2H), 4.48-4.39 (m, 1H), 4.23-4.11 (m, 1H), 3.85-3.73 (m, 1H), 3.28 (s, 3H), 2.58-2.42 (m, 1H), 2.35-2.22 (m, 1H), 1.28 (d, J=6.8 Hz, 3H), 1.21-1.09 (m, 4H), 1.05 (d, J=6.8 Hz, 3H).

Isomer 2: (S)-(4-cyclopropyl-2-(8-(hydroxymethyl)-1-isopropyl-7-(methylsulfonyl)-3,4-dihydrobenzo[4,5]imidazo[1,2-a]pyrazin-2(1H)-yl)pyrimidin-5-yl)methanol.
Analytical chiral HPLC: $t_R$=10.770 min in 15 min chromatography (Method: OD-H_3_5_40_2.35 ML). LC-MS MS (ESI) m/z 472.2 [M+H]$^+$. $^1$H NMR (G000237343 901-086-P1 CD$_3$OD 400 MHz): δ 8.23 (s, 1H), 8.18 (s, 1H), 8.00 (s, 1H), 6.02 (d, J=8.0 Hz, 1H), 5.27-5.22 (m, 1H), 5.13 (s, 2H), 4.64 (s, 2H), 4.47-4.40 (m, 1H), 4.23-4.11 (m, 1H), 3.85-3.74 (m, 1H), 3.28 (s, 3H), 2.57-2.44 (m, 1H), 2.32-2.20 (m, 1H), 1.27 (d, J=6.8 Hz, 3H), 1.21-1.09 (m, 4H), 1.05 (d, J=6.8 Hz, 3H).

Example 21

(R)-(1-isopropyl-2-(5-methyl-4-(trifluoromethyl)pyrimidin-2-yl)-7-(methylsulfonyl)-1,2,3,4-tetrahydrobenzo[4,5]imidazo[1,2-a]pyrazin-8-yl)methanol

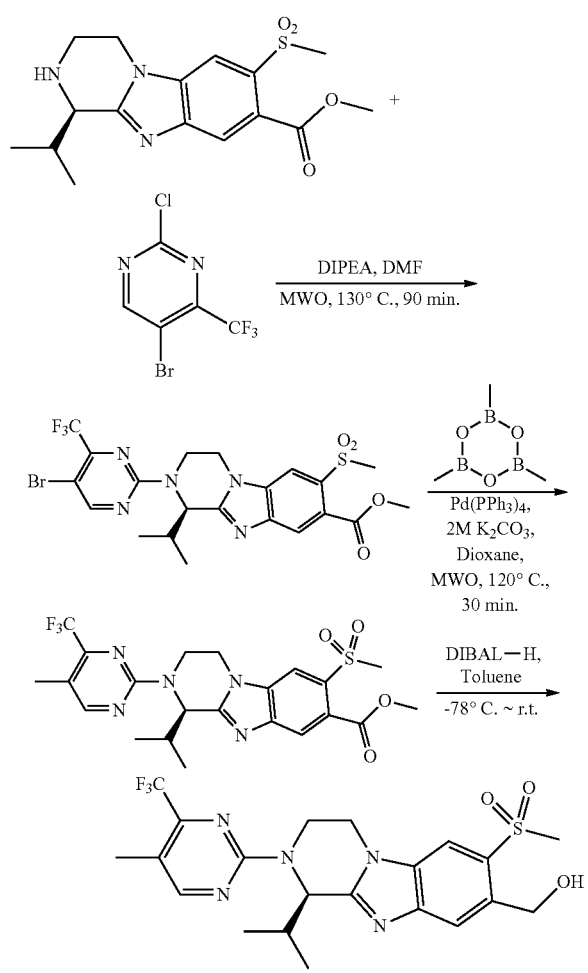

A mixture of (R)-methyl 1-isopropyl-7-(methylsulfonyl)-1,2,3,4-tetrahydrobenzo[4,5]imidazo[1,2-a]pyrazine-8-carboxylate (45 mg, 0.128 mmol), 5-bromo-2-chloro-4-(trifluoromethyl)pyrimidine (40 mg, 1.2 eq.), DIPEA (90 μL, 4 eq.) and DMF (1.5 mL) was put in Microwave Oven and heated 90 min. at 130° C. The mixture was participated between EtOAc and water. The aqueous layer was extracted twice by EtOAc. The combined organic layers were washed by brine, dried over Na$_2$SO$_4$. After filtration and concentration, the residue was purified by ISCO (12 g column, 10-40% EtOAc in Hexanes) to afford 34.4 mg (47% yield) of (R)-methyl 2-(4-bromo-3-(trifluoromethyl)phenyl)-1-isopropyl-7-(methylsulfonyl)-1,2,3,4-tetrahydrobenzo[4,5]imidazo[1,2-a]pyrazine-8-carboxylate.

A mixture of (R)-methyl 2-(5-bromo-4-(trifluoromethyl)pyrimidin-2-yl)-1-isopropyl-7-(methylsulfonyl)-1,2,3,4-tetrahydrobenzo[4,5]imidazo[1,2-a]pyrazine-8-carboxylate (7 mg, 0.012 mmol), Pd(PPh$_3$)$_4$ (1 mg, cat. Amount), 2M aq. K$_2$CO$_3$ solution (100 μL, excess), and dry 1,4-Dioxane (700 μL) was degassed and refilled with nitrogen gas for 3 times. A solution of 2,4,6-trimethyl-1,3,5,2,4,6-trioxatriborinane (5 mg, excess) in dry 1,4-Dioxane (100 μL) was added. The mixture was heated in a microwave oven for 30 minutes at 120° C. After concentration, the residue was filtered and purified by Gilson to afford 3.5 mg (R)-methyl 1-isopropyl-2-(5-methyl-4-(trifluoromethyl)pyrimidin-2-yl)-7-(methylsulfonyl)-1,2,3,4-tetrahydrobenzo[4,5]imidazo[1,2-a]pyrazine-8-carboxylate (56% yield). LC-MS: m/z 512.3 [M+H]$^+$.

A solution of (R)-methyl 1-isopropyl-2-(5-methyl-4-(trifluoromethyl)pyrimidin-2-yl)-7-(methylsulfonyl)-1,2,3,4-tetrahydrobenzo[4,5]imidazo[1,2-a]pyrazine-8-carboxylate (3.5 mg, 0.007 mmol) in dry toluene (3 mL) was cooled to −78° C. A solution of DIBAL-H in toluene (1M, 35 μL, 5 equiv.) was added. The mixture was stirred for 3 h. LC-MS indicated the reaction was complete. The mixture was quenched by sat. NH$_4$Cl solution (200 μL) and methanol (200 μL), before being warmed to r.t. After concentration, the residue was filtered and purified by Gilson to afford 1.53 mg (R)-(1-isopropyl-2-(5-methyl-4-(trifluoromethyl)pyrimidin-2-yl)-7-(methylsulfonyl)-1,2,3,4-tetrahydrobenzo[4,5]imidazo[1,2-a]pyrazin-8-yl)methanol (46% yield). LC-MS: m/z 484.3 [M+H]$^+$. $^1$H NMR (CD$_3$OD, 400 MHz): δ 8.52 (s, 1H), 8.27 (s, 1H), 7.99 (s, 1H), 6.05 (d, J=8.0 Hz, 1H), 5.30 (dd, J=14.4 Hz, 4.8 Hz, 1H), 5.12 (s, 2H), 4.51 (dd, J=12.0 Hz, 3.2 Hz, 1H), 4.22 (td, 12.0 Hz, 5.2 Hz, 1H), 3.88 (m, 1H), 3.26 (s, 1H), 2.57 (m, 1H), 2.29 (s, 3H), 1.27 (d, 6.4 Hz, 3H), 1.06 (d, 6.4 Hz, 3H).

Example 22

(R)-1-(2-(1-isopropyl-7-(methylsulfonyl)-3,4-dihydropyrazino[1,2-a]indol-2(1H)-yl)-4-(trifluoromethyl)pyrimidin-5-yl)ethanone and (S)-1-(2-(1-isopropyl-7-(methylsulfonyl)-3,4-dihydropyrazino[1,2-a]indol-2(1H)-yl)-4-(trifluoromethyl)pyrimidin-5-yl)ethanone

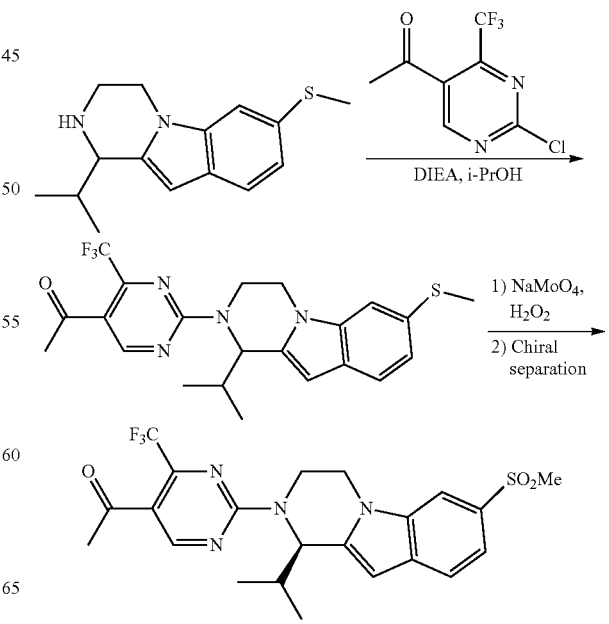

-continued

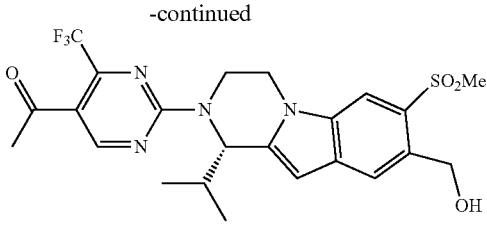

To a solution of 1-isopropyl-7-(methylthio)-1,2,3,4-tetrahydropyrazino[1,2-a]indole (100 mg, 0.38 mmol) and DIPEA (246.72 mg, 1.91 mmol) in i-PrOH (2 mL) was added 1-(2-chloro-4-(trifluoromethyl)pyrimidin-5-yl)ethanone (172.50 mg, 0.76 mmol). The reaction mixture was stirred at rt overnight. The mixture was concentrated and purified by preparative TLC on silica gel eluting with PE/EtOAc 1:1 to afford 1-(2-(1-isopropyl-7-(methylthio)-3,4-dihydropyrazino[1,2-a]indol-2(1H)-yl)-4-(trifluoromethyl)pyrimidin-5-yl)ethanone (120 mg, 69.67% yield) as a colorless oil. LC-MS MS (ESI) m/z 449.2 [M+H]+. 1H NMR (CDCl3 400 MHz): δ 8.66 (s, 1H), 7.44-7.40 (m, 1H), 7.06 (d, J=8.4 Hz, 1H), 6.27-6.25 (m, 1H), 5.79-577 (m, 1H), 5.13-5.02 (m, 1H), 4.21-4.16 (m, 1H), 3.97-3.91 (m, 1H), 3.82-3.71 (m, 1H), 2.48 (s, 3H), 2.46 (s, 3H), 2.21-2.15 (m, 1H), 1.12-1.08 (m, 3H), 0.96-0.93 (m, 3H).

To a solution of 1-(2-(1-isopropyl-7-(methylthio)-3,4-dihydropyrazino[1,2-a]indol-2(1H)-yl)-4-(trifluoromethyl)pyrimidin-5-yl)ethanone (110 mg, 0.23 mmol) in methanol (3 mL) at 0° C. was added NaMoO4-2H2O (107.61 mg, 0.49 mmol). The reaction mixture was stirred at 0° C. for 10 min. Then H2O2 (5 mL, 30% wt) was added to the formed mixture. The mixture was stirred at rt for 1 h. The mixture was extracted with a mixture solvent of dichloromethane (30 mL)/i-PrOH (10 mL) three times. The combined organic layers were concentrated, purified by preparative TLC on silica gel eluting with PE/EtOAc 1:1 and purified by SFC separation to afford (R)-1-(2-(1-isopropyl-7-(methylsulfonyl)-3,4-dihydropyrazino[1,2-a]indol-2(1H)-yl)-4-(trifluoromethyl)pyrimidin-5-yl)ethanone (26.90 mg, 22.38% yield, isomer 1) as a colorless oil and (S)-1-(2-(1-isopropyl-7-(methylsulfonyl)-3,4-dihydropyrazino[1,2-a]indol-2(1H)-yl)-4-(trifluoromethyl)pyrimidin-5-yl)ethanone (23.80 mg, 20.20% yield, isomer 2) as a colorless oil.

Isomer 1: (R)-1-(2-(1-isopropyl-7-(methylsulfonyl)-3,4-dihydropyrazino[1,2-a]indol-2(1H)-yl)-4-(trifluoromethyl)pyrimidin-5-yl)ethanone. Analytical chiral HPLC: $t_R$=7.972 min in 15 min chromatography (Method: AD-H_5_5_40_2.35 ML). LC-MS (ESI) m/z 481.2 [M+H]+, 503.1 [M+Na]. 1H NMR (CDCl3 400 MHz): δ 8.75-8.73 (m, 1H), 7.95 (s, 1H), 7.72 (d, J=8.4 Hz, 1H), 7.65 (d, J1=8.4 Hz, J2=1.6 Hz, 1H), 6.51-6.48 (m, 1H), 5.94-5.92 (m, 1H), 5.25-5.22 (m, 1H), 4.41-4.36 (m, 1H), 4.15-4.10 (m, 1H), 3.88-3.84 (m, 1H), 3.08 (s, 3H), 2.54 (s, 3H), 2.34-2.27 (m, 1H), 1.21-1.18 (m, 3H), 1.06-1.05 (m, 3H).

Isomer 2: (R)-1-(2-(1-isopropyl-7-(methylsulfonyl)-3,4-dihydropyrazino[1,2-a]indol-2(1H)-yl)-4-(trifluoromethyl)pyrimidin-5-yl)ethanone. Analytical chiral HPLC: $t_R$=11.077 min in 15 min chromatography (Method: AD-H_5_5_40_2.35 ML). LC-MS MS (ESI) m/z 481.1 [M+H]+, 503.1 [M+Na]+. 1H NMR (CDCl3 400 MHz): δ 8.75-8.73 (m, 1H), 7.95 (s, 1H), 7.73-7.70 (m, 1H), 7.65 (d, J1=8.4 Hz, J2=1.6 Hz, 1H), 6.51-6.48 (m, 1H), 5.94-5.92 (m, 1H), 5.25-5.22 (m, 1H), 4.41-4.36 (m, 1H), 4.15-4.10 (m, 1H), 3.88-3.84 (m, 1H), 3.08 (s, 3H), 2.54 (s, 3H), 2.34-2.27 (m, 1H), 1.21-1.18 (m, 3H), 1.07-1.05 (m, 3H).

Example 23

(R)-2-(2-(1-isopropyl-7-(methylsulfonyl)-3,4-dihydropyrazino[1,2-a]indol-2(1H)-yl)-4-(trifluoromethyl)pyrimidin-5-yl)propan-2-ol and (S)-2-(2-(1-isopropyl-7-(methylsulfonyl)-3,4-dihydropyrazino[1,2-a]indol-2(1H)-yl)-4-(trifluoromethyl)pyrimidin-5-yl)propan-2-ol

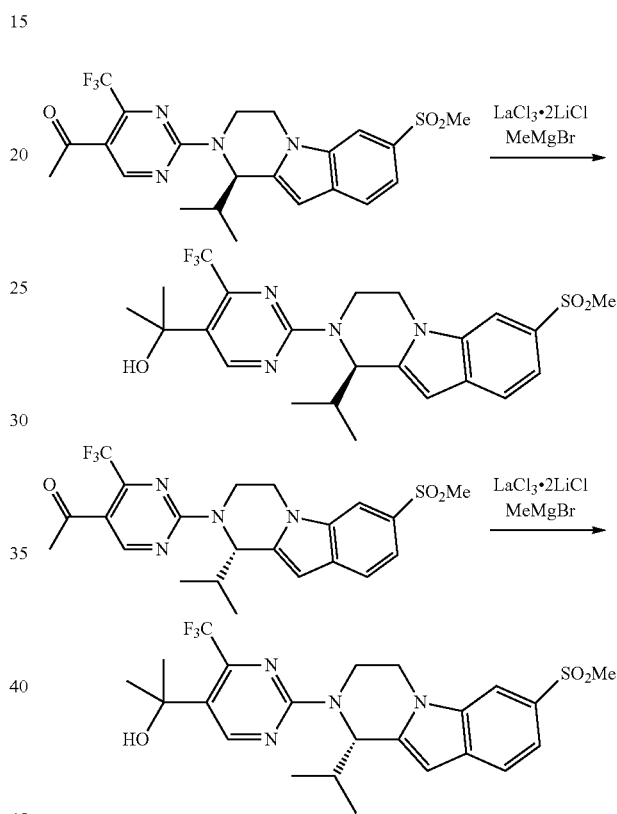

To a solution of (R)-1-(2-(1-isopropyl-7-(methylsulfonyl)-3,4-dihydropyrazino[1,2-a]indol-2(1H)-yl)-4-(trifluoromethyl)pyrimidin-5-yl)ethanone (5 mg, 0.01 mmol) in THF (1 mL) was added LaCl3-2LiCl (0.2 mL, 0.12 mmol, 0.6M) at 0° C. under nitrogen. The reaction mixture was stirred at 0° C. for 1 h. MeMgCl (0.3 mL, 0.9 mmol, 3M) was added to the formed mixture and then the reaction mixture was stirred at 0° C. for 1 h. The reaction was quenched with sat. NH4Cl (5 mL) at 0° C. and then extracted with EtOAc (30 mL×3). The combined organic layers were dried over anhydrous Na2SO4, filtered and concentrated, purified by preparative TLC eluting with PE/EtOAc 1:1 and then by SFC separation to afford (R)-2-(2-(1-isopropyl-7-(methylsulfonyl)-3,4-dihydropyrazino[1,2-a]indol-2(1H)-yl)-4-(trifluoromethyl)pyrimidin-5-yl)propan-2-ol (1.20 mg, 24.68% yield, Isomer 1) as a colorless oil. Analytical chiral HPLC: $t_R$=6.394 min in 15 min chromatography (Method: OJ-H_3_5_40_2.35 ML). LC-MS m/z 497.3 [M+H]+. 1H NMR (CDCl3 400 MHz): δ 8.75 (s, 1H), 7.93 (s, 1H), 7.70 (d, J=8.4 Hz, 1H), 7.62 (d, J1=8.4 Hz, J2=1.6 Hz, 1H), 6.48 (s, 1H), 5.89 (d, J=8.8 Hz, 1H), 5.16-5.12 (m, 1H), 4.32-4.28 (m, 1H), 4.14-4.07 (m, 1H), 3.86-3.77 (m, 1H), 3.07 (s, 3H), 2.34-2.25 (m, 1H), 1.92 (s, 1H), 1.68 (s, 6H), 1.18 (d, J=7.2 Hz, 3H), 1.06 (d, J=7.2 Hz, 3H)

The (S)-2-(2-(1-isopropyl-7-(methylsulfonyl)-3,4-dihydropyrazino[1,2-a]indol-2(1H)-yl)-4-(trifluoromethyl)pyrimidin-5-yl)propan-2-ol (Isomer 2) was prepared in similar manner from (S)-1-(2-(1-isopropyl-7-(methylsulfonyl)-3,4-dihydropyrazino[1,2-a]indol-2(1H)-yl)-4-(trifluoromethyl)pyrimidin-5-yl)ethanone. Analytical chiral HPLC: $t_R$=7.631 min in 15 min chromatography (Method: AS-H_3_5_40_ 2.35 ML). LC-MS m/z 497.2 [M+H]$^+$. $^1$H NMR (CDCl$_3$ 400 MHz): δ 8.75 (s, 1H), 7.93 (s, 1H), 7.70 (d, J=8.4 Hz, 1H), 7.62 (d, J$_1$=8.4 Hz, J$_2$=1.6 Hz, 1H), 6.48 (s, 1H), 5.89 (d, J=8.8 Hz, 1H), 5.16-5.12 (m, 1H), 4.32-4.28 (m, 1H), 4.14-4.07 (m, 1H), 3.86-3.77 (m, 1H), 3.07 (s, 3H), 2.34-2.25 (m, 1H), 1.92 (s, 1H), 1.68 (s, 6H), 1.18 (d, J=7.2 Hz, 3H), 1.06 (d, J=7.2 Hz, 3H).

Example 24

1-(2-(1-isopropyl-7-(methylsulfonyl)-3,4-dihydropyrazino[1,2-a]indol-2(1H)-yl)-4-(trifluoromethyl)pyrimidin-5-yl)ethanol (4 isomers)

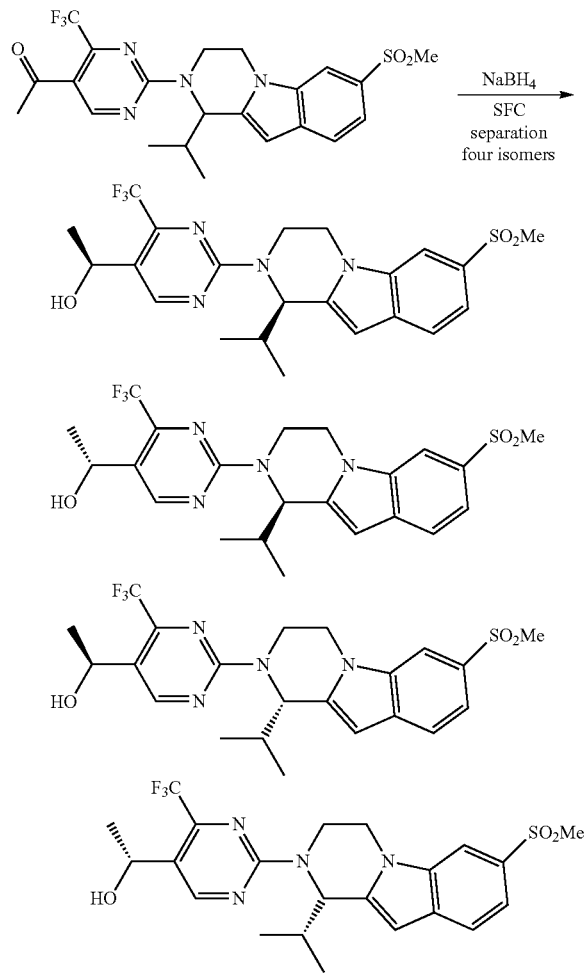

To a solution of 1-(2-(1-isopropyl-7-(methylsulfonyl)-3,4-dihydropyrazino[1,2-a]indol-2(1H)-yl)-4-(trifluoromethyl)pyrimidin-5-yl)ethanone (10 mg, 21 μmol) in methanol (2 mL) was added NaBH$_4$ (7.8 mg, 0.21 mmol) at 0° C. The reaction mixture was stirred at reflux for 2 h. The mixture was quenched with water (5 mL) and concentrated to remove methanol to give crude product which was extracted with EtOAc (30 mL×3). The combined organic layers were dried over anhydrous Na2SO4, filtered, concentrated and purified by preparative TLC on silica gel eluting with PE/EtOAc 1:1 and then by SFC separation to afford Isomer 1 (0.80 mg, 7.97% yield) as a colorless oil, Isomer 2 (0.90 mg, 8.96% yield) as a colorless oil, Isomer 3 (1.20 mg, 11.95% yield) as a colorless oil and Isomer 4 (1.30 mg, 12.94% yield) as a colorless oil.

Isomer 1: Analytical chiral HPLC: $t_R$=3.16 min in 15 min chromatography (Method: AD-H_3_30%_2.35 ML). LC-MS m/z 483.0 [M+H]$^+$. $^1$H NMR (CDCl$_3$ 400 MHz): δ 8.83 (s, 1H), 7.93 (s, 1H), 7.68 (d, J=7.2 Hz, 1H), 7.52 (d, J=7.2 Hz, 1H), 6.47 (s, 1H), 5.89 (d, J=8.8 Hz, 1H), 5.24-5.14 (m, 2H), 4.33-4.31 (m, 1H), 4.16-4.09 (m, 1H), 3.85-3.81 (m, 1H), 3.08 (s, 3H), 2.36-2.29 (m, 1H), 1.53-1.51 (m, 3H), 1.19 (d, J=6.4 Hz, 3H), 1.07 (d, J=6.8 Hz, 3H).

Isomer 2: Analytical chiral HPLC: $t_R$=4.04 min in 15 min chromatography (Method: AD-H_3_30%_2.35 ML). LC-MS m/z 483.0 [M+H]$^+$. $^1$H NMR (CDCl$_3$ 400 MHz): δ 8.83 (s, 1H), 7.93 (s, 1H), 7.68 (d, J=7.2 Hz, 1H), 7.52 (d, J=7.2 Hz, 1H), 6.47 (s, 1H), 5.89 (d, J=8.8 Hz, 1H), 5.24-5.14 (m, 2H), 4.33-4.31 (m, 1H), 4.16-4.09 (m, 1H), 3.85-3.81 (m, 1H), 3.08 (s, 3H), 2.36-2.29 (m, 1H), 1.53-1.51 (m, 3H), 1.19 (d, J=6.4 Hz, 3H), 1.07 (d, J=6.8 Hz, 3H).

Isomer 3: Analytical chiral HPLC: $t_R$=6.08 min in 15 min chromatography (Method: AD-H_3_30%_2.35 ML). LC-MS m/z 483.0 [M+H]$^+$. $^1$H NMR (CDCl$_3$ 400 MHz): δ 8.83 (s, 1H), 7.93 (s, 1H), 7.68 (d, J=7.2 Hz, 1H), 7.61 (d, J=7.2 Hz, 1H), 6.47 (s, 1H), 5.89 (d, J=8.8 Hz, 1H), 5.24-5.14 (m, 2H), 4.33-4.31 (m, 1H), 4.16-4.09 (m, 1H), 3.85-3.81 (m, 1H), 3.08 (s, 3H), 2.36-2.29 (m, 1H), 1.53-1.51 (m, 3H), 1.19 (d, J=6.4 Hz, 3H), 1.07 (d, J=6.8 Hz, 3H).

Isomer 4: Analytical chiral HPLC: $t_R$=10.21 min in 15 min chromatography (Method: AD-H_3_30%_2.35 ML). LC-MS m/z 483.0 [M+H]$^+$. $^1$H NMR (CDCl$_3$ 400 MHz): δ 8.84 (s, 1H), 7.93 (s, 1H), 7.68 (d, J=7.2 Hz, 1H), 7.61 (d, J=7.2 Hz, 1H), 6.47 (s, 1H), 5.89 (d, J=8.8 Hz, 1H), 5.24-5.14 (m, 2H), 4.33-4.31 (m, 1H), 4.16-4.09 (m, 1H), 3.85-3.81 (m, 1H), 3.08 (s, 3H), 2.36-2.29 (m, 1H), 1.53-1.51 (m, 3H), 1.19 (d, J=6.4 Hz, 3H), 1.07 (d, J=6.8 Hz, 3H).

Example 25

(R)-(2-(1-isopropyl-7-(methylsulfonyl)-3,4-dihydropyrazino[1,2-a]indol-2(1H)-yl)-4-(trifluoromethyl)pyrimidin-5-yl)methanol and (S)-(2-(1-isopropyl-7-(methylsulfonyl)-3,4-dihydropyrazino[1,2-a]indol-2(1H)-yl)-4-(trifluoromethyl)pyrimidin-5-yl)methanol

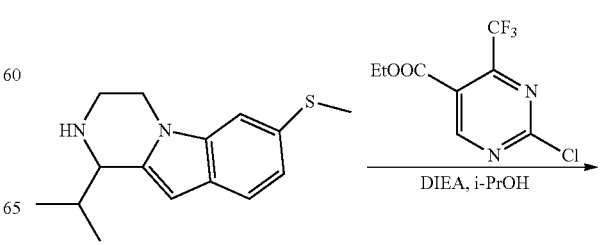

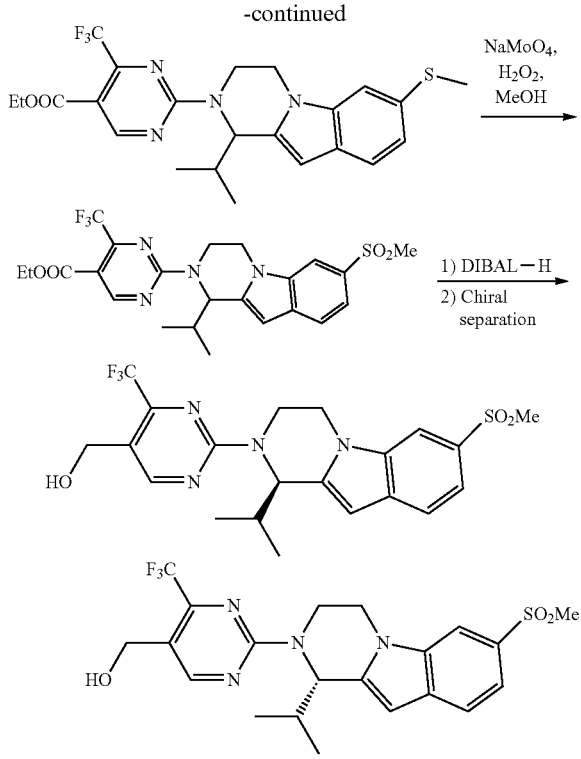

To a solution of 1-isopropyl-7-(methylthio)-1,2,3,4-tetrahydropyrazino[1,2-a]indole (100 mg, 0.38 mmol) and DIPEA (248.3 mg, 1.921 mmol) in i-PrOH (3 mL) was added ethyl 2-chloro-4-(trifluoromethyl)pyrimidine-5-carboxylate (196 mg, 0.77 mmol). The reaction mixture was stirred at rt overnight. The mixture was concentrated and purified by preparative TLC on silica gel eluting with PE/EtOAc 1:1 to afford ethyl 2-(1-isopropyl-7-(methylthio)-3,4-dihydropyrazino[1,2-a]indol-2(1H)-yl)-4-(trifluoromethyl)pyrimidine-5-carboxylate (60 mg, 32.6% yield) as a colorless oil. LC-MS MS (ESI) m/z 478.7 [M+H]+.

To a solution of ethyl 2-(1-isopropyl-7-(methylthio)-3,4-dihydropyrazino[1,2-a]indol-2(1H)-yl)-4-(trifluoromethyl)pyrimidine-5-carboxylate (54 mg, 0.11 mmol) in methanol (2 mL) at 0° C. was added NaMoO$_4$-2H$_2$O (54 mg, 0.24 mmol). The reaction mixture was stirred at 0° C. for 10 min. H$_2$O$_2$ (2 mL, 30% wt) was added to the formed mixture. The mixture was stirred at rt for 1 h. The mixture was extracted with a mixture solvent of dichloromethane (30 mL)/i-PrOH (10 mL) three times. The combined organic layers were concentrated, purified by preparative TLC eluting with PE/EtOAc 1:1 to afford ethyl 2-(1-isopropyl-7-(methylsulfonyl)-3,4-dihydropyrazino[1,2-a]indol-2(1H)-yl)-4-(trifluoromethyl)pyrimidine-5-carboxylate (25 mg, 43.39% yield) as a white solid. LC-MS MS (ESI) m/z 511.1 [M+H]+.

To a solution of 2-(1-isopropyl-7-(methylsulfonyl)-3,4-dihydropyrazino[1,2-a]indol-2(1H)-yl)-4-(trifluoromethyl)pyrimidine-5-carboxylate (25 mg, 0.05 mmol) in dichloromethane (1 mL) was added DIBAL-H (0.25 mg, 0.25 mmol, 1M in toluene) at −78° C. under nitrogen. The reaction mixture was stirred at −78° C. for 1 h. The reaction was quenched with sat. NH$_4$Cl (5 mL) at −78° C. and then extracted with dichloromethane (30 mL×3). The combined organic layers were concentrated, purified by preparative TLC on silica gel eluting with PE/EtOAc 1:1 and then by SFC separation to afford (R)-(2-(1-isopropyl-7-(methylsulfonyl)-3,4-dihydropyrazino[1,2-a]indol-2(1H)-yl)-4-(trifluoromethyl)pyrimidin-5-yl)methanol (1.80 mg, 7.84% yield, isomer 1) as a colorless oil and (S)-(2-(1-isopropyl-7-(methylsulfonyl)-3,4-dihydropyrazino[1,2-a]indol-2(1H)-yl)-4-(trifluoromethyl)pyrimidin-5-yl)methanol (1.60 mg, 6.97% yield, isomer 2) as a colorless oil.

Isomer 1: (R)-(2-(1-isopropyl-7-(methylsulfonyl)-3,4-dihydropyrazino[1,2-a]indol-2(1H)-yl)-4-(trifluoromethyl)pyrimidin-5-yl)methanol. Analytical chiral HPLC: t$_R$=8.1 min in 15 min chromatography (Method: OD-3_5_5_40_2.5 ML). LC-MS m/z 469.0 [M+H]+. $^1$H NMR (CDCl$_3$ 400 MHz): δ 8.63 (s, 1H), 7.94 (s, 1H), 7.70 (d, J=8.4 Hz, 1H), 7.63 (d, J$_1$=8.4 Hz, J$_2$=1.6 Hz, 1H), 6.48 (s, 1H), 5.89 (d, J=8.8 Hz, 1H), 5.19-5.14 (m, 1H), 4.71 (d, J=4.8 Hz, 2H), 3.86-3.82 (m, 1H), 4.14-4.07 (m, 1H), 3.86-3.77 (m, 1H), 3.07 (s, 3H), 2.34-2.25 (m, 1H), 1.82-1.78 (m, 1H), 1.18 (d, J=7.2 Hz, 3H), 1.04 (d, J=7.2 Hz, 3H).

Isomer 2: (S)-(2-(1-isopropyl-7-(methylsulfonyl)-3,4-dihydropyrazino[1,2-a]indol-2(1H)-yl)-4-(trifluoromethyl)pyrimidin-5-yl)methanol. Analytical chiral HPLC: t$_R$=11.33 min in 15 min chromatography (Method: OD-3_5_5_40_2.5 ML). LC-MS m/z 469.1 [M+H]+. $^1$H NMR (CDCl$_3$ 400 MHz): δ 8.63 (s, 1H), 7.94 (s, 1H), 7.70 (d, J=8.4 Hz, 1H), 7.63 (d, J$_1$=8.4 Hz, J$_2$=1.6 Hz, 1H), 6.48 (s, 1H), 5.89 (d, J=8.8 Hz, 1H), 5.19-5.14 (m, 1H), 4.71 (s, 2H), 3.86-3.82 (m, 1H), 4.14-4.07 (m, 1H), 3.86-3.77 (m, 1H), 3.07 (s, 3H), 2.34-2.25 (m, 1H), 1.82-1.78 (m, 1H), 1.18 (d, J=7.2 Hz, 3H), 1.04 (d, J=7.2 Hz, 3H).

Example 26

(±)-1-(2-(8-(hydroxymethyl)-1-isopropyl-7-(methylsulfonyl)-3,4-dihydropyrazino[1,2-a]indol-2(1H)-yl)-4-(trifluoromethyl)pyrimidin-5-yl)ethanone

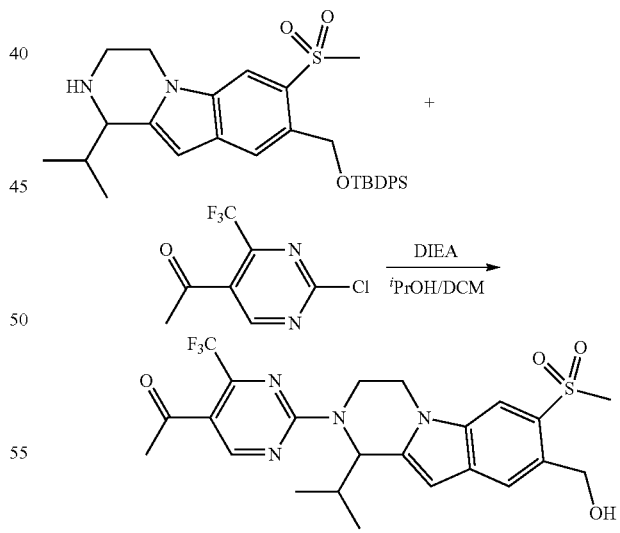

The intermediate 8-(((tert-butyldiphenylsilyl)oxy)methyl)-1-isopropyl-7-(methylsulfonyl)-1,2,3,4-tetrahydropyrazino[1,2-a]indole was prepared following a procedure analogous to that described in Preparation 4. The mixture of compound 8-(((tert-butyldiphenylsilyl)oxy)methyl)-1-isopropyl-7-(methylsulfonyl)-1,2,3,4-tetrahydropyrazino[1,2-a]indole (0.22 mmol), 1-(2-chloro-4-(trifluoromethyl)pyrimidin-5-yl)ethanone (100 mg, 0.44 mmol) and DIEA (115

μL, 0.66 mmol) in i-PrOH/CH$_2$Cl$_2$ (2 mL/1 mL) was stirred at 60° C. for 15 h. The solvent was removed under reduced pressure and the residue was purified by column chromatography on silica gel eluting with EtOAc/hexanes (1/1) to give racemic 1-(2-(8-(hydroxymethyl)-1-isopropyl-7-(methylsulfonyl)-3,4-dihydropyrazino[1,2-a]indol-2(1H)-yl)-4-(trifluoromethyl)pyrimidin-5-yl)ethanone. LC-MS m/z 510 [M+H]$^+$. $^1$H NMR (400 MHz, CD$_3$OD): δ 8.97 (s, 1H), 8.11 (s, 1H), 7.80 (s, 1H), 6.54 (s, 1H), 6.01-5.90 (m, 1H), 5.25-5.15 (m, 1H), 5.07 (s, 2H), 4.52-4.47 (m, 1H), 4.15-4.04 (m, 1H), 4.00-3.93 (m, 1H), 3.26 (s, 3H), 2.55 (s, 3H), 2.41-2.32 (m, 1H), 1.18 (d, J=6.8 Hz, 3H), 1.03 (d, J=6.8 Hz, 3H).

Example 27

(R)-2-(2-(8-(hydroxymethyl)-1-isopropyl-7-(methylsulfonyl)-3,4-dihydropyrazino[1,2-a]indol-2(1H)-yl)-4-(trifluoromethyl)pyrimidin-5-yl)propan-2-ol and (S)-2-(2-(8-(hydroxymethyl)-1-isopropyl-7-(methylsulfonyl)-3,4-dihydropyrazino[1,2-a]indol-2(1H)-yl)-4-(trifluoromethyl)pyrimidin-5-yl)propan-2-ol

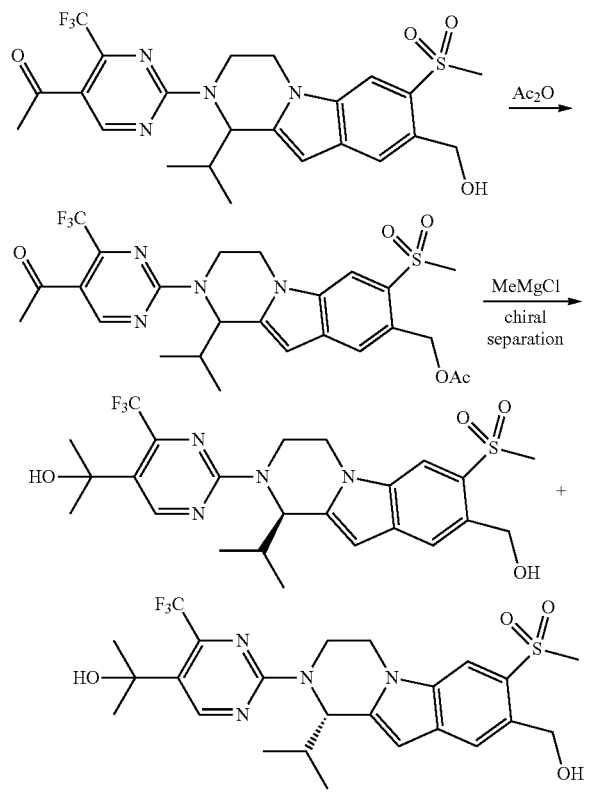

To a solution of 1-(2-(8-(hydroxymethyl)-1-isopropyl-7-(methylsulfonyl)-3,4-dihydropyrazino[1,2-a]indol-2(1H)-yl)-4-(trifluoromethyl)pyrimidin-5-yl)ethanone (132 mg, 0.26 mmol) in CH$_2$Cl$_2$ (5 mL) was added pyridine (1 mL) and AcCl (130 μL, 1.3 mmol). The mixture was stirred at rt for 10 h. The reaction was quenched with water (5 mL). The aqueous layer was extracted with CH$_2$Cl$_2$ (3×10 mL). The combined organic layers were washed with brine, and then dried over anhydrous Na$_2$SO$_4$. The mixture was filtered and concentrated under reduced pressure. The residue was purified by column chromatography on silica gel eluting with hexanes/EtOAc (1/1) to give (2-(5-acetyl-4-(trifluoromethyl)pyrimidin-2-yl)-1-isopropyl-7-(methylsulfonyl)-1,2,3,4-tetrahydropyrazino[1,2-a]indol-8-yl)methyl acetate. LC-MS m/z 553 [M+H]$^+$.

To a solution of (2-(5-acetyl-4-(trifluoromethyl)pyrimidin-2-yl)-1-isopropyl-7-(methylsulfonyl)-1,2,3,4-tetrahydropyrazino[1,2-a]indol-8-yl)methyl acetate (37 mg, 67 μmol) in dry THF (2 mL) was added LaCl3.2 LiCl THF solution (0.12 mL, 70 μmol). The resulting mixture was stirred for 20 min at rt. The reaction mixture was cooled down to 0° C., MeMgCl in THF solution (3.0 M, 0.15 mL) was added slowly and the reaction mixture was allowed to stir at the same temperature for 0.5 h. Sat. aq. NH$_4$Cl (1 mL) and water (2 mL) were added. The aqueous layer was extracted with EtOAc (4×10 mL). Combined organic phases were dried (Na$_2$SO$_4$) and concentrated. The crude residue was purified by silica chromatography and SFC separation to give isomers of 2-(2-(8-(hydroxymethyl)-1-isopropyl-7-(methylsulfonyl)-3,4-dihydropyrazino[1,2-a]indol-2(1H)-yl)-4-(trifluoromethyl)pyrimidin-5-yl)propan-2-ol.

Isomer 1: Analytical chiral HPLC: t$_R$=12.31 min in 15 min chromatography (Method: OD-H_5_5_40_2.35 ML). LC-MS m/z 527 [M+H]$^+$. $^1$H NMR (400 MHz, CD$_3$OD): δ 8.83 (s, 1H), 8.08 (s, 1H), 7.77 (s, 1H), 6.50 (s, 1H), 5.87 (d, J=8.4 Hz, 1H), 5.10 (m, 1H), 5.06 (s, 2H), 4.44-4.40 (m, 1H), 4.09-4.02 (m, 1H), 3.91-3.84 (m, 1H), 3.26 (s, 3H), 2.36-2.29 (m, 1H), 1.59 (s, 6H), 1.16 (d, J=6.8 Hz, 3H), 1.02 (d, J=6.8 Hz, 3H).

Isomer 2: Analytical chiral HPLC: t$_R$=8.65 min in 15 min chromatography (Method: OD-H_5_5_40_2.35 ML). LC-MS m/z 527 [M+H]$^+$. $^1$H NMR (400 MHz, CD$_3$OD): δ 8.83 (s, 1H), 8.08 (s, 1H), 7.77 (s, 1H), 6.50 (s, 1H), 5.87 (d, J=8.4 Hz, 1H), 5.10 (m, 1H), 5.06 (s, 2H), 4.44-4.40 (m, 1H), 4.09-4.02 (m, 1H), 3.91-3.84 (m, 1H), 3.26 (s, 3H), 2.36-2.29 (m, 1H), 1.59 (s, 6H), 1.16 (d, J=6.8 Hz, 3H), 3 1.02 (d, J=6.8 Hz, 3H).

Example 28

(±)-Ethyl 2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxylate

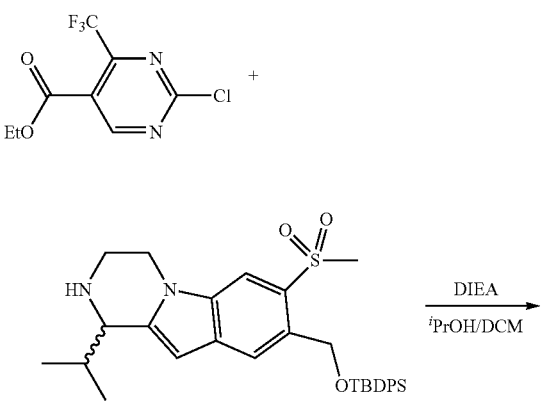

-continued

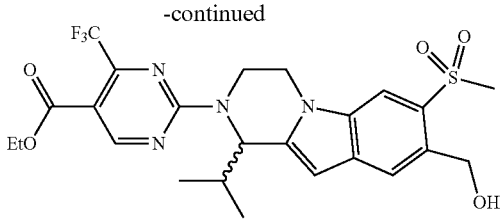

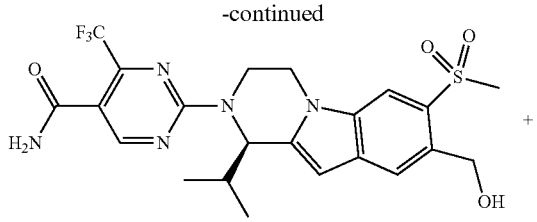

The intermediate 8-((((tert-butyldiphenylsilyl)oxy)methyl)-1-isopropyl-7-(methylsulfonyl)-1,2,3,4-tetrahydropyrazino[1,2-a]indole was prepared following a procedure analogous to that described in Preparation 4. The mixture of compound 8-((((tert-butyldiphenylsilyl)oxy)methyl)-1-isopropyl-7-(methylsulfonyl)-1,2,3,4-tetrahydropyrazino[1,2-a]indole (0.19 mmol), ethyl 2-chloro-4-(trifluoromethyl)pyrimidine-5-carboxylate (97 mg, 0.38 mmol) and DIEA (100 μL, 0.57 mmol) in i-PrOH/CH$_2$Cl$_2$ (1 mL/0.5 mL) was stirred at 50° C. for 8 h. The solvent was removed under reduced pressure and the residue was purified by column chromatography on silica gel eluting with EtOAc/hexanes (1/1) to give racemic ethyl 2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxylate. LC-MS m/z 563 [M+Na]$^+$. $^1$H NMR (400 MHz, CD$_3$OD): δ 9.31 (s, 1H), 8.11 (s, 1H), 7.80 (s, 1H), 6.55 (s, 1H), 6.02-5.92 (m, 1H), 5.23-5.17 (m, 1H), 5.07 (s, 2H), 4.52-4.47 (m, 1H), 4.34 (q, J=7.2 Hz, 2H), 4.19-4.06 (m, 1H), 4.00-3.93 (m, 1H), 3.27 (s, 3H), 2.42-2.32 (m, 1H), 1.36 (t, J=7.2 Hz, 3H), 1.18 (d, J=6.8 Hz, 3H), 1.03 (d, J=6.8 Hz, 3H).

Example 29

(R)-2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxamide and (S)-2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxamide

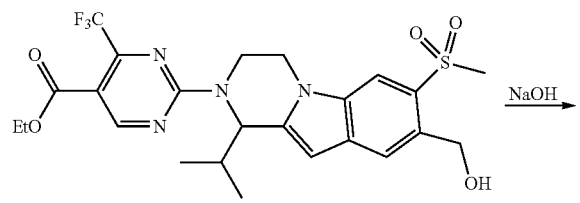
NaOH →

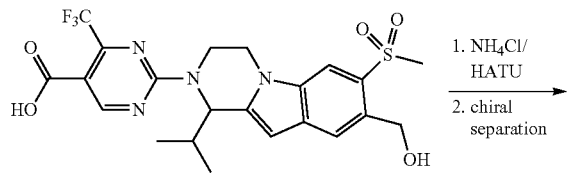
1. NH$_4$Cl/HATU
2. chiral separation →

To a solution of ethyl 2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxylate (30 mg, 55 μmol) in THF (1 mL) was added 1 N NaOH aqueous solution (1 mL). The resulting mixture was stirred at rt for 3 h. The reaction mixture was acidified with 1N HCl solution (1.5 mL). The mixture was extracted with CH$_2$Cl$_2$ (4×5 mL). The combined organic solution was washed with brine, dried over anhydrous Na$_2$SO$_4$, filtered and concentrated under reduced pressure to provide 2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxylic acid. It was used directly without further purification.

To a stirred solution of 2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxylic acid (55 μmol) in anhydrous DMF (1 mL) was added HATU (42 mg, 0.11 mmol), NH$_4$Cl (30 mg, 0.55 mmol) and N,N-diisopropylethylamine (100 μL, 0.55 mmol). The mixture was stirred at rt for 20 h. It was diluted with CH$_2$Cl$_2$ (10 mL) and washed with H$_2$O. The organic layer was separated, and the aqueous layer was extracted with CH$_2$Cl$_2$ (3×10 mL). The combined organic solution was washed with brine, dried over anhydrous Na$_2$SO$_4$, filtered and concentrated under reduced pressure. The crude residue was purified by silica chromatography and SFC separation to give isomers of 2-(8-(hydroxymethyl)-1-isopropyl-7-(methylsulfonyl)-3,4-dihydropyrazino[1,2-a]indol-2(1H)-yl)-4-(trifluoromethyl)pyrimidine-5-carboxamide.

Isomer 1: Analytical chiral HPLC: $t_R$=2.92 min in 8 min chromatography (Method: AS-H_S_3_40_3 ML). LC-MS m/z 494 [M+H-18]$^+$, 512 [M+H]$^+$. $^1$H NMR (400 MHz, CD$_3$OD): δ 8.68 (s, 1H), 8.12 (s, 1H), 7.80 (s, 1H), 6.54 (s, 1H), 6.00-5.87 (m, 1H), 5.20-5.08 (m, 1H), 5.07 (s, 2H), 4.50-4.46 (m, 1H), 4.14-4.08 (m, 1H), 3.98-3.90 (m, 1H), 3.27 (s, 3H), 2.39-2.32 (m, 1H), 1.29 (s, 2H), 1.18 (d, J=6.8 Hz, 3H), 1.04 (d, J=6.8 Hz, 3H).

Isomer 2: Analytical chiral HPLC: $t_R$=4.91 min in 8 min chromatography (Method: AS-H_S_3_40_3 ML). LC-MS m/z 494 [M+H-18]$^+$, 512 [M+H]$^+$. $^1$H NMR (400 MHz, CD$_3$OD): δ 8.68 (s, 1H), 8.12 (s, 1H), 7.80 (s, 1H), 6.54 (s, 1H), 6.00-5.87 (m, 1H), 5.20-5.08 (m, 1H), 5.07 (s, 2H), 4.50-4.46 (m, 1H), 4.14-4.08 (m, 1H), 3.98-3.90 (m, 1H), 3.27 (s, 3H), 2.39-2.32 (m, 1H), 1.29 (s, 2H), 1.18 (d, J=6.8 Hz, 3H), 1.04 (d, J=6.8 Hz, 3H).

Example 30

(R)-methyl 2-(8-(hydroxymethyl)-1-isopropyl-7-(methylsulfonyl)-3,4-dihydrobenzo[4,5]imidazo[1,2-a]pyrazin-2(1H)-yl)-4-(trifluoromethyl)pyrimidine-5-carboxylate

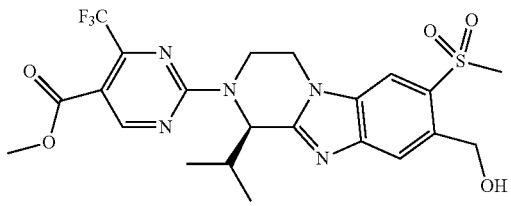

The title compound was prepared by a procedure analogous to those described in Example 12 by using methyl 2-chloro-4-(trifluoromethyl)pyrimidine-5-carboxylate instead of ethyl 2-chloro-4-(trifluoromethyl)pyrimidine-5-carboxylate as a reagent. LC-MS m/z 528 [M+H]$^+$. $^1$H NMR (400 MHz, CD$_3$OD): δ 9.04 (s, 1H), 8.25 (s, 1H), 7.96 (s, 1H), 6.12-6.06 (m, 1H), 5.46-5.34 (m, 1H), 5.11 (s, 2H), 4.54 (dd, J$_1$=12.4 Hz, J$_2$=3.2 Hz, 1H), 4.24 (td, J$_1$=12.0 Hz, J$_2$=5.2 Hz, 1H), 3.95 (dddd, J$_1$=14.4 Hz, J$_2$=12.0 Hz, J$_3$=4.4 Hz, 1H), 3.89 (s, 3H), 3.26 (s, 3H), 2.64-2.54 (m, 1H), 1.29 (d, J=6.8 Hz, 3H), 1.07 (d, J=6.8 Hz, 3H).

Example 31

LXR α/β Radioligand Binding Assay

Compounds of the invention were assessed in a competition binding assay where different concentrations of compounds were incubated with the LXR ligand binding domain (LBD) in the presence of radiolabeled LXR ligand [$^3$H]TO901317. The amount of the LXR-LBD that complexed with [$^3$H]TO901317 was measured by scintillation proximity assay (SPA) employing non-specific binding of LXR-LBD to poly-lysine coated Yttrium silicate beads. Partially purified LXR α or β LBD protein (15-45 nM) was incubated at rt for 30 min with 15 nM [$^3$H]TO901317 (25-40 Ci/mmol) and different concentrations of test compounds in 80 μL of phosphate buffered saline (PBS) buffer containing 2.5% DMSO, 1% glycerol, 2 mM EDTA, 2 mM CHAPS and 5 mM DTT in 96-well plates. Poly-lysine SPA beads (50 μg) were added to each well and the total volume was adjusted to 120 μL. The plates were shaken on an orbital shaker for 20 min and then allowed to settle for 10 more minutes at rt before a brief centrifugation at 2,000 rpm for 1 min. The SPA signal was measured on a MicroBeta® liquid scintillation counter (Perkin Elmer, Waltham, Mass.), and the results were used for calculating IC50 values based on the total binding (DMSO control) and non-specific binding (5 μM of unlabeled T0901317) controls. The K$_i$ values were calculated according to equation 1, where [RL] is the final concentration of [$^3$H]T0901317 in the assay, and the K$_d$ values of 20 nM and 10 nM of TO901317 for LBDs of LXRα and LXRβ, respectively, were determined by direct titration of the radioligand with these proteins.

$$Ki = \frac{IC50}{\left(1 + \frac{[RL]}{Kd}\right)} \quad (1)$$

Example 32

LXR Luciferase Transcriptional Reporter Gene Assay

The LXR luciferase transcriptional reporter gene assay measures the ability of LXR ligands to promote transcriptional activation via the ligand binding domain (LBD) of LXR. HEK293 cells were grown in DMEM medium containing 10% FBS (Gibco®, #11995-065) and 1× PenStrep (Gibco®, #15140) at 37° C. in 5% CO$_2$ atmosphere. 90% confluent cells from a 150 mm dish were seeded in six 100 mm dishes. The cells were batch-transfected with an expression plasmid containing the Gal4 DNA binding domain fused to either the LBD of LXRα or LXRβ and a luciferase reporter plasmid pG5-Luc (Promega, Madison, Wis.), which has Gal4 response elements upstream of firefly luciferase gene (luc+). Transfection was accomplished with Lipofectamine™ 2000 (Gibco®) according to the manufacturer's suggested protocol. Five hs following transfection, 15 mL of 10% charcoal-treated FBS (Hyclone, #SH30070.03) in DMEM were added to the transfected dishes without removing transfection media, and then incubate the cells at 37° C. overnight. The next day, the cells from the transfected dish were trypsinized, washed with PBS, resuspended in 10% charcoal-treated DMEM media and plated into 96-well plates with 60,000 cells/100 μL per well. The cells were incubated at 37° C. for ~4 h before addition of 100 μL of test compound or control ligand at different concentrations (final DMSO concentration at 0.2%). Following incubation of the cells for 16 h with substances, the culture media were dumped and Bright-Glo™ luciferase reagent (Promega, Cat. #E2610) was added to lyse the cells and initiate the luciferase reaction. Luminescence, as a measure of luciferase activity, was detected in a plate reader (Victor2, PE-Wallac). Transcriptional activation in the presence of a test substance was expressed as fold-change in luminescence compared to that of cells incubated in the absence of the substance. EC50 values were calculated using the XLfit™ program (IDBS, Guilford, UK).

Example 33

Compounds of the invention were tested as described in Examples 31 and 32. The biological data are presented in the table below.

| Compound | LXRα BINDING K$_i$ (nM) | LXRβ BINDING K$_i$ (nM) | LXRα CELL EC50 (nM) | LXRβ CELL EC50 (nM) |
| --- | --- | --- | --- | --- |
| E1 | 1400 | 191 | 1580 | 350 |
| E2 | 1600 | 176 | 2370 | 377 |
| E3 | >3330 | 1160 | 17300 | 4620 |
| E4 | 1540 | 137 | 2100 | 293 |
| E5 | >3330 | >2500 | >20000 | 2690 |
| E6a | 277 | 14 | 294 | 21 |
| E6b | >3330 | 1190 | 8530 | 931 |
| E7a | 253 | 14 | 289 | 23 |
| E7b | >3330 | >2500 | 17300 | 2180 |
| E8a | >3330 | 1650 | 14900 | 2040 |
| E8b | 74 | 13 | 224 | 21 |
| E8c | 65 | 9 | 216 | 19 |

-continued

| Compound | LXRα BINDING K$_i$ (nM) | LXRβ BINDING K$_i$ (nM) | LXRα CELL EC50 (nM) | LXRβ CELL EC50 (nM) |
| --- | --- | --- | --- | --- |
| E8d | >3330 | 1330 | 13800 | 2040 |
| E9a | 136 | 17 | 294 | 16 |
| E9b | >3330 | 1360 | >20000 | 1340 |
| E10a | >3330 | >2500 | >20000 | 2400 |
| E10b | 72 | 7 | 290 | 26 |
| E10c | 106 | 7 | 171 | 12 |
| E10d | >3330 | 1940 | >20000 | 1660 |
| E11a | 160 | 14 | 394 | 68 |
| E11b | 236 | 23 | 1040 | 103 |
| E12 | 49 | 6 | 300 | 50 |
| E13a | 409 | 17 | 475 | 45 |
| E13b | >3330 | 1040 | 10200 | 1045 |
| E14a | >3330 | >2500 | >20000 | 7540 |
| E14b | >3330 | >2500 | >20000 | >20000 |
| E15a | >3330 | 240 | >20000 | >20000 |
| E15b | >3330 | >2500 | >20000 | >20000 |
| E16a | >3330 | 376 | >20000 | 1730 |
| E16b | >3330 | >2500 | >20000 | >20000 |
| E17a | 2130 | 220 | 5360 | >20000 |
| E17b | >3330 | >2500 | >20000 | 4900 |
| E18 | 70 | 8 | 154 | 24 |
| E19 | >3330 | >2500 | >20000 | >20000 |
| E20a | 1764 | 110 | >20000 | >20000 |
| E20b | >3330 | >2500 | >20000 | >20000 |
| E21 | 83 | 10 | 116 | 10 |
| E22a | 149 | 12 | 690 | 107 |
| E22b | >3330 | >2500 | >20000 | 11500 |
| E23a | 237 | 21 | 1480 | 306 |
| E23b | >3330 | 2440 | >20000 | 1340 |
| E24a | 56 | 7 | 529 | 134 |
| E24b | 198 | 20 | 1010 | 150 |
| E24c | >3330 | 1690 | >20000 | 18200 |
| E24d | >3330 | >2500 | >20000 | >20000 |
| E25a | 83 | 6 | 562 | 83 |
| E25b | >3330 | >2500 | >20000 | 10800 |
| E26 | 46 | 7 | 259 | 16 |
| E27a | 23 | 2 | 88 | 10 |
| E27b | 3240 | 712 | 3600 | 1440 |
| E28 | 26 | 5 | 336 | 72 |
| E29a | 987 | 50 | 2290 | >20000 |
| E29b | >3330 | >2500 | 12700 | 3290 |
| E30 | 129 | 10 | 266 | 17 |

What is claimed is:

1. A compound represented by the following structural formula:

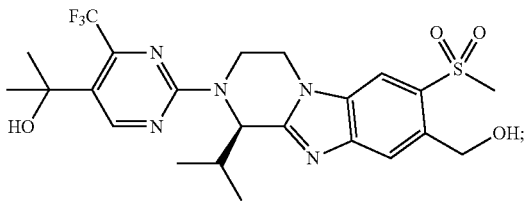 [SMILES: CC(C)[C@@H]1c2nc3cc(CO)c(S(C)(=O)=O)cc3n2CCN1c1ncc(C(C)(C)O)c(C(F)(F)F)n1]

or a pharmaceutically acceptable salt thereof.

2. A pharmaceutical composition comprising a pharmaceutical carrier or diluent and a compound represented by the following structural formula:

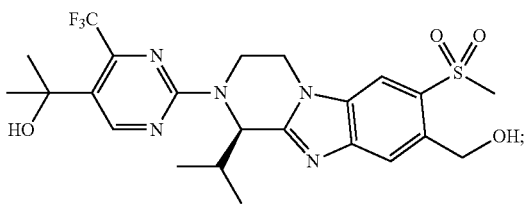 [SMILES: CC(C)[C@@H]1c2nc3cc(CO)c(S(C)(=O)=O)cc3n2CCN1c1ncc(C(C)(C)O)c(C(F)(F)F)n1]

or a pharmaceutically acceptable salt thereof.

3. A method of treating a subject with dermatitis comprising administering an effective amount of a compound represented by the following structural formula:

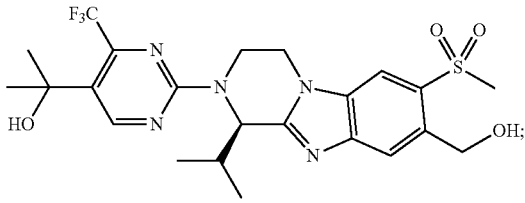 [SMILES: CC(C)[C@@H]1c2nc3cc(CO)c(S(C)(=O)=O)cc3n2CCN1c1ncc(C(C)(C)O)c(C(F)(F)F)n1]

or a pharmaceutically acceptable salt thereof to the subject.

* * * * *